US009493511B2

(12) United States Patent
Frydrych et al.

(10) Patent No.: US 9,493,511 B2
(45) Date of Patent: Nov. 15, 2016

(54) CYCLOSPORIN ANALOGS

(71) Applicant: Allergan, Inc., Irvine, CA (US)

(72) Inventors: Catherine Simone Victoire Frydrych, Sawbridgeworth (GB); William Robert Carling, Bishop's Stortford (GB); Michael E. Garst, Newport Beach, CA (US); Michael E. Stern, Mission Viejo, CA (US); Christopher S. Schaumburg, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/534,677

(22) Filed: Nov. 6, 2014

(65) Prior Publication Data

US 2015/0065433 A1 Mar. 5, 2015

Related U.S. Application Data

(63) Continuation of application No. 13/270,964, filed on Oct. 11, 2011, now abandoned.

(60) Provisional application No. 61/392,449, filed on Oct. 12, 2010.

(51) Int. Cl.
*C07K 7/64* (2006.01)
*C07K 1/113* (2006.01)
*A61K 38/00* (2006.01)

(52) U.S. Cl.
CPC ............... *C07K 7/645* (2013.01); *C07K 1/113* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,649,047 A | 3/1987 | Kaswan | |
| 4,839,342 A | 6/1989 | Kaswan | |
| 5,474,979 A | 12/1995 | Ding et al. | 514/20.5 |
| 5,965,527 A | 10/1999 | Barriere et al. | |
| 5,977,067 A | 11/1999 | Evers et al. | |
| 5,994,299 A | 11/1999 | Barriere et al. | |
| 8,188,052 B2 | 5/2012 | Houck | |
| 8,551,952 B2 | 10/2013 | Houck | |
| 2005/0059583 A1 | 3/2005 | Acheampong et al. | |
| 2010/0009953 A1 | 1/2010 | Garst | |
| 2010/0062975 A1 | 3/2010 | Houck | |
| 2012/0270804 A1 | 10/2012 | Houck | |
| 2013/0210704 A1 | 8/2013 | Su et al. | |

FOREIGN PATENT DOCUMENTS

| | | |
|---|---|---|
| EP | 0194972 A2 | 9/1986 |
| WO | WO9849193 | 4/1998 |
| WO | WO9828329 | 7/1998 |
| WO | WO9828330 | 7/1998 |
| WO | WO 99-65933 | 12/1999 |
| WO | WO 00-61168 | 10/2000 |
| WO | WO2007008894 A2 | 1/2007 |
| WO | WO2007136759 A2 | 11/2007 |
| WO | 2012005494 | 6/2012 |
| WO | WO20120075494 A1 | 6/2012 |
| WO | WO 2013028615 | 2/2013 |

OTHER PUBLICATIONS

Seebach et al, "Modification of Cyclosporin A (CS): Generation of an Enolate at Thesarcosine Residue and Reactions with Electrophiles", Chimica Acta, vol. 76, No. 4 pp. 1564-1590, 1993.

*Primary Examiner* — Karlheinz R Skowronek
*Assistant Examiner* — Ronald Niebauer
(74) *Attorney, Agent, or Firm* — Barbara C. Potts

(57) ABSTRACT

Disclosed herein are novel analogs of cyclosporin, pharmaceutical compositions containing them, and methods for their use in the treatment of dry eye and other conditions.

4 Claims, No Drawings

CYCLOSPORIN ANALOGS

CROSS REFERENCE

This application is a continuation of U.S. patent application Ser. No. 13/270,964, filed on Oct. 11, 2011, which claims the benefit of U.S. Provisional Patent Application Ser. No. 61/392,449, filed on Oct. 12, 2010, the entire disclosure of both of which are incorporated herein by this specific reference.

Disclosed herein are novel analogs of cyclosporin, pharmaceutical compositions containing them, and methods for their use in the treatment of dry eye and other conditions.

BACKGROUND

Cyclosporins are a class of poly-N-methylated cyclic undecapeptides. There are naturally occurring cyclosporins such as cyclosporin A, and non-natural cyclosporin ("Cs") derivatives.

Cyclosporin A, for example, has the following structure:

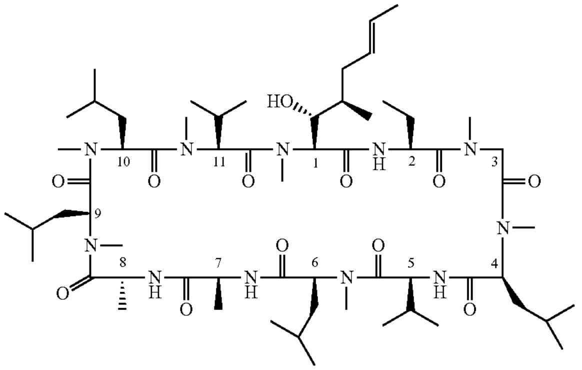 [SMILES: C/C=C/C[C@@H](C)[C@@H](O)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

The following structure shows the 11 amino acid residues of cyclosporin A:

```
MeLeu-MeVal-MeBmt-αAbu-Sar
|  10     11    1     2    3 |
MeLeu                        |
|9                           |
└─DAla-Ala-MeLeu-Val-MeLeu
   8     7    6     5    4
```

DETAILED DESCRIPTION

The claimed invention relates to novel compounds of the following formula (I) and pharmaceutically acceptable salts thereof:

(I)

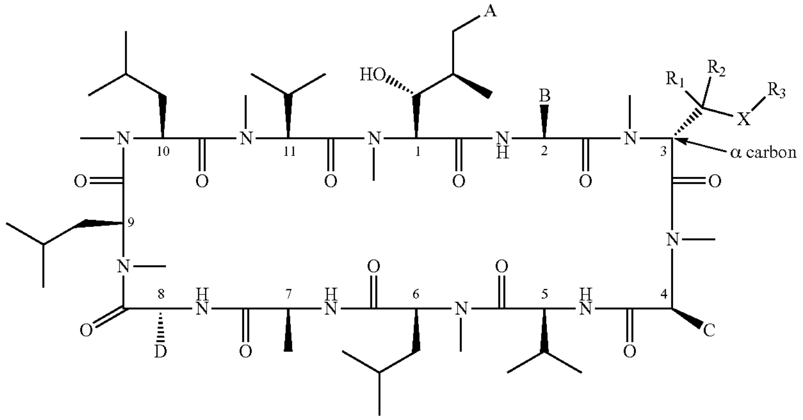

The claimed novel compounds of formula (I) result from modifications at the α-carbon of the 3-position amino acid (sarcosine) of "Cs scaffolds," which as used herein refers to different cyclosporins (e.g., Cs A, Cs C, Cs D, etc.) that vary from each other in the identities of one or more of substituents A, B, C, and D. In other words, a "Cs scaffold" refers to a novel compound of formula (I) less the moiety at the α-carbon of the 3-position amino acid.

A, B, C, and D are defined as follows. A represents $—CH{=}CHR$, $—CH{=}CH—CH{=}CHR$, or $—CH_2CH_2R$, wherein R represents (a) $—CH_3$, (b) $—CH_2SH$, (c) $—CH_2S—C_n$ wherein n=1-6, (d) $—CH_2$-carboxyl, i.e.,

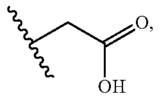 [SMILES: *CC(=O)O]

(e) carboxyl, i.e.,

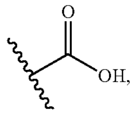 [SMILES: *C(=O)O]

(f) alkoxycarbonyl, i.e.,

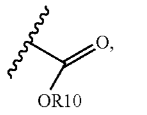

wherein R10=$C_1$-$C_6$ alkyl, or (g) —$CH_2$-alkoxycarbonyl, i.e.,

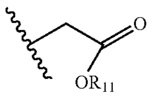

wherein R11=$C_1$-$C_6$ alkyl.

B represents

—$CH_2CH_3$, or 1-hydroxyethyl, i.e.,

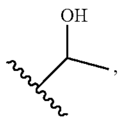 [SMILES: *C(C)O]

isopropyl, i.e.,

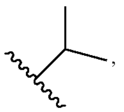 [SMILES: *C(C)C]

or n-propyl, i.e.,

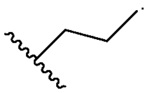 [SMILES: *CCC]

C represents isobutyl, i.e.,

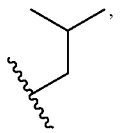 [SMILES: *CC(C)C]

2-hydroxyisobutyl, i.e.,

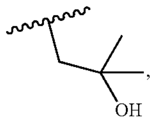 [SMILES: *CC(C)(C)O]

or 1-methylpropyl, i.e.,

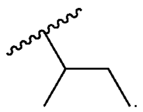 [SMILES: *C(C)CC]

D represents —$CH_3$ or —$CH_2OH$.

In one embodiment of the present invention, A is —CH═$CHCH_3$, B is —$CH_2CH_3$, C is isobutyl, and D is —$CH_3$, as illustrated below in formula (IA):

(IA)

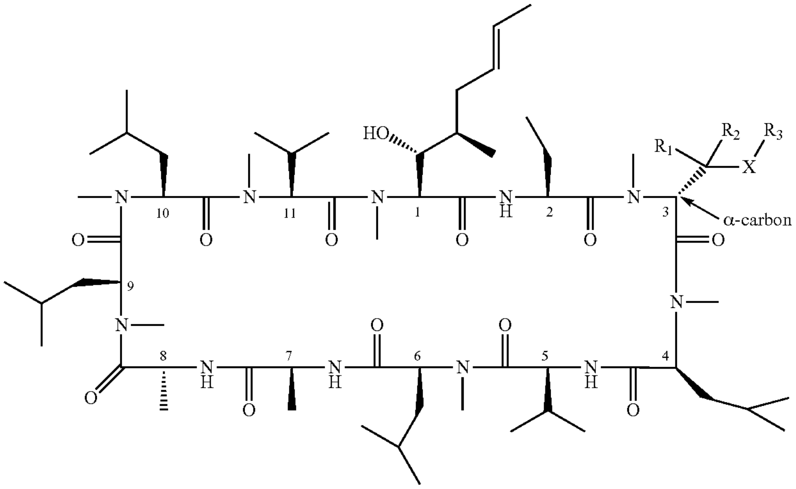

In another embodiment, A is —CH═$CHCH_3$, B is 1-hydroxyethyl, C is isobutyl, and D is —$CH_3$, as illustrated below in formula (IB):

(IB)
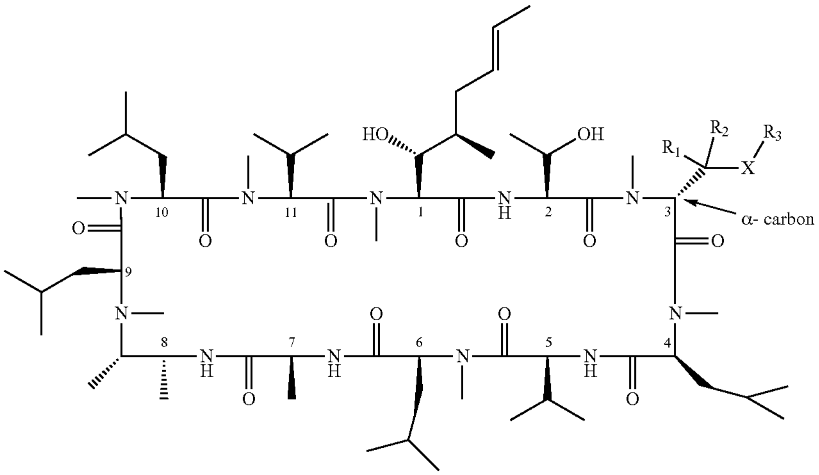
In another embodiment, A is —CH═CHCH$_3$, B is isopropyl, C is isobutyl, and D is —CH$_3$, as illustrated below in formula (IC):
(IC)
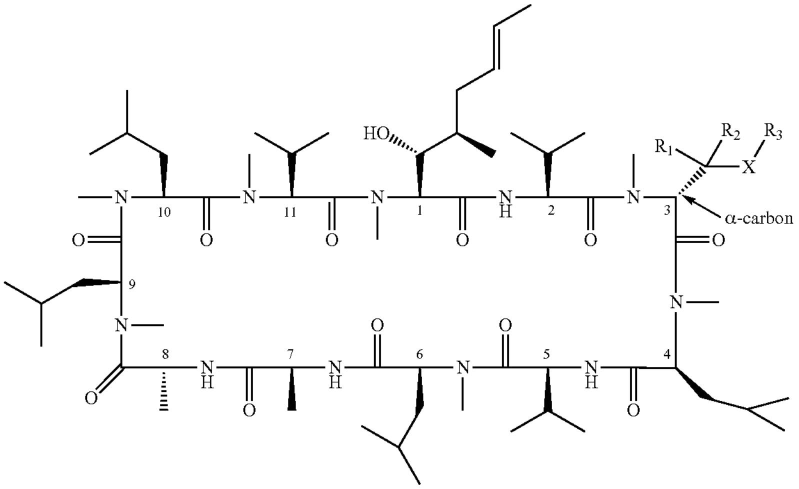
In another embodiment, A is —CH═CHCH$_3$, B is n-propyl, C is isobutyl, and D is —CH$_3$, as illustrated below in formula (ID):
(ID)
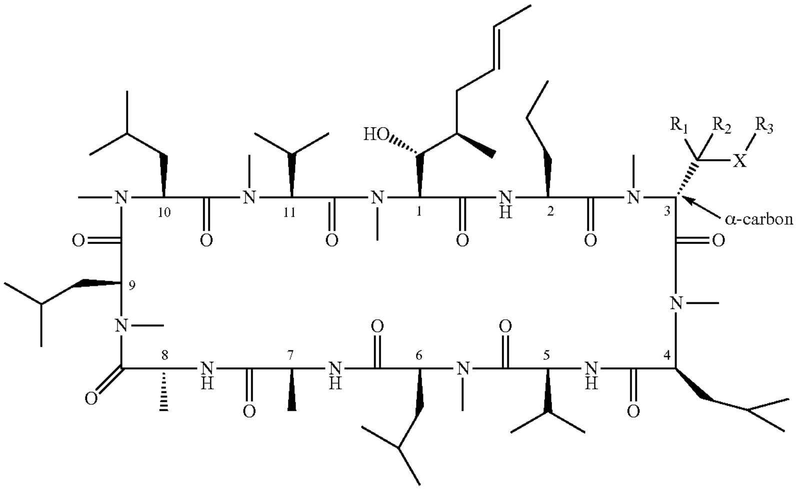

In another embodiment, A is —$CH$=$CHCH_3$, B is —$CH_2CH_3$, C is 1-methylpropyl, and D is —$CH_3$, as illustrated below in formula (IE):
(IE)
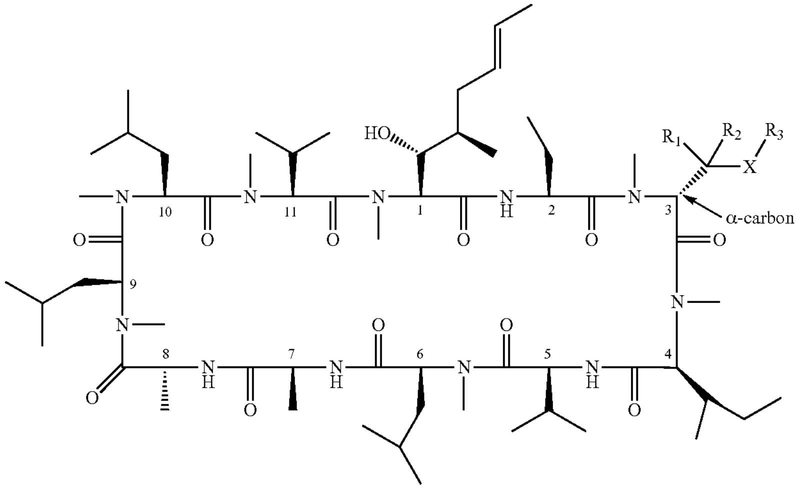
In one embodiment, A is —$CH$=$CHCH_3$, B is —$CH_2CH_3$, C is isobutyl, and D is —$CH_2OH$, as illustrated below in formula (IF):
(IF)
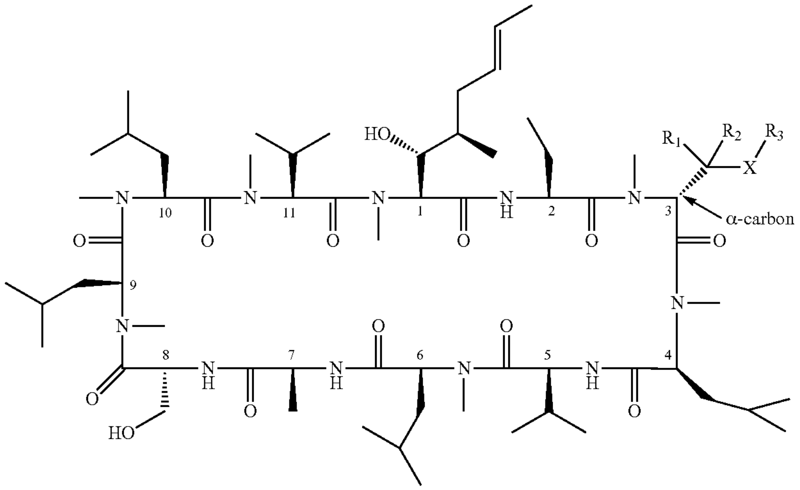
In one embodiment, A is —$CH$=$CHCH_3$, B is —$CH_2CH_3$, C is 2-hydroxy isobutyl, and D is —$CH_3$, as illustrated below in formula (IG):

(IG)
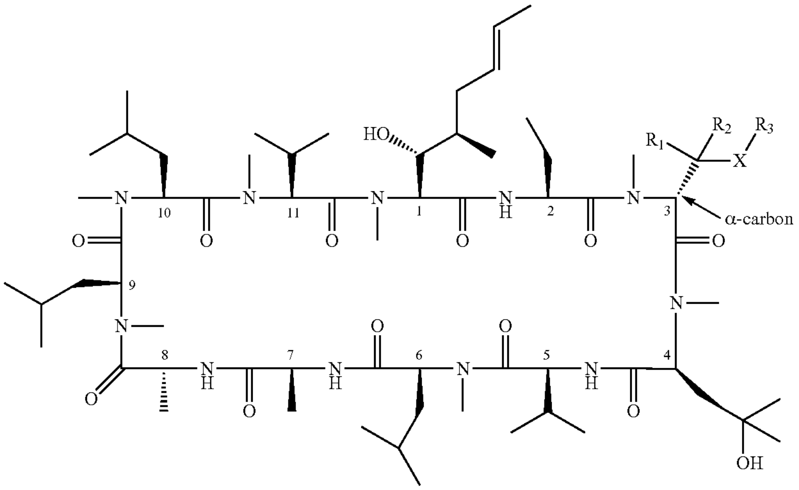
In another embodiment, the variables are as summarized below:
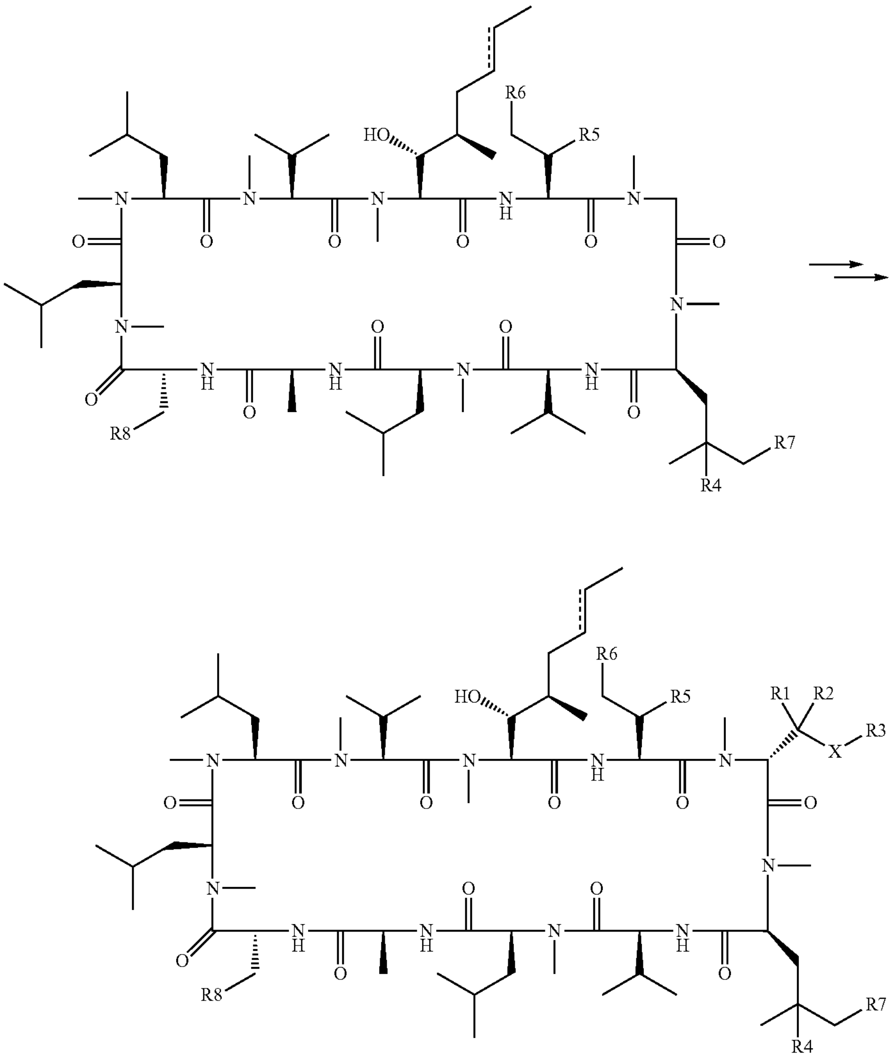

| Scaffold | R4 | R5 | R6 | R7 | R8 |
|---|---|---|---|---|---|
| CsA | H | H | H | H | H |
| CsC | H | OH | H | H | H |
| CsD | H | Me | H | H | H |
| CsG | H | H | Me | H | H |
| NIM811 | H | H | H | Me | H |
| DSer8 | H | H | H | H | OH |
| Scy | OH | H | H | H | H |

In formula (I), the amino acids of various types of cyclosporine scaffold are labeled numerically from 1 to 11. In one embodiment, the modifications of the invention occur at the α-carbon of the position-3 amino acid (sarcosine at the 3-position) of the Cs scaffold. The modification generally comprises replacement of a hydrogen atom at the α-carbon of the position-3 amino acid with a moiety in formula (I) wherein:

$R_1$ and $R_2$, which are identical or different, each represents hydrogen or $C_1$-$C_4$ alkyl, or together represent $C_3$-$C_7$ cycloalkyl;

X represents sulfur or —$S(O)_n$, wherein n is 1 or 2;

$R_3$ represents hydrogen; straight or branched $C_1$-$C_6$ alkyl; straight or branched $C_2$-$C_6$ alkenyl; straight or branched $C_2$-$C_6$ alkynyl; $C_3$-$C_7$ cycloalkyl; $C_4$-$C_7$ heterocyclyl having 1-3 heteroatoms selected from nitrogen, oxygen, and sulfur; aryl; heteroaryl;

—$(CHR{=})_m$—NH—$CNH_2NH$;

—$(CHR')_m$—COOH;

—$(CHR')_m$—NHR";

—$(CHR')_m$—NHCOR";

wherein m is 1, 2, 3, 4, 5, or 6;

each R' is independently H, straight or branched $C_1$-$C_6$ alkyl, straight or branched $C_2$-$C_6$ alkenyl; straight or branched $C_2$-$C_6$ alkynyl; $C_3$-$C_7$ cycloalkyl; $C_4$-$C_7$ heterocyclyl having 1-3 heteroatoms selected from nitrogen, oxygen, and sulfur; aryl; heteroaryl; or is absent (permitting, in such case, —$(CHR')_m$ to represent an unsaturated moiety such as —CH—CH).

R" is —$(CHR')_pN(CH_3)_2$, —$(CHR')_p$NHCOC, —$(CHR')_p$NHCOOH, wherein p is 0, 1, 2, 3, 4, 5, or 6; and wherein $R_3$ may be optionally substituted with one or more groups, identical or different, of $C_1$-$C_6$ alkyl; halogen; hydroxyl; alkoxycarbonyl; carboxyl; cycloalkyl; saturated or partially unsaturated 5-6 member heterocyclyl having 1-3 heteroatoms selected from nitrogen, oxygen, and sulfur, which heterocyclyl is optionally substituted by one or more groups of $C_1$-$C_6$ alkyl; aryl; heteroaryl; amino; monoalkylamino; dialkylamino; amidino; guanidine; or urea.

COMPOUND EXAMPLES

Embodiments of formula (I) include, but are not limited to, the following compounds of formula (I) (only the moiety at the α-carbon of the position-3 amino acid is shown; wavy lines represent the rest of the Cs compounds of formula (I)):

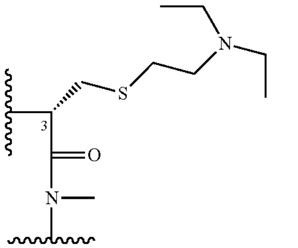

-continued

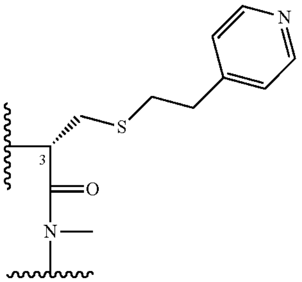

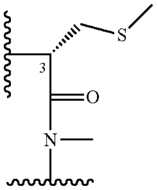

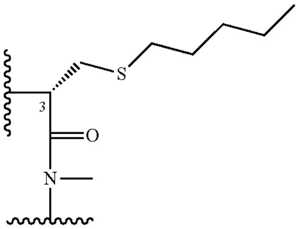

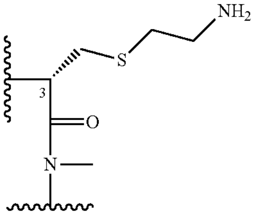

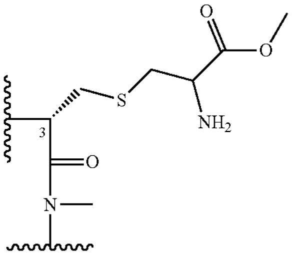

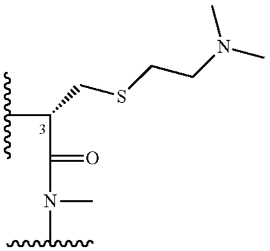

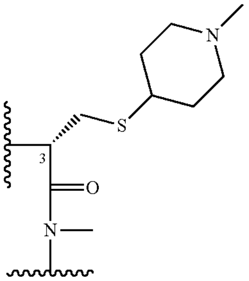

-continued
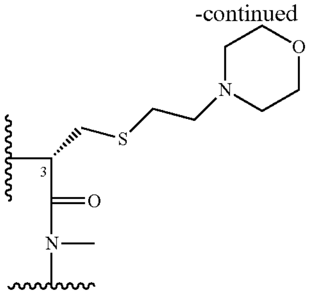
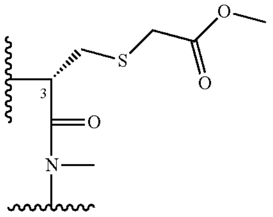
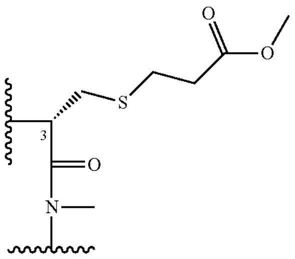
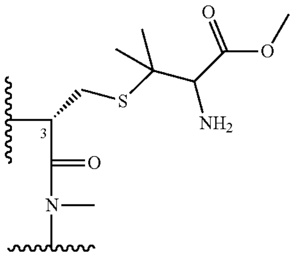
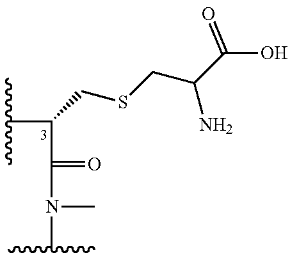
-continued
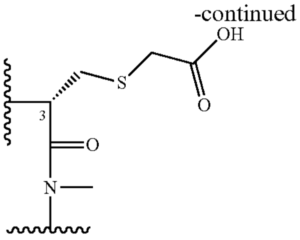
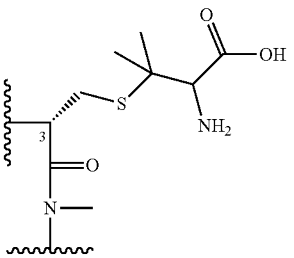
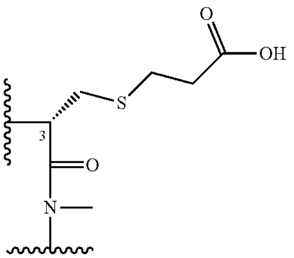
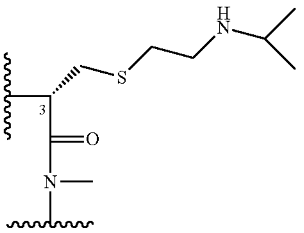
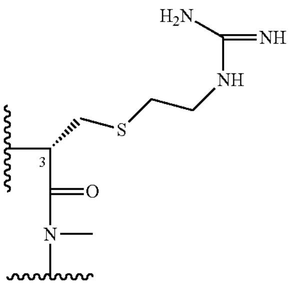
The present invention also relates to novel intermediates useful for the preparation of compounds of formula (I). The novel intermediates are compounds of the following formula (III):

(III)

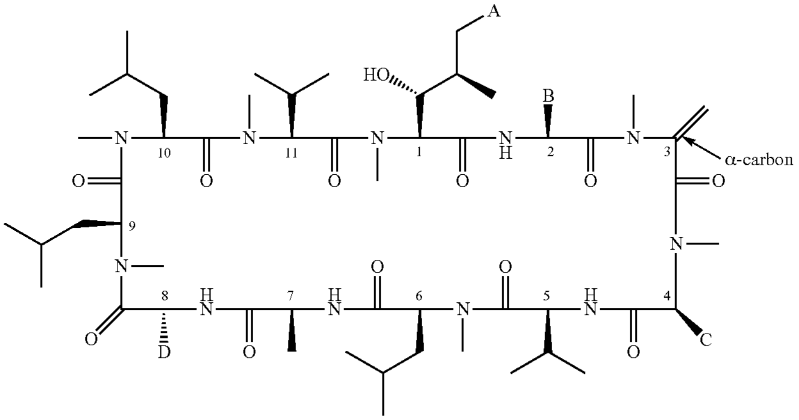

wherein A, B, C, and D are as defined above.

The following is a non-limiting embodiment of formula (III):

Formula (III) Compound Example 1

[Methylene-Sar]$^3$ cyclosporin A

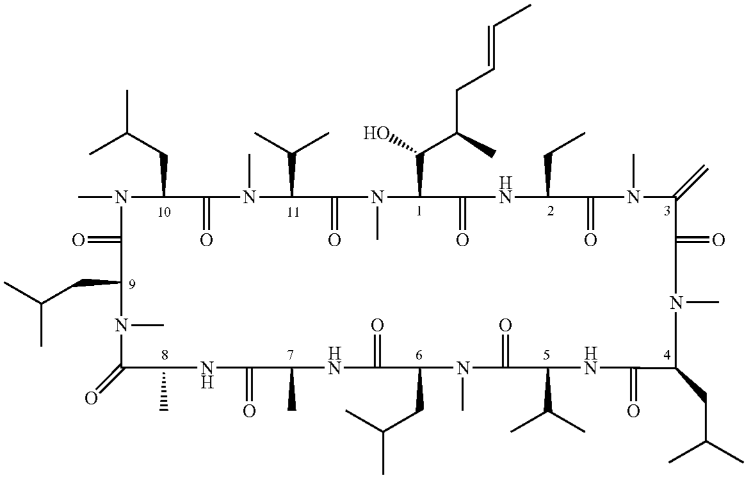 [SMILES: C=C1C(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N(C)[C@H]([C@H](O)[C@H](C)C/C=C/C)C(=O)N[C@H](CC)C(=O)N1C]

ESMS $MH^+$1214.8, $MNa^+$1236.8

All NMR data show selected diagnostic protons.

$^1H$ NMR ($CDCl_3$, ppm) δ 4.98 (d, 1H, olefin $CH_2$), 5.25 (d, 1H, olefin $CH_2$), 7.17 (d, 1H, amide NH), 7.52 (d, 1H, amide NH), 7.59 (d, 1H, amide NH), 7.85 (d, 1H, amide NH).

$^{13}C$ NMR ($CDCl_3$, ppm) δ 143.96 (olefin C), 108.09 (olefin $CH_2$).

The present invention also relates to a process for the preparation of a compound of formula (III), comprising:

reacting a compound of the formula (II)

(II)

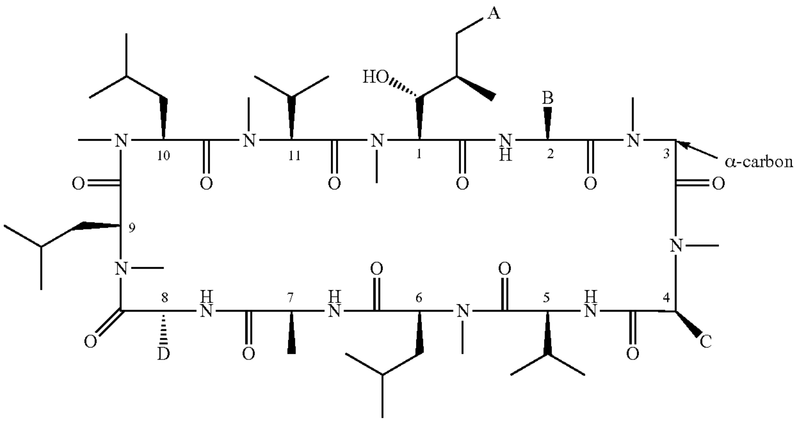

wherein A, B, C, and D are as previously defined, with a strong base (for example, lithium diisopropylamide or other strong base), at a temperature in the range of −78° C. to −70° C., followed by treatment with a flow of carbon dioxide gas between −70° C. and 15° C., followed by treatment with excess chloromethylchloroformate between −50° C. and room temperature, followed by quenching of the reaction mixture with acetic acid at 0° C. to room temperature to generate a compound of formula (III).

"Alkynyl" refers to a monovalent linear or branched hydrocarbon radical having 2 to 6 carbon atoms and one or more triple bonds. Examples include, but are not limited to, ethynyl, propynyl and butynyl.

"Cycloalkyl" refers to monovalent saturated or partially unsaturated cyclic hydrocarbon radical having 3 to 6 carbon atoms. Examples include, but are not limited to, cyclopropyl, cyclobutyl, cyclopentyl, and cyclohexyl.

"Heterocyclyl" refers to monovalent, saturated or partially unsaturated cyclic hydrocarbon radical having 3 to 6

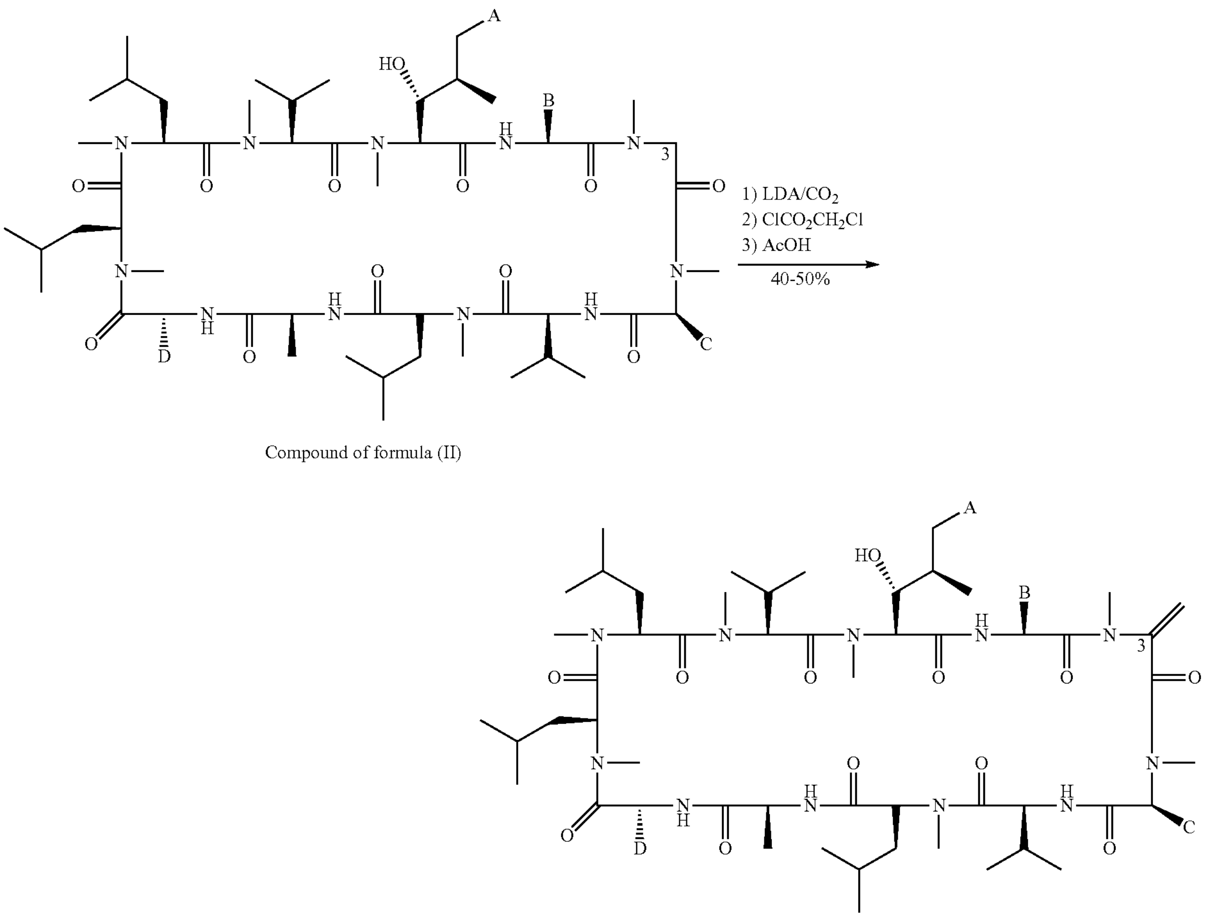

Compound of formula (II)

Compound of formula (III)

Definitions

"Alkyl" refers to a monovalent linear or branched hydrocarbon radical having 1 to 6 carbon atoms. Examples include, but are not limited to, methyl, ethyl, propyl (e.g., 1-propyl, isopropyl), butyl (e.g., 1-butyl, isobutyl, sec-butyl, tert-butyl), pentyl (e.g., 1-pentyl, neopentyl), and hexyl (e.g., 3-hexyl).

"Alkenyl" refers to a monovalent linear or branched hydrocarbon radical having 2 to 6 carbon atoms and one or more double bonds. Examples include, but are not limited to, ethenyl, propenyl, and butenyl.

ring atoms, at least one of which is a heteroatom selected from nitrogen, oxygen and sulfur. The radical may be on a carbon or a heteroatom. Examples include, but are not limited to, morpholinyl, piperidinyl, pyrrolidinyl, pyranyl, and pyrazolinyl.

"Aryl" refers to monovalent 5-7 member aromatic hydrocarbon radical. Examples include, but are not limited to, phenyl.

"Heteroaryl" refers to monovalent 5-7 member aromatic hydrocarbon radical having one or more heteroatoms selected from nitrogen, sulfur and oxygen. Examples include, but are not limited to, imidazolyl, pyridinyl, furyl, pyrimidinyl and pyrazinyl.

The aforementioned alkyl, alkenyl, alkynyl, cycloalkyl, heterocyclyl, aryl, and heteroaryl radicals may be independently substituted with one or more substituents described herein.

"Amino" refers to the —$NH_2$ or amidogen group.

"Monoalkylamino" refers to the —NHR' group, where R' represents an alkyl, alkenyl, alkynyl and cycloalkyl as defined herein.

"Dialkylamino" refers to the —NRR' group where R and R' independently represents an alkyl, alkenyl, alkynyl and cycloalkyl as defined herein.

"Halogen" refers to bromo, chloro, fluoro, or iodo.

"Hydroxyl" refers to the —OH group.

"Carboxy" refers to the group:

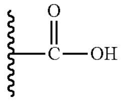

"Alkoxycarbonyl" refers to the group:

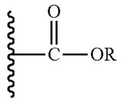

where R represents an alkyl as defined herein.

"Amidino" refers to the groups:

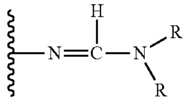

and

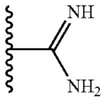

"Guanidino" refers to the group:

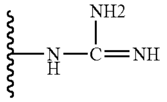 [SMILES: *NC(=N)N]

"Urea" refers to the group:

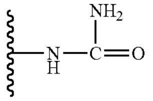 [SMILES: *NC(N)=O]

"Pharmaceutically acceptable salt" refers to any salt of compounds claimed in this application that possesses the biological effectiveness to the compounds and are not toxic or otherwise harmful for pharmaceutical use; these salts may be derived from organic and inorganic counter ions which are well known in the art.

SYNTHESIS EXAMPLES

The invention is illustrated by the following non-limiting synthesis examples. Unless otherwise indicated, the following chemical abbreviations are used in the synthesis examples:

DMF: dimethylformamide
DIPEA: diisopropylethylamine
Me: methyl
THF: tetrahydrofuran
i-Pr: isopropyl
n-Bu: n-butyl The starting materials for the claimed compounds of formula (I), including the Cs scaffolds, can be prepared using synthesis schemes and reagents available in the art, and may be obtained through commercial suppliers. Reagents used for the synthesis of the novel compounds of the present invention can also be obtained through commercial suppliers.

Example 1

[Methylene-Sar][3] cycloorin A

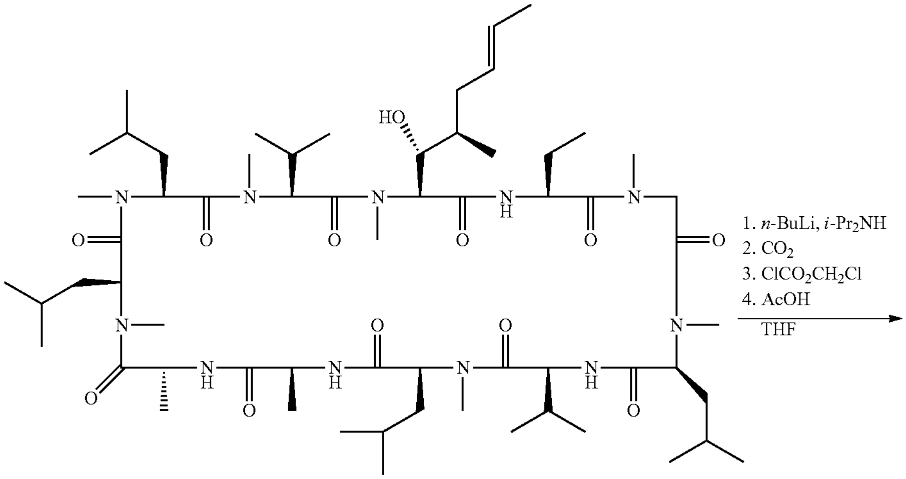

-continued

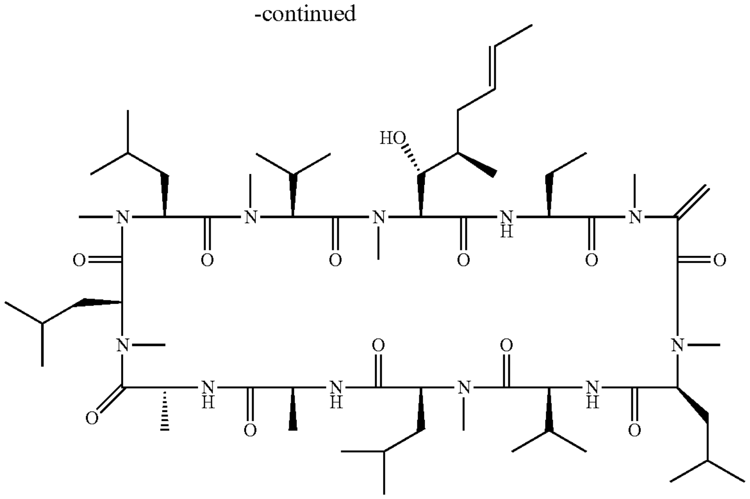

To a solution of diisopropylamine (11.2 ml, 80 mmol) in dry THF (240 ml) at −78° C. under an atmosphere of nitrogen was added dropwise n-butyl lithium (2.5M in hexanes, 32 ml, 80 mmol) and the resulting mixture was stirred at −78° C. for 60 minutes.

A solution of dry cyclosporine A (dried by azeotroping with 2×40 ml toluene then kept in desiccator o/n in presence of $P_2O_5$) (9.6 g, 8.0 mmol) in dry THF (40 ml) was added and the reaction was stirred under the same conditions for 2 h. A flow of carbon dioxide was bubbled through the reaction mixture for 30 minutes with temperature increasing to −50° C. The resulting mixture was allowed to warm to 15° C. over a period of 2 hours then cool back down to −50° C. before the addition of chloromethylchloroformate (7.1 ml, 80 mmol). The reaction mixture was allowed to warm to room temperature overnight then cooled to 0° C. and acetic acid (5 ml, 88 mmol) was added.

The mixture was allowed to warm to room temperature, the solvent evaporated and the resultant mixture was partitioned between ethyl acetate and brine. The organic phase was separated, dried ($Na_2SO_4$) and concentrated to give a yellow oil.

The crude product was purified by MPLC chromatography using a solvent gradient of 100% diethyl ether 96% diethyl ether/4% methanol to give [methylene-Sar]$^3$ cyclosporinA.

ESMS $MH^+$1214.8, $MNa^+$1236.8

$^1$H NMR ($CDCl_3$, ppm) δ 4.98 (d, 1H, olefin $CH_2$), 5.25 (d, 1H, olefin $CH_2$), 7.17 (d, 1H, amide NH), 7.52 (d, 1H, amide NH), 7.59 (d, 1H, amide NH), 7.85 (d, 1H, amide NH).

$^{13}$C NMR ($CDCl_3$, ppm) δ 143.96 (olefin C), 108.09 (olefin $CH_2$).

In a similar way the following compounds were prepared:

[Dihydro-MeBmt]$^1$ [Methylene-Sar]$^3$ cyclosporin A

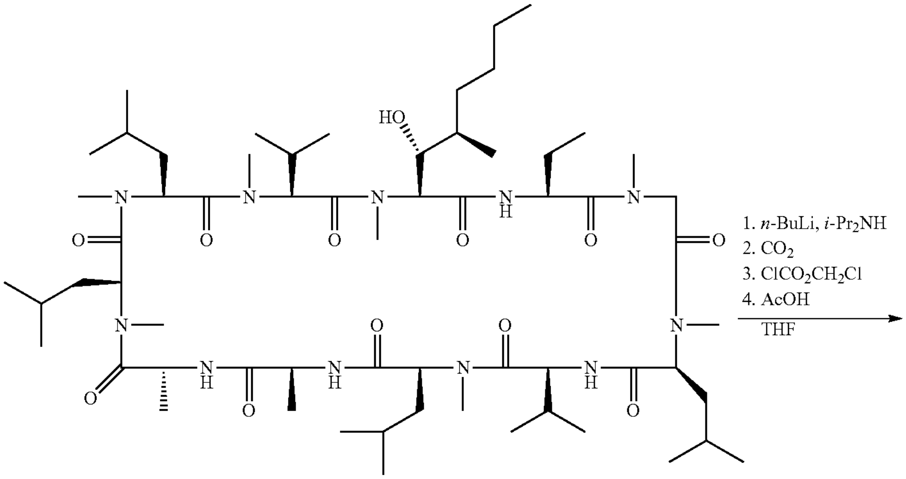

-continued
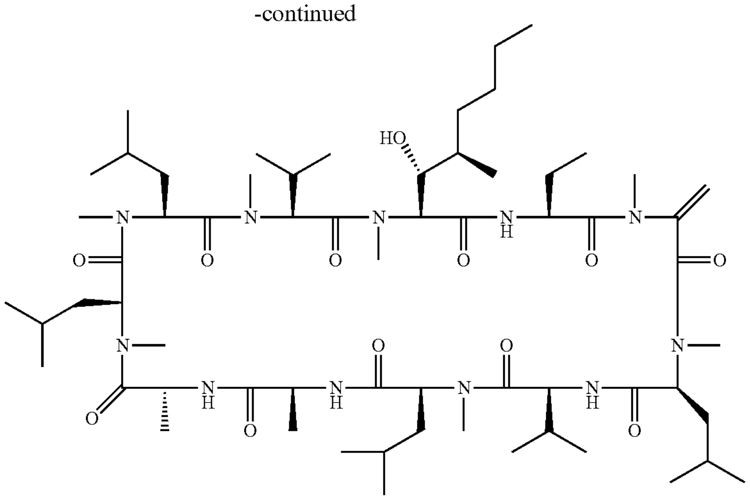
ESMS $MH^+$1216.8, $MNa^+$1238.8
$^1H$ NMR ($CDCl_3$, ppm) δ 7.18 (d, 1H, amide NH), 7.52 (d, 1H, amide NH), 7.57 (d, 1H, amide NH), 7.75 (d, 1H, amide NH).
[Methylene-Sar][3] cyclosporin D
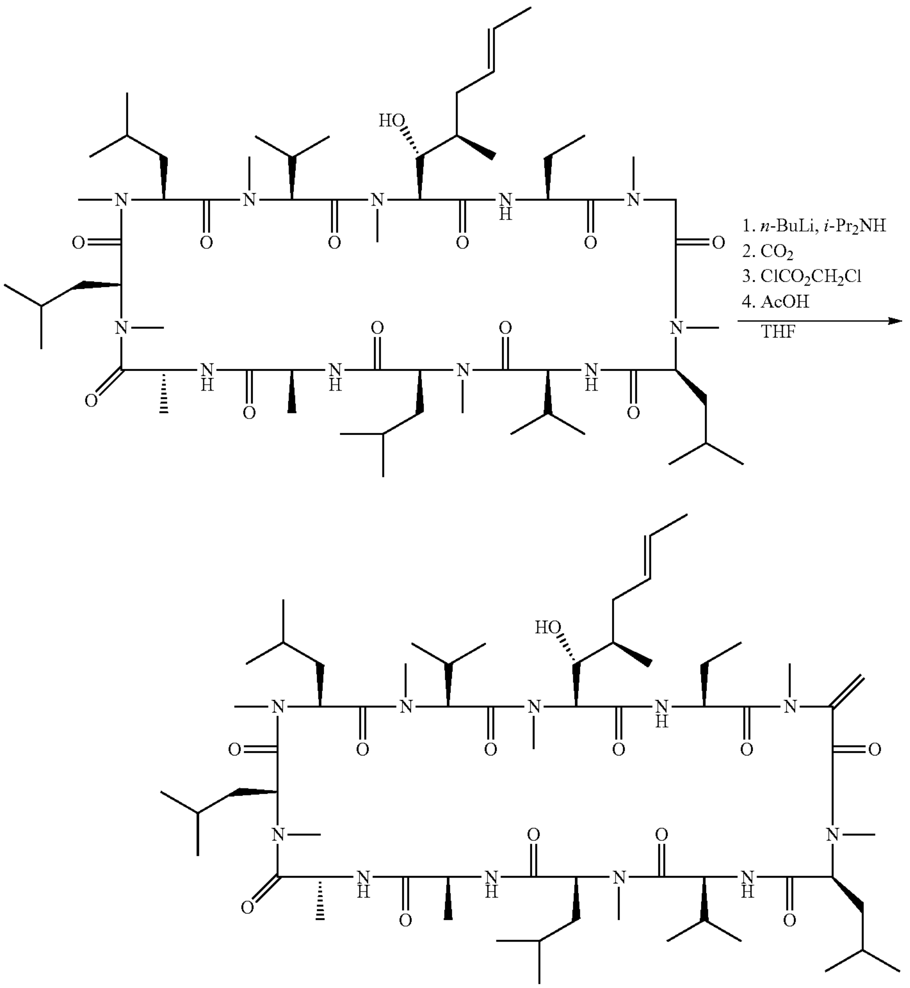

ESMS $MH^+$1228.8, $MNa^+$1250.8

$^1$H NMR ($CDCl_3$, ppm) 7.17 (d, 1H, amide NH), 7.59 (d, 1H, amide NH), 7.63 (d, 1H, amide NH), 7.89 (d, 1H, amide NH).

Example 2

[(S)-2-Diethylaminoethylthiomethyl-Sar]$^3$ cyclosporin A

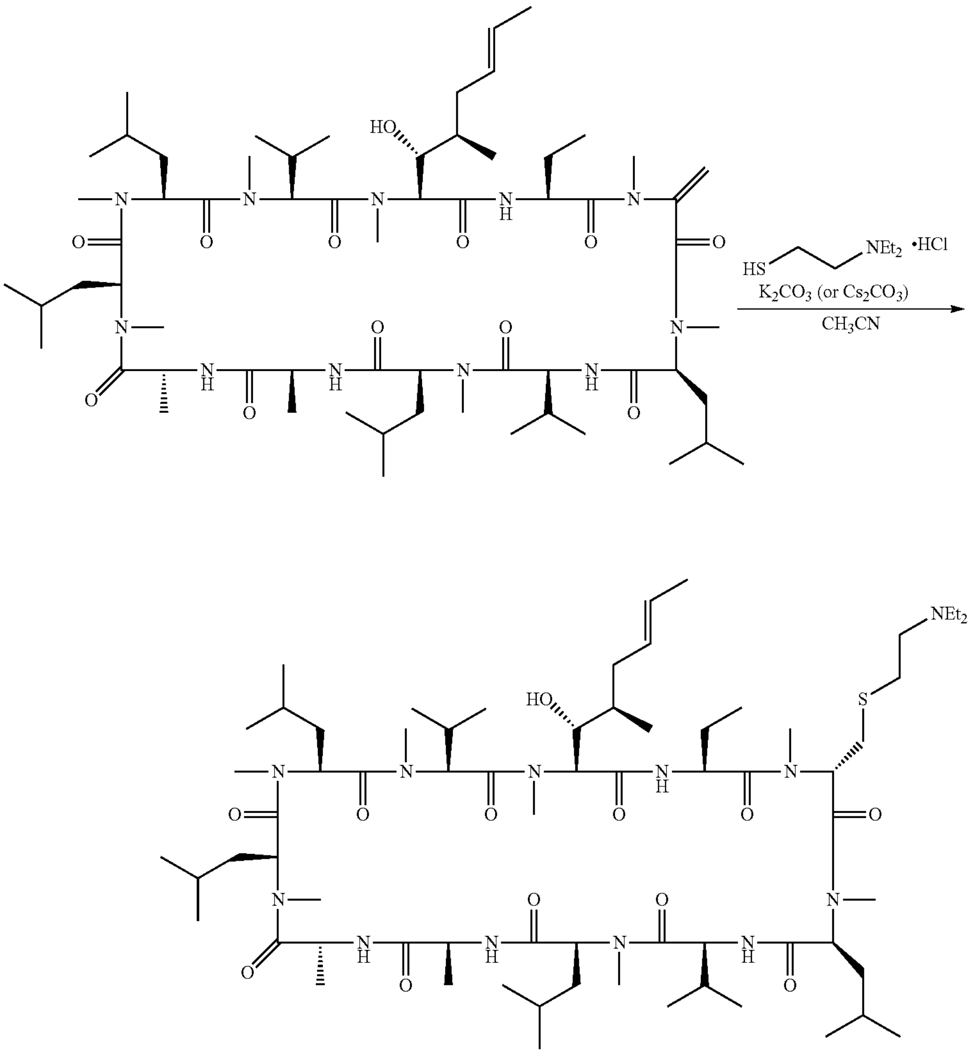

To a solution of [methylene-Sar]$^3$ cyclosporin A (0.232 g, 0.19 mmol) in acetonitrile (15 ml) was added potassium carbonate (0.523 g, 3.8 mmol) and the white suspension was bubbled through with nitrogen for one hour before adding diethylaminoethylthiol hydrochloride salt (0.322 g, 1.9 mmol). The reaction mixture was bubbled through with nitrogen overnight during which time the solvent evaporated. Acetonitrile (15 ml) was added, the white suspension filtered through a pad of sodium sulphate then concentrated to give 315 mg of a colourless oil. Trituration with hexane under ultrasound conditions, followed by decantation of the solution provided 240 mg of a white solid. Purification by MPLC chromatography using a solvent gradient of 100% diethyl ether 95% diethyl ether/5% methanol then 100% diethyl ether followed by a second solvent gradient 100% diethyl ether 90% diethyl ether/10% methanol containing 10% aqueous ammonia (0.88) gave [(S)-2-diethylaminoethylthiomethyl-Sar]$^3$ cyclosporin A.

ESMS $MH^+$1347.9

$^1$H NMR ($CDCl_3$, ppm) δ 0.69 (3H, d), 0.77-1.07 (43H, m) 1.09 (3H, d), 1.18-1.41 (10H, m), 1.41-1.82 (10H, m), 1.93-2.18 (5H, m), 2.33-2.46 (2H, m), 2.53 (4H, q), 2.60-2.72 (6H, m), 2.99 (2H, br d), 3.10 (3H, s), 3.18 (3H, s), 3.27 (6H, s), 3.50 (3H, s, NMe), 3.58 (1H, br d), 3.67 (1H, q), 4.52 (1H, m), 4.60 (1H, t), 4.82 (1H, m), 4.93-5.08 (4H, m), 5.10 (1H, d), 5.26-5.39 (3H, m), 5.51 (1H, dd), 5.69 (1H, dd), 7.16 (1H, d, amide NH), 7.36 (1H, d, amide NH), 7.68 (1H, d, amide NH), 8.13 (1H, d, amide NH).

In a similar way the following compounds were prepared:
[Dihydro-MeBmt]$^1$ [(S)-2-diethylaminoethylthiomethyl-Sar]$^3$ cyclosporin A
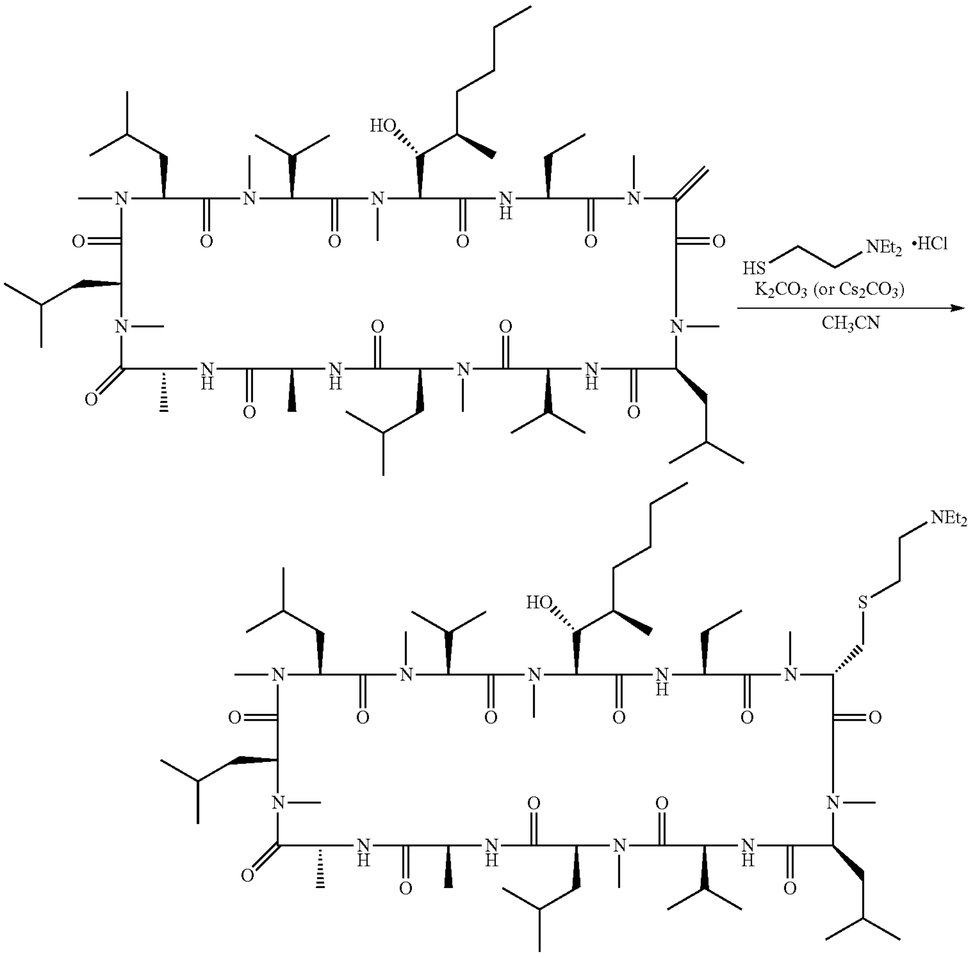
ESMS $MH^+$1350.0
$^1$H NMR ($CDCl_3$, ppm) 67.17 (1H, d, amide NH), 7.37 (1H, d, amide NH), 7.71 (1H, d, amide NH), 8.10 (1H, d, amide NH).
[(S)-2-Diethylaminoethylthiomethyl-Sar]$^3$ cyclosporin D
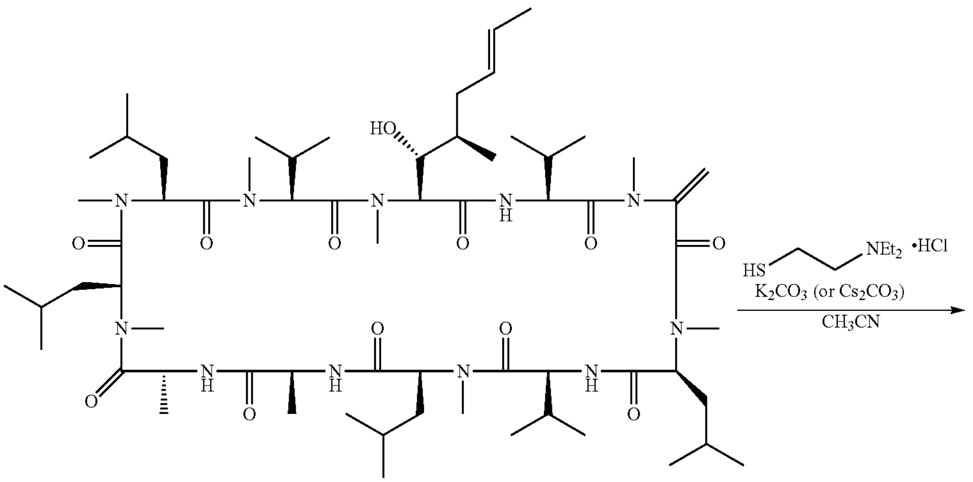

-continued
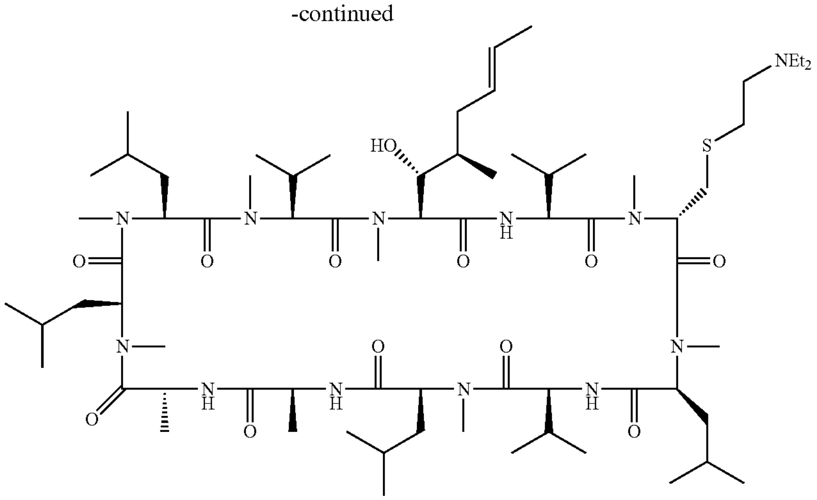
ESMS $MH^+$1361.9
$^1H$ NMR ($CDCl_3$, ppm) δ7.16 (1H, d, amide NH), 7.49 (1H, d, amide NH), 7.72 (1H, d, amide NH), 8.16 (1H, d, amide NH).
Example 3
[(S)-2-(4-pyridyl)ethylthiomethyl-Sar][3] cyclosporin A
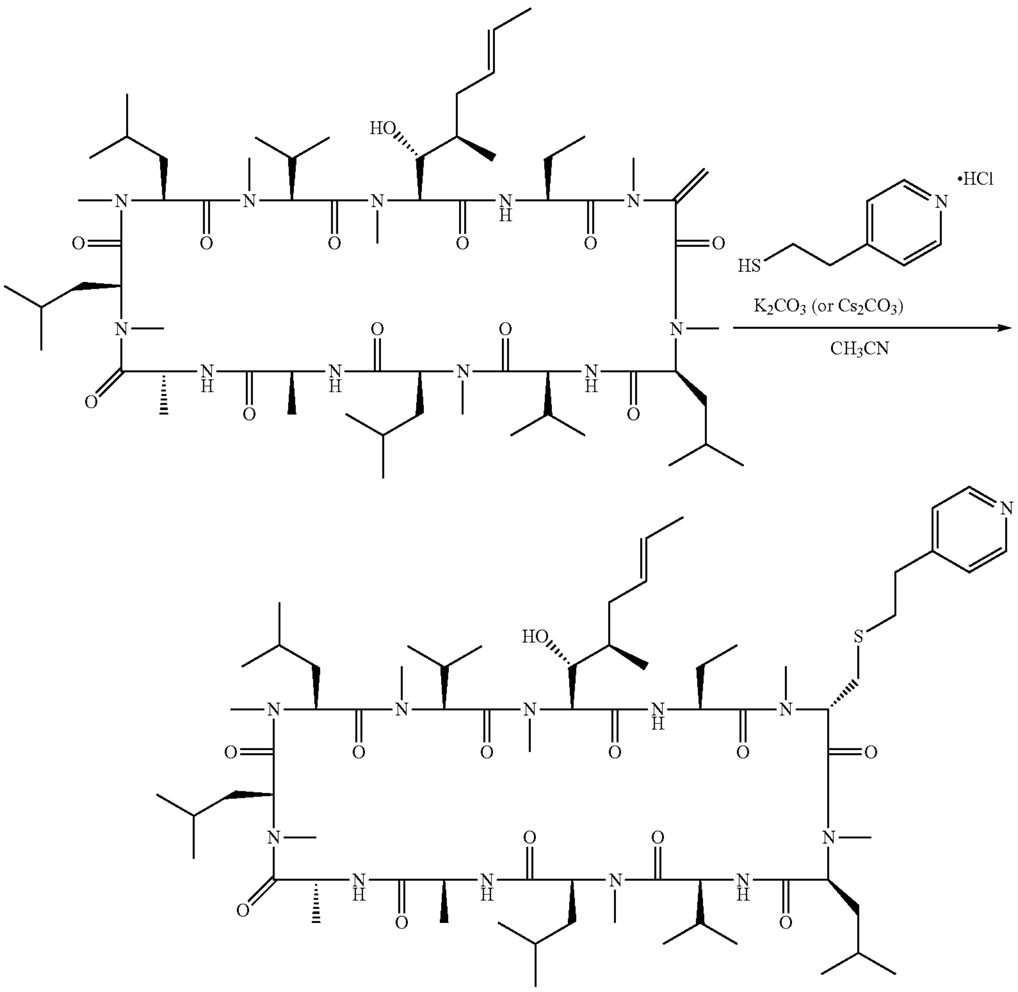

ESMS $MH^+$1354.0
$^1H$ NMR ($CDCl_3$, ppm) δ 7.14 (d, 2H, pyridine), 7.18 (d, 1H, amide NH), 7.31 (d, 1H, amide NH), 7.70 (d, 1H, amide NH), 8.17 (d, 1H, amide NH), 8.54 (d, 2H, pyridine).
Example 4
[(S)-Methylthiomethyl-Sar][3] cyclosporin A
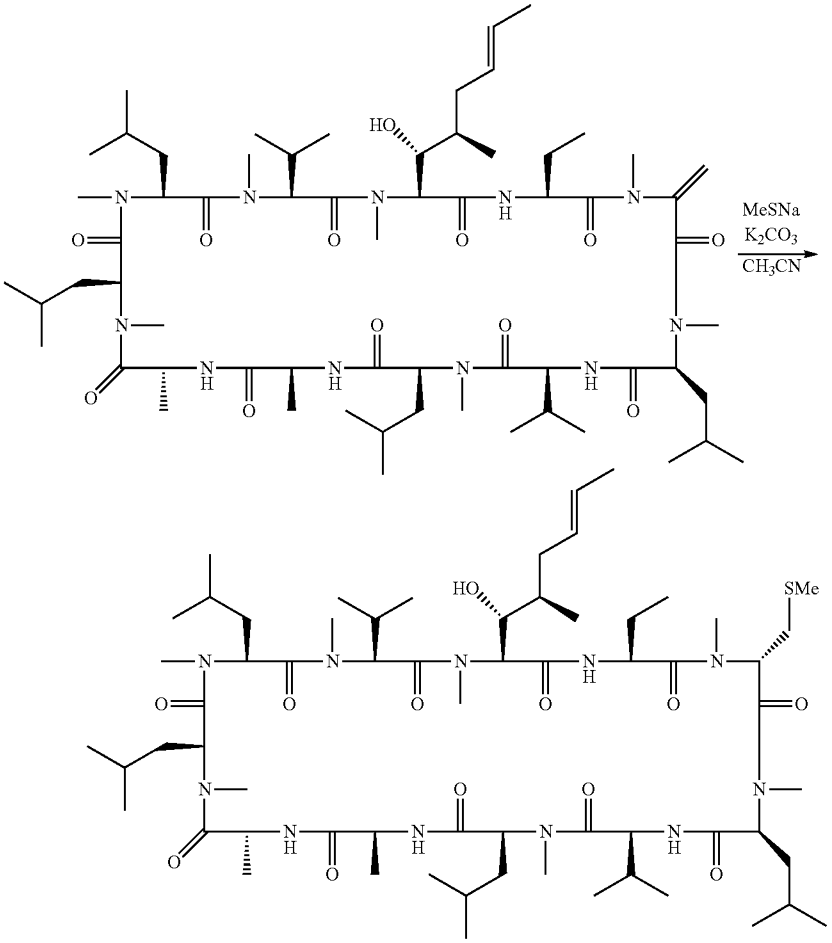
ESMS $MH^+$1262.8, $MNa^+$1284.8
$^1H$ NMR ($CDCl_3$, ppm) δ 2.20 (s, 3H, SMe), 7.18 (d, 1H, amide NH), 7.36 (d, 1H, amide NH), 7.70 (d, 1H, amide NH), 8.15 (d, 1H, amide NH).
Example 5
[(S)-Pentylthiomethyl-Sar][3] cyclosporin A
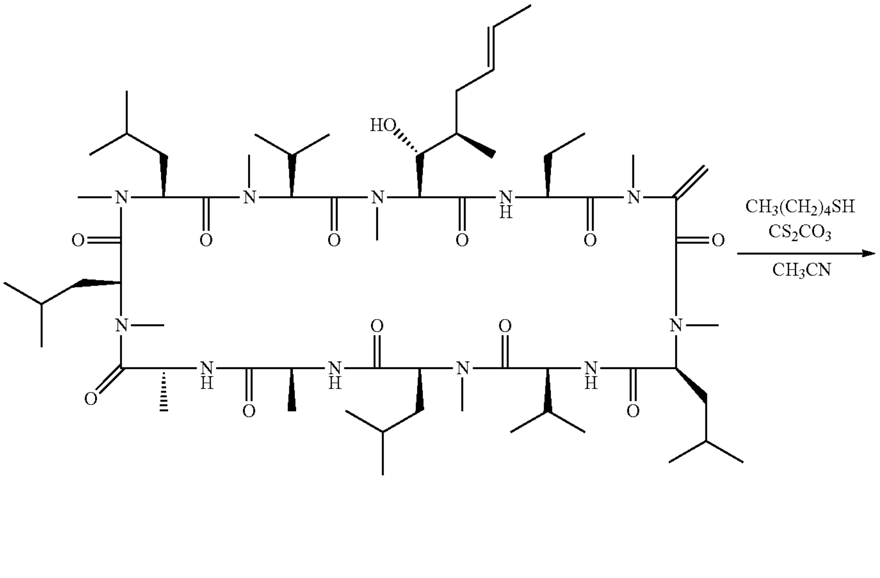

-continued
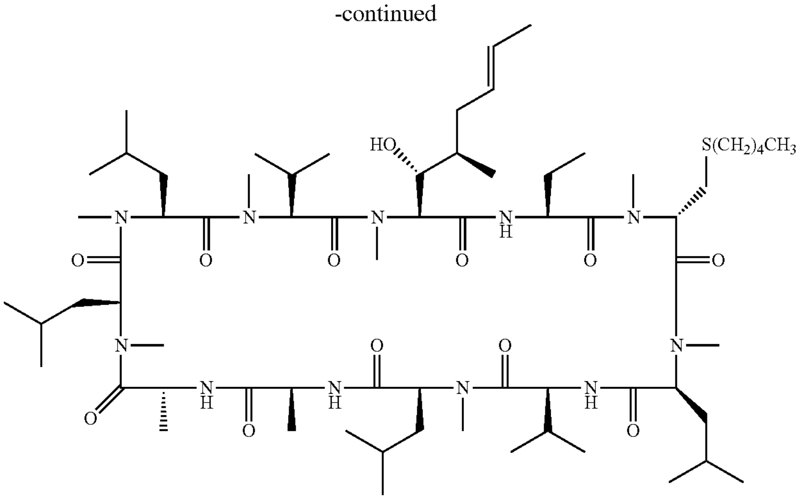
ESMS $MH^+$1318.6, $MNa^+$1340.6
$^1$H NMR ($CDCl_3$, ppm) δ 7.15 (d, 1H, amide NH), 7.37 (d, 1H, amide NH), 7.67 (d, 1H, amide NH), 8.15 (d, 1H, amide NH).
Example 6
[(S)-2-Aminoethylthiomethyl-Sar]$^3$ cyclosporin A
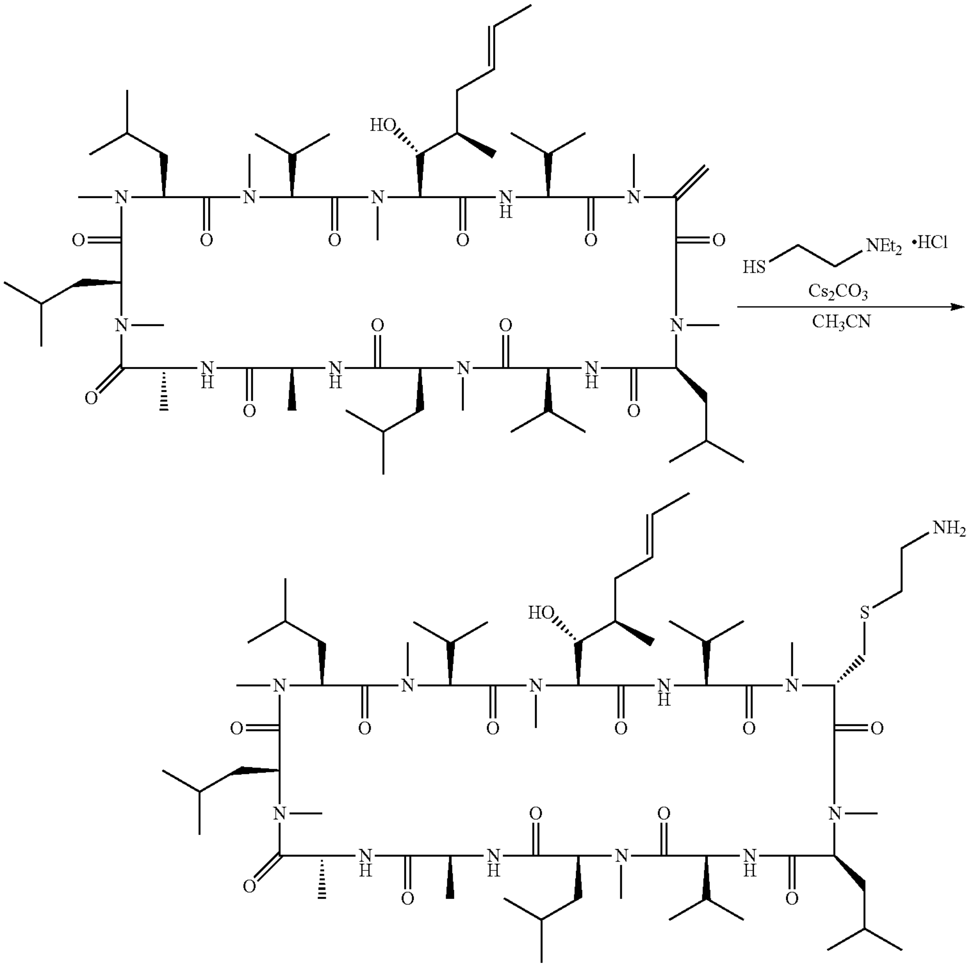

ESMS $MH^+$1291.7
$^1H$ NMR ($CDCl_3$, ppm) δ 7.18 (d, 1H, amide NH), 7.35 (d, 1H, amide NH), 7.67 (d, 1H, amide NH), 8.15 (d, 1H, amide NH).
Example 7
[(S)-{(R)-2-Amino-2-carbomethoxy-ethyl}thiomethyl-Sar]$^3$ cyclosporin A
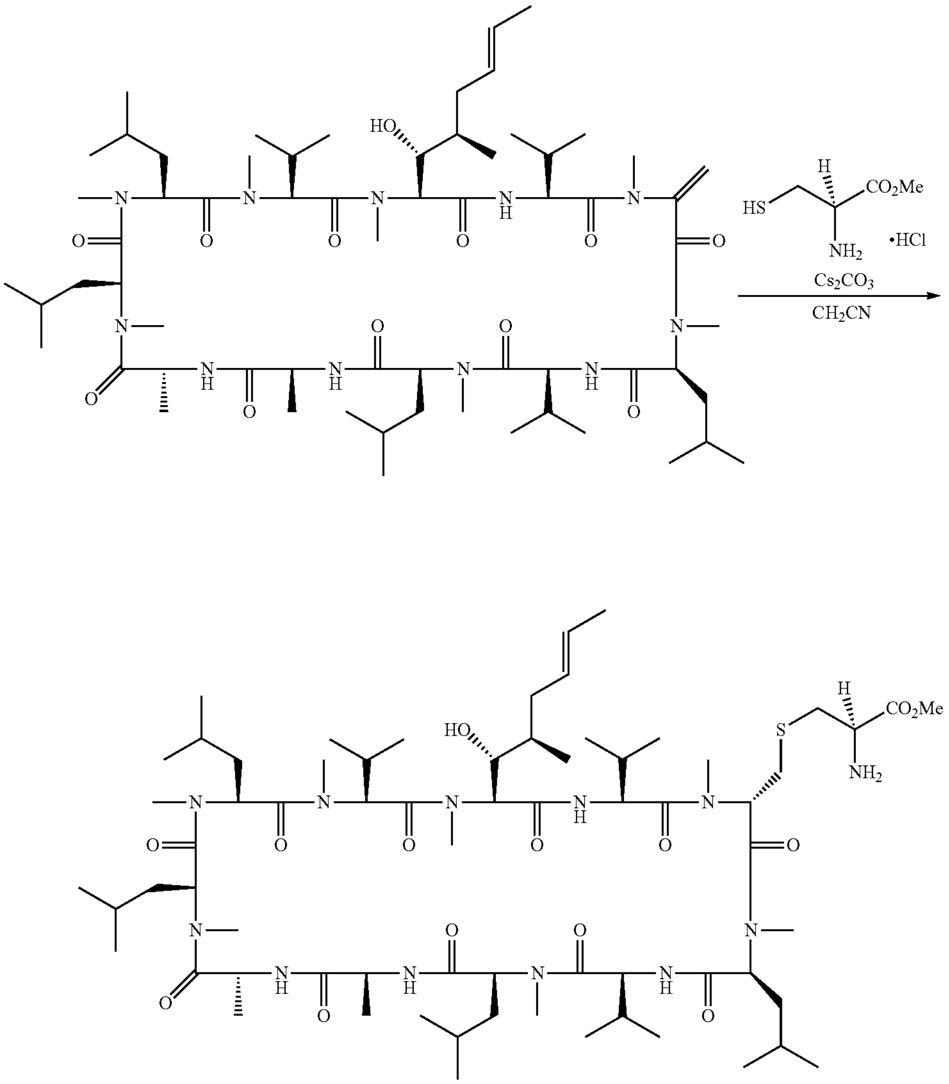
ESMS $MH^+$1349.6
$^1H$ NMR ($CDCl_3$, ppm) δ 3.78 (s, 3H, COOMe), 7.15 (d, 1H, amide NH), 7.33 (d, 1H, amide NH), 7.69 (d, 1H, amide NH), 8.15 (d, 1H, amide NH).

Example 8
[(S)-2-Dimethylaminoethylthiomethyl-Sar]$^3$ cyclosporin A
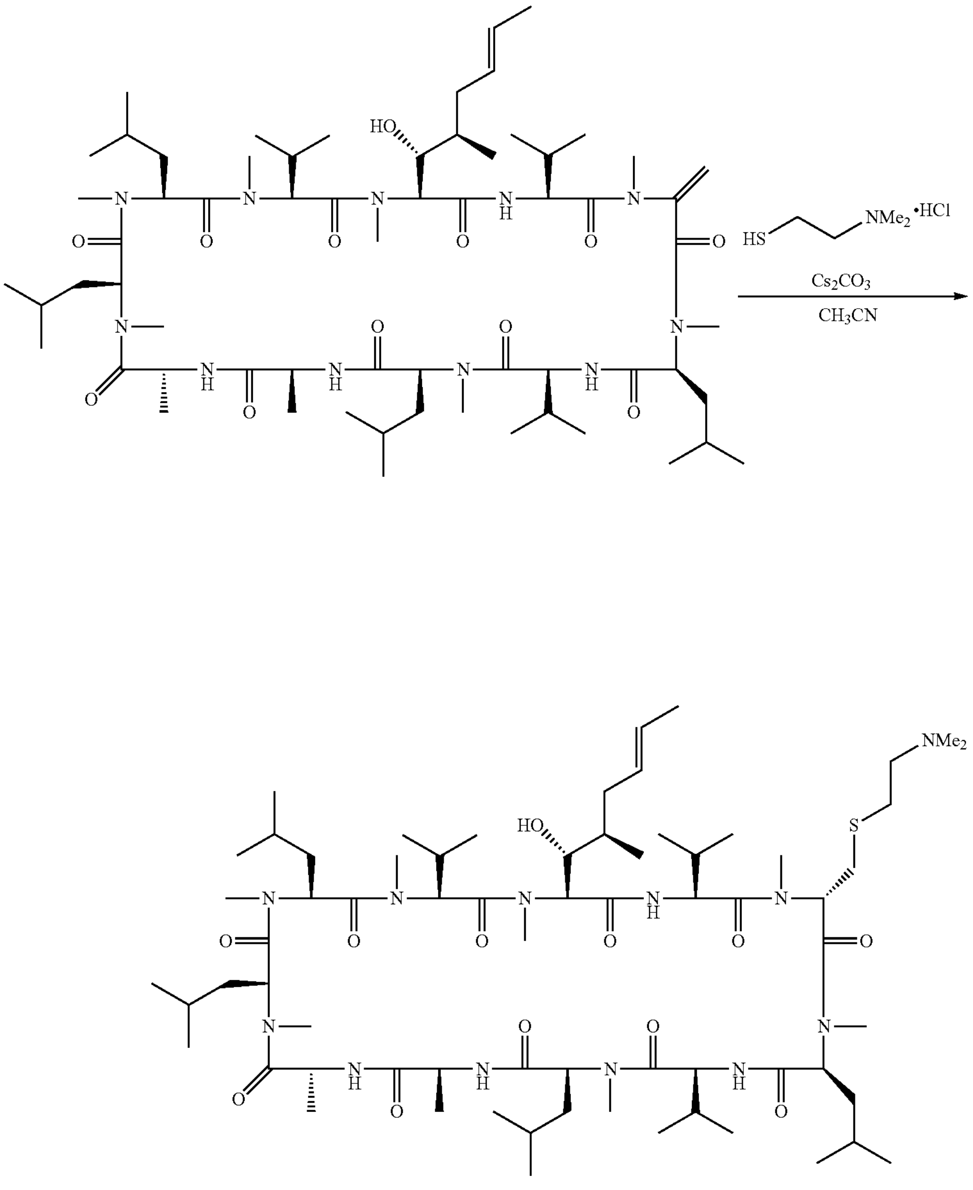
ESMS $MH^+$1319.56
$^1H$ NMR ($CDCl_3$, ppm) δ 2.25 (s, 6H, NMe2), 7.17 (d, 1H, amide NH), 7.35 (d, 1H, amide NH), 7.68 (d, 1H, amide NH), 8.15 (d, 1H, amide NH).

Example 9
[(S)-2-(4-Methylpiperidinyl)thiomethyl-Sar][3] cyclosporin A
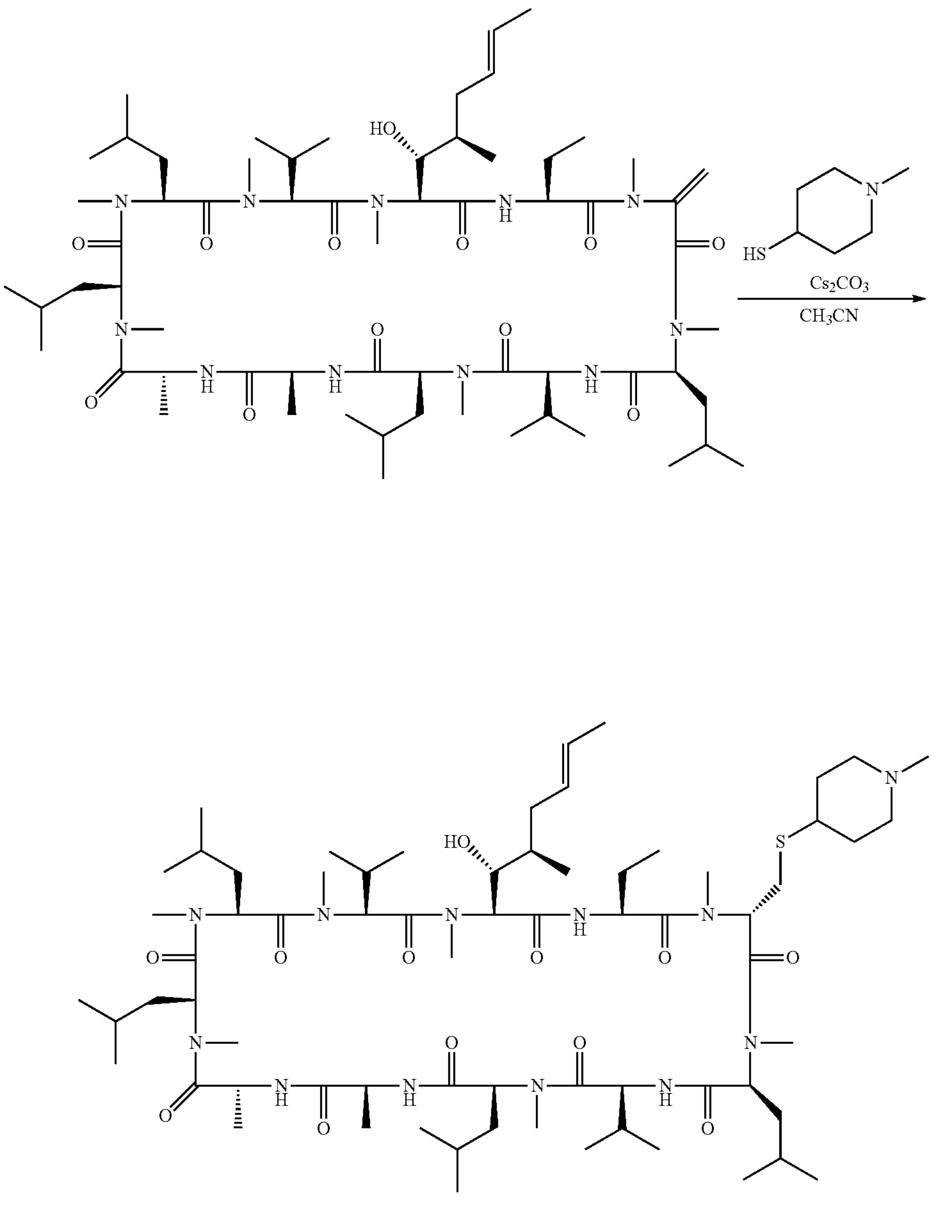
ESMS $MH^+$1345.6
$^1H$ NMR ($CDCl_3$, ppm) δ 2.29 (s, 3H, NMe), 7.17 (d, 1H, amide NH), 7.33 (d, 1H, amide NH), 7.69 (d, 1H, amide NH), 8.17 (d, 1H, amide NH).

Example 10
[(S)-2-(Morpholino)ethylthiomethyl-Sar][3] cyclosporin A
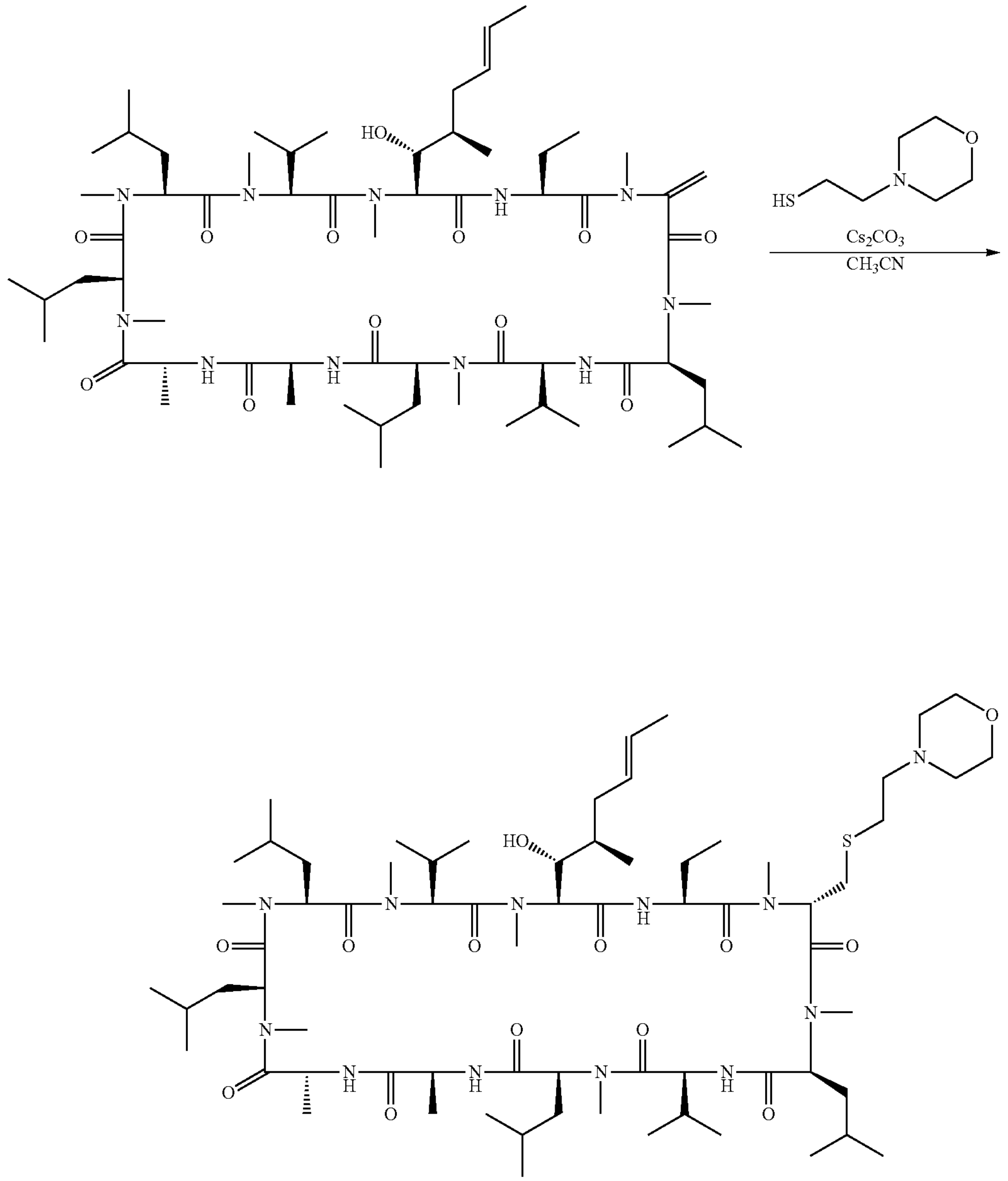
ESMS $MH^+$1361.8
$^1$H NMR ($CDCl_3$, ppm) 7.17 (d, 1H, amide NH), 7.35 (d, 1H, amide NH), 7.69 (d, 1H, amide NH), 8.19 (d, 1H, amide NH).

Example 11
[(S)-Carbomethoxymethylthiomethyl-Sar][3] cyclosporin A
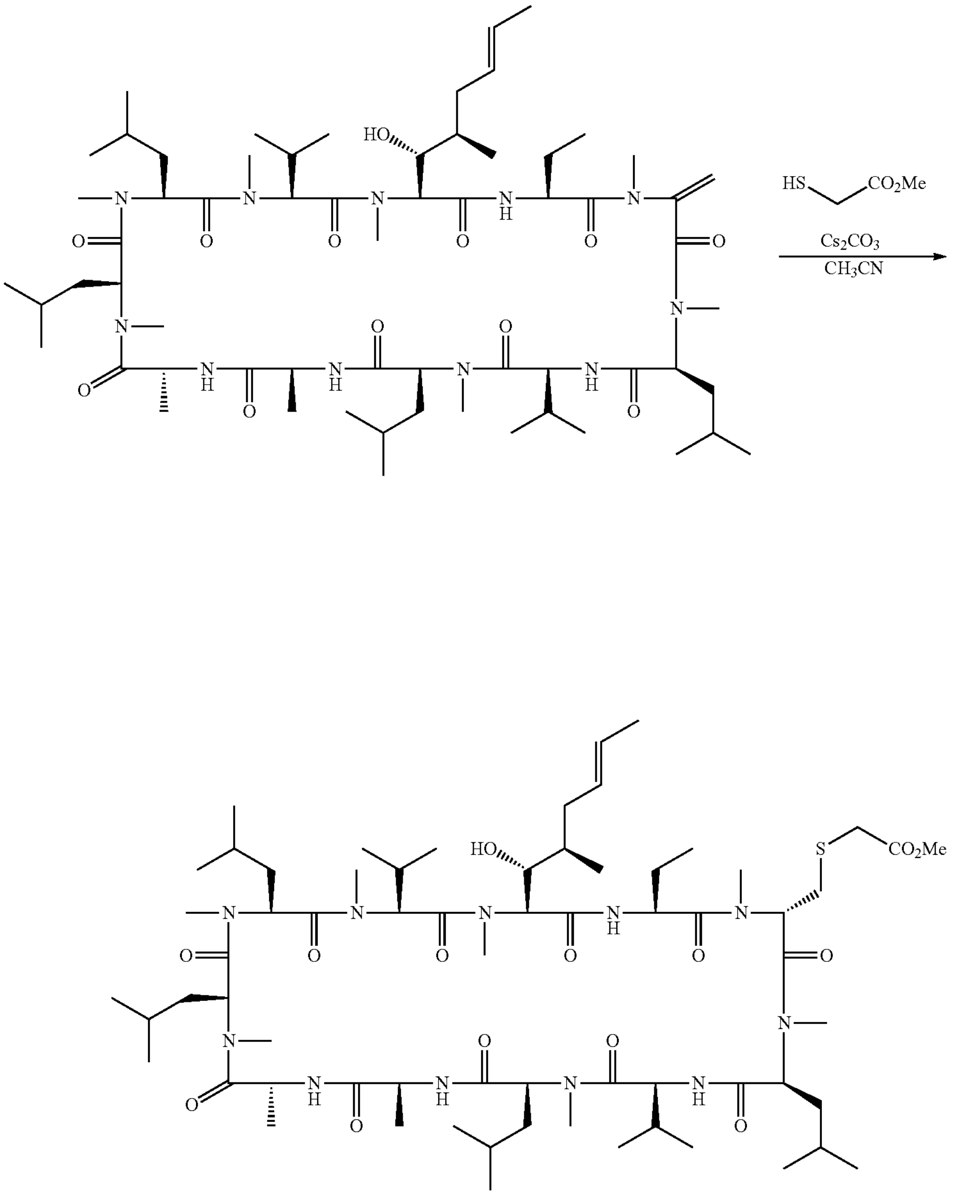
ESMS $MH^+$1320.4
$^1$H NMR ($CDCl_3$, ppm) δ 3.78 (s, 3H, COOMe), 7.17 (d, 1H, amide NH), 7.32 (d, 1H, amide NH), 7.69 (d, 1H, amide NH), 8.15 (d, 1H, amide NH).

Example 12
[(S)-Carbomethoxyethylthiomethyl-Sar]3 cyclosporin A
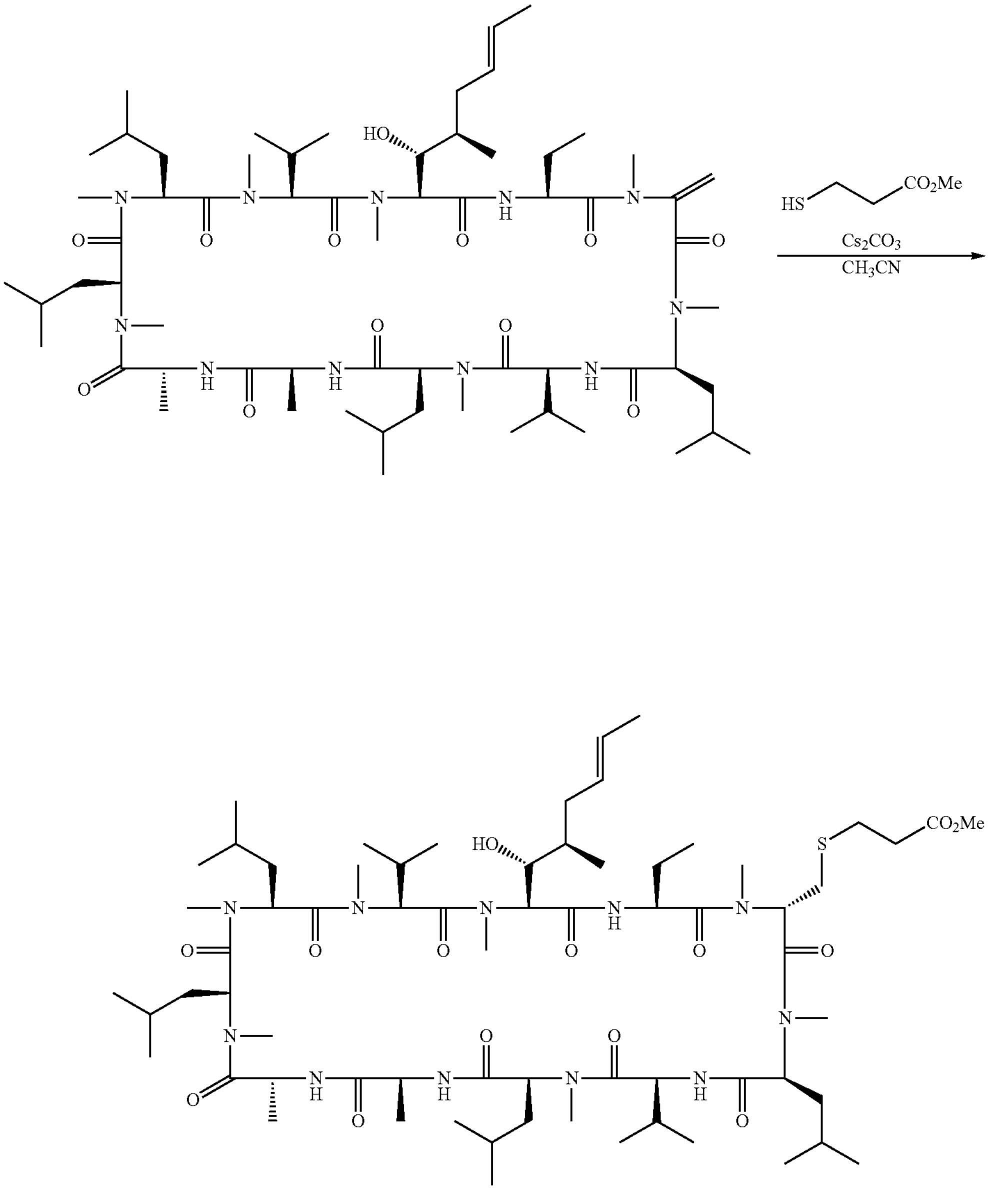
ESMS $MH^+$1335.05
$^1H$ NMR ($CDCl_3$, ppm) δ 3.71 (s, 3H, COOMe), 7.17 (d, 1H, amide NH), 7.34 (d, 1H, amide NH), 7.69 (d, 1H, amide NH), 8.15 (d, 1H, amide NH).

Example 13
[(S)-{(S)-2-Amino-2-carbomethoxy-1,1-dimethyl-ethyl}thiomethyl-Sar]³ cyclosporin A
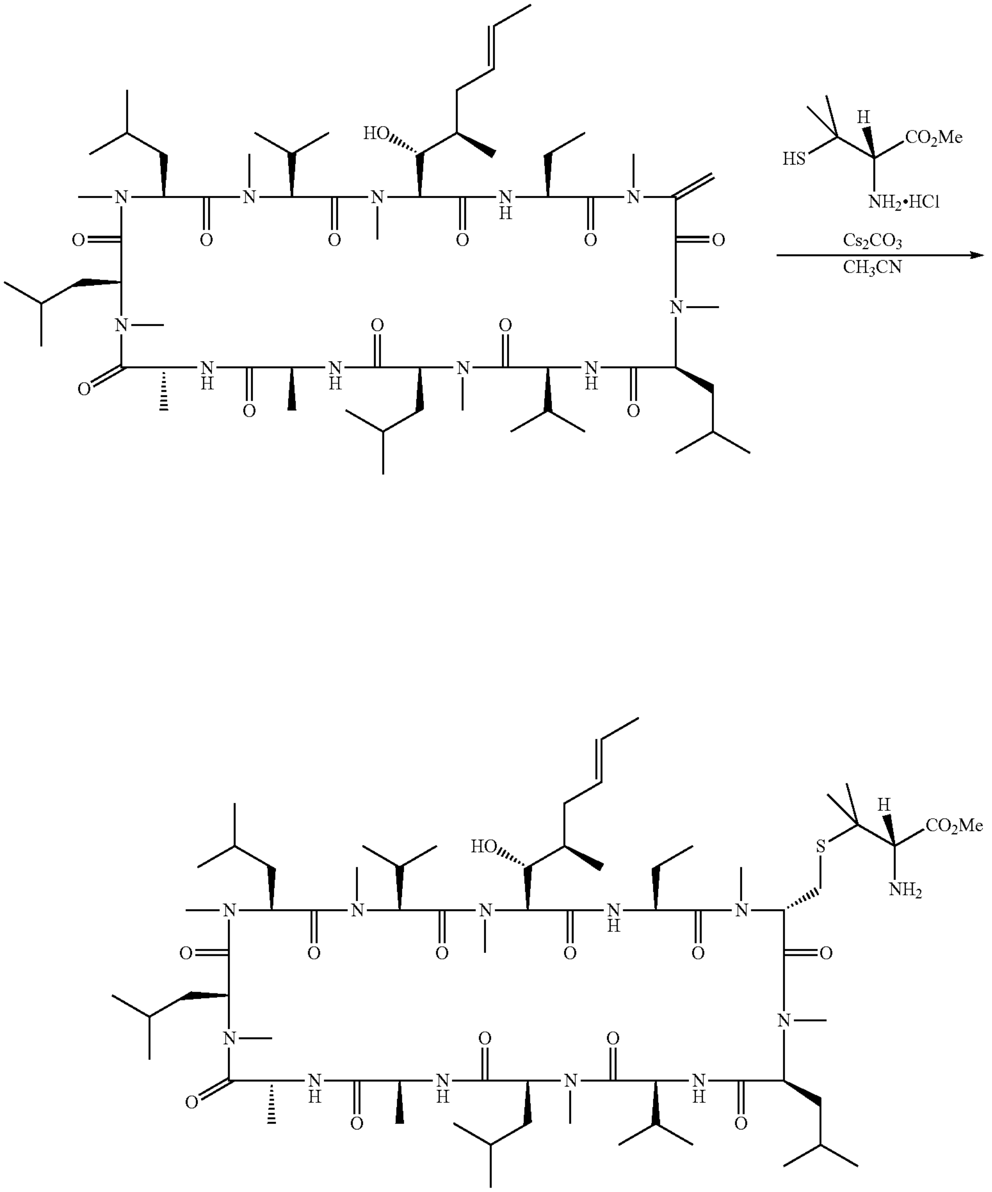
ESMS $MH^+$1377.4
$^1H$ NMR ($CDCl_3$, ppm) δ 3.70 (s, 3H, COOMe), 7.15 (d, 1H, amide NH), 7.33 (d, 1H, amide NH), 7.68 (d, 1H, amide NH), 8.08 (d, 1H, amide NH).

[(S)-2-(N-imidazolyl)ethylthiomethyl-Sar][3]
cyclosporin A
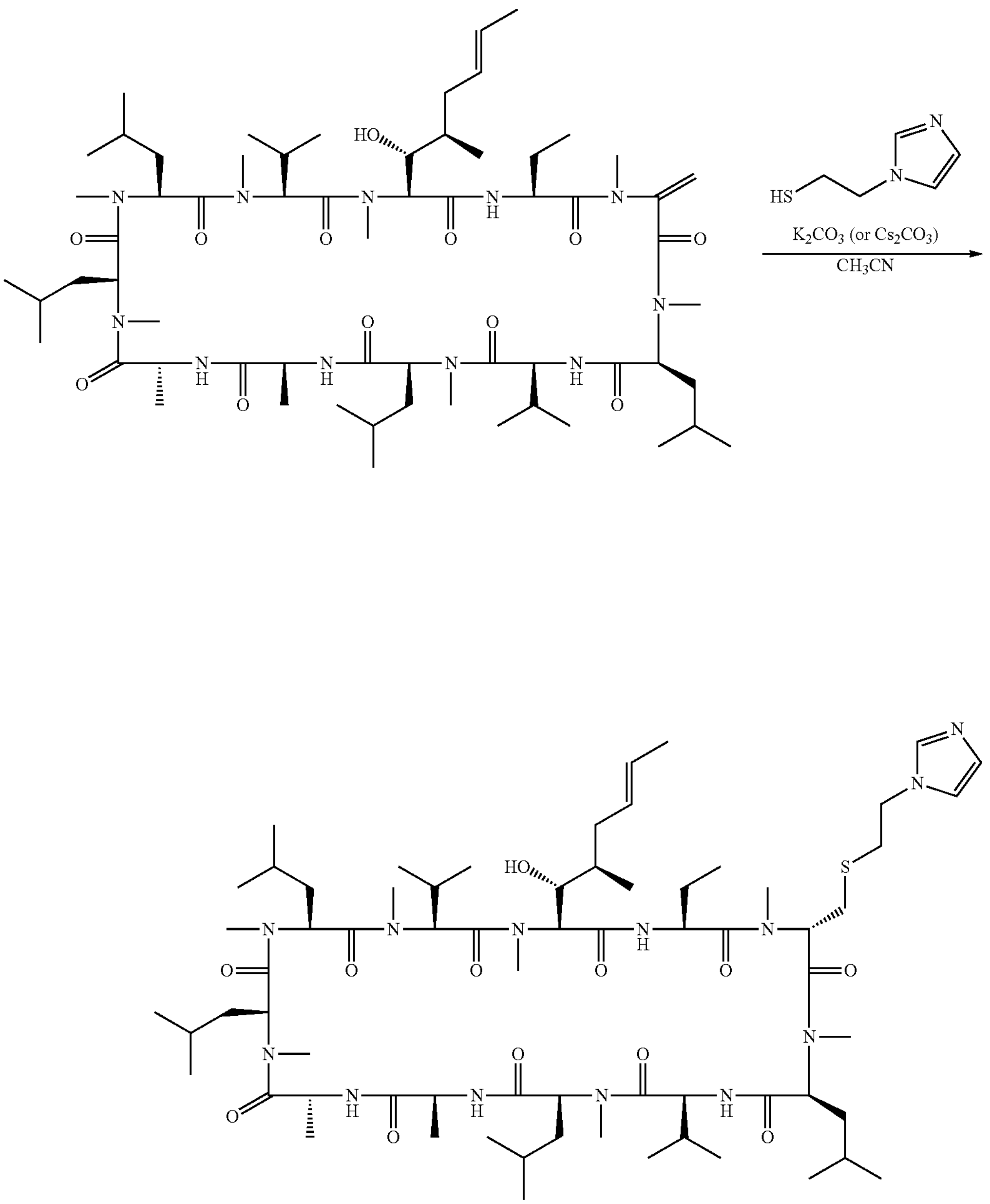
ESMS $MH^+$1342.7
$^1$H NMR ($CDCl_3$, ppm) δ6.89 (s, 1H, imidazole), 7.00 (s, 1H, imidazole), 7.10 (d, 1H, amide NH), 7.24 (d, 1H, amide NH), 7.48 (s, 1H, imidazole), 7.60 (d, 1H, amide NH), 8.11 (d, 1H, amide NH).

[(S)-2-(N-pyrazolyl)ethylthiomethyl-Sar][3] cyclosporin A
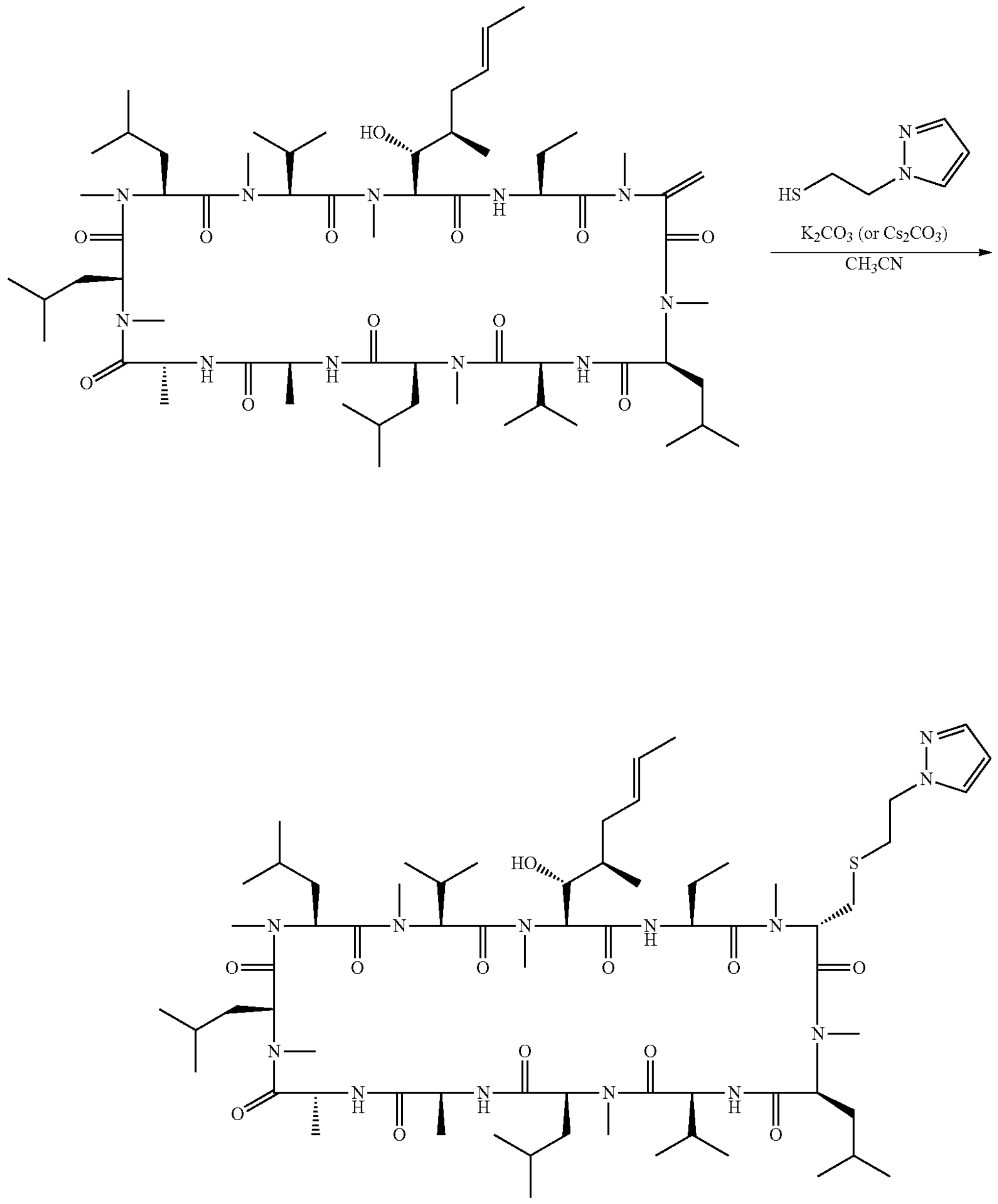
ESMS $MH^+$1342.9
$^1$H NMR ($CDCl_3$, ppm) 66.26 (dd, 1H, pyrazole), 7.17 (d, 1H, amide NH), 7.31 (d, 1H, amide NH), 7.46 (d, 1H, pyrazole), 7.51 (d, 1H, pyrazole), 7.70 (d, 1H, amide NH), 8.11 (d, 1H, amide NH).

[(S)-2-Diethylamino-1,1-dimethyl-ethylthiomethyl-Sar]$^3$ cyclosporin A
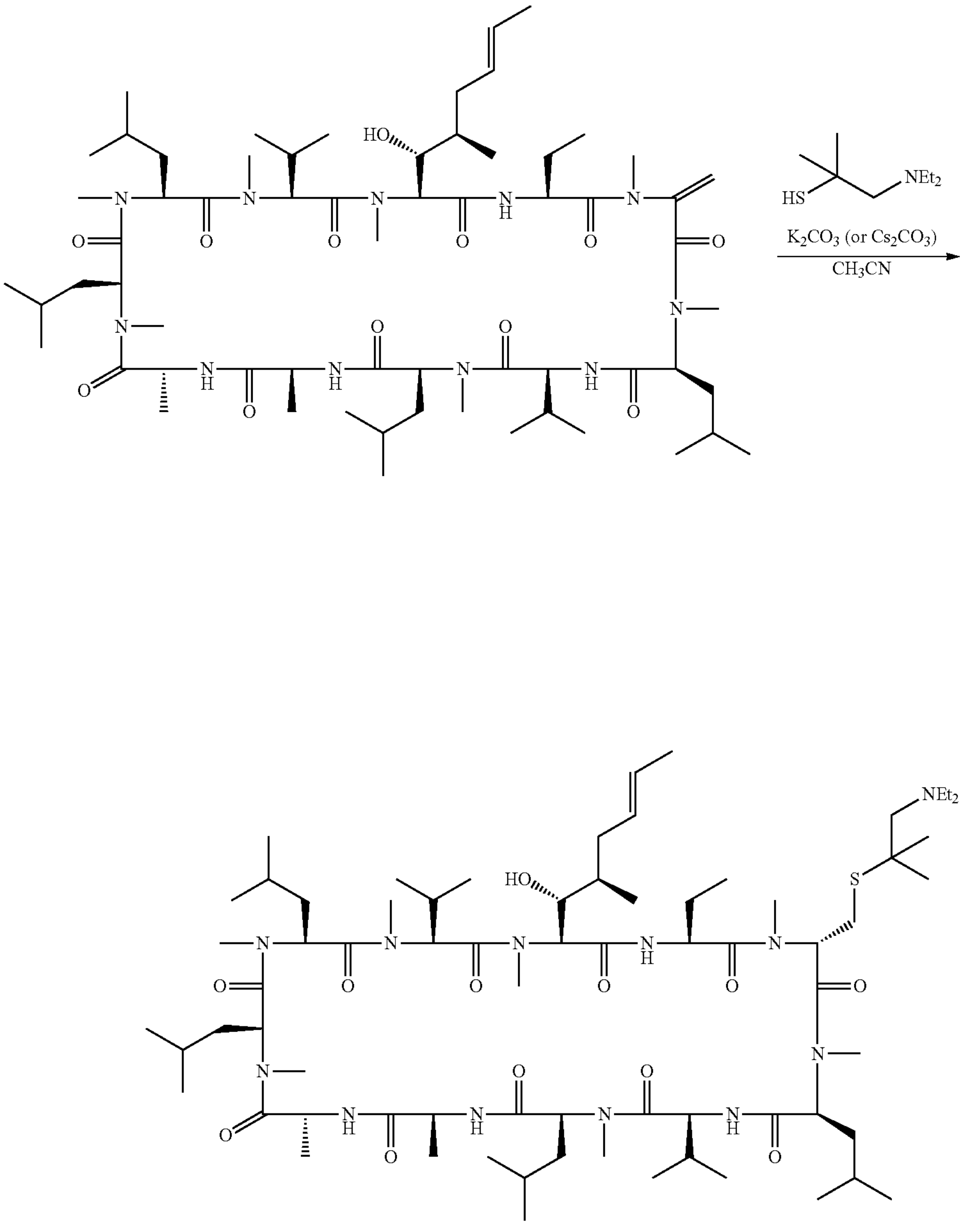
ESMS $MH^+$1375.9
$^1$H NMR ($CDCl_3$, ppm) 67.16 (1H, d, amide NH), 7.39 (1H, d, amide NH), 7.68 (1H, d, amide NH), 8.11 (1H, d, amide NH).

[(S)-2-Morpholino-1,1-dimethyl-ethylthiomethyl-Sar][3] cyclosporin A
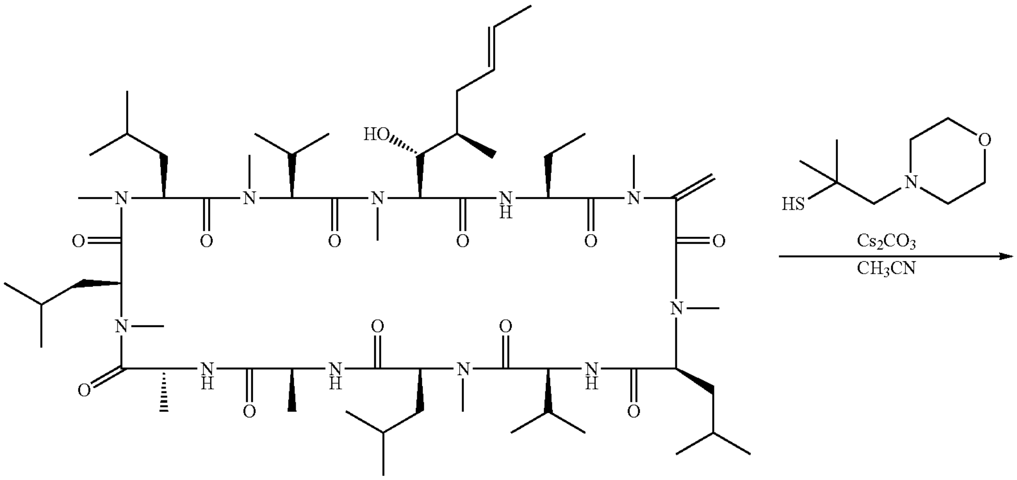
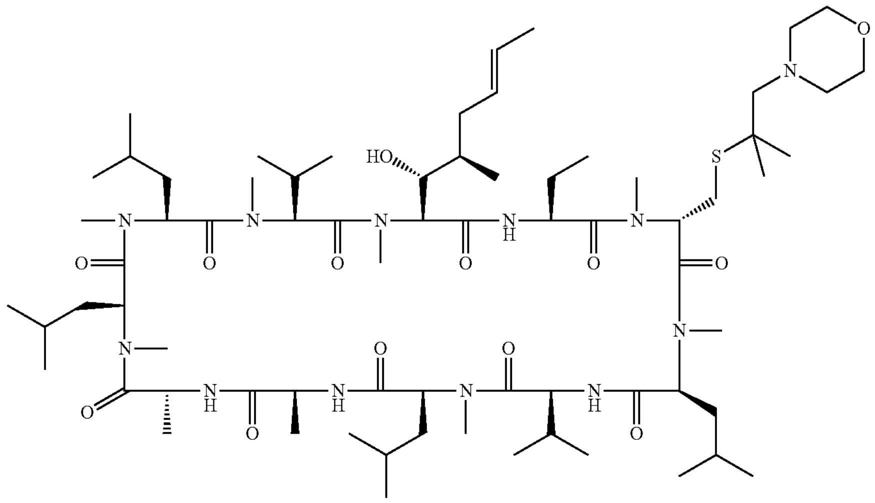
ESMS MH+1389.6
$^1$H NMR ($CDCl_3$, ppm) δ 7.18 (d, 1H, amide NH), 7.38 (d, 1H, amide NH), 7.69 (d, 1H, amide NH), 8.14 (d, 1H, amide NH).

[(S)-3-Diethylaminopropylthiomethyl-Sar][3] cyclosporin A
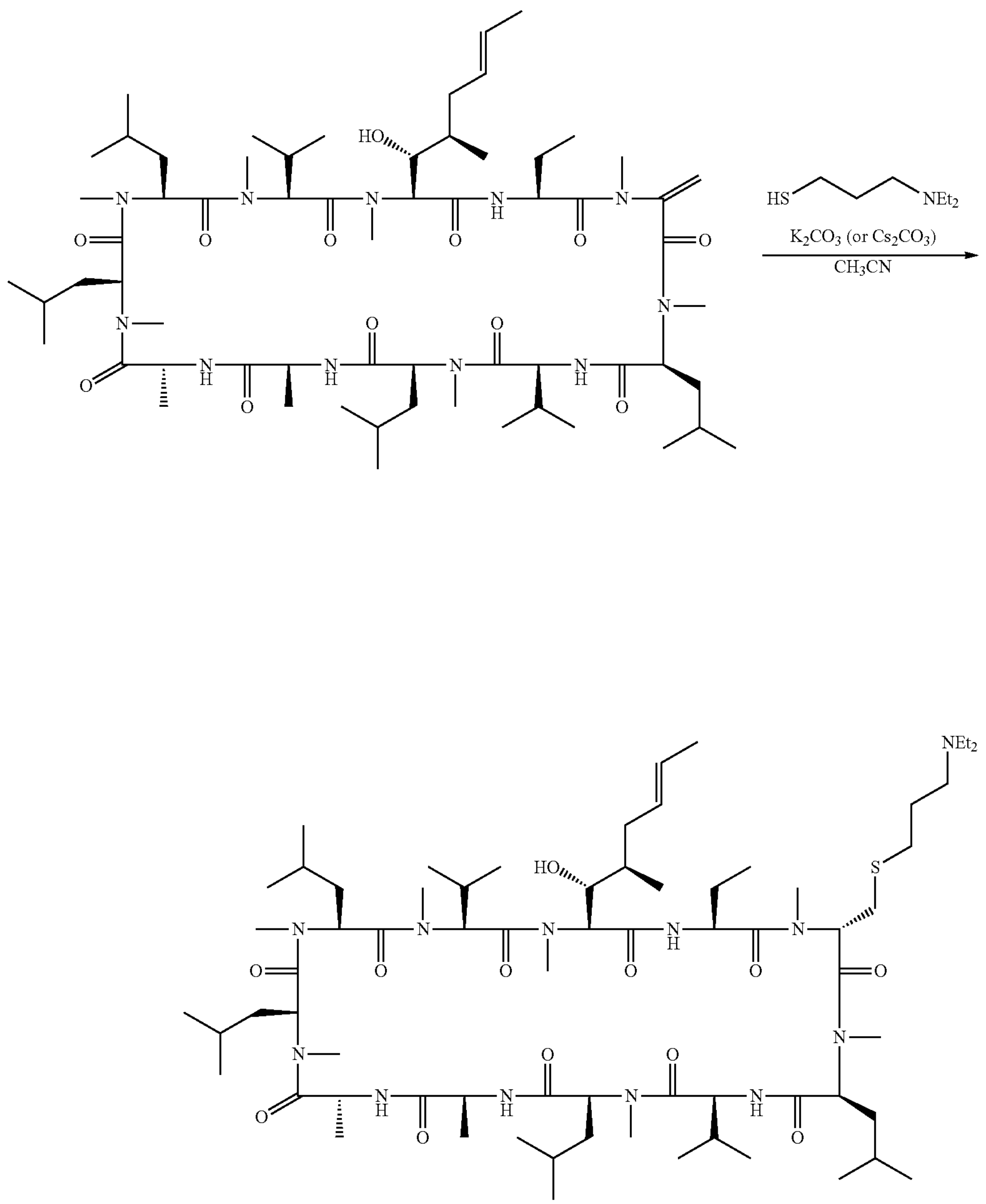
ESMS $MH^+$1362.0
$^1$H NMR ($CDCl_3$, ppm) 67.19 (1H, d, amide NH), 7.37 (1H, d, amide NH), 7.68 (1H, d, amide NH), 8.13 (1H, d, amide NH).

[(S)-3-(Morpholino)-propylthiomethyl-Sar][3] cyclosporin A
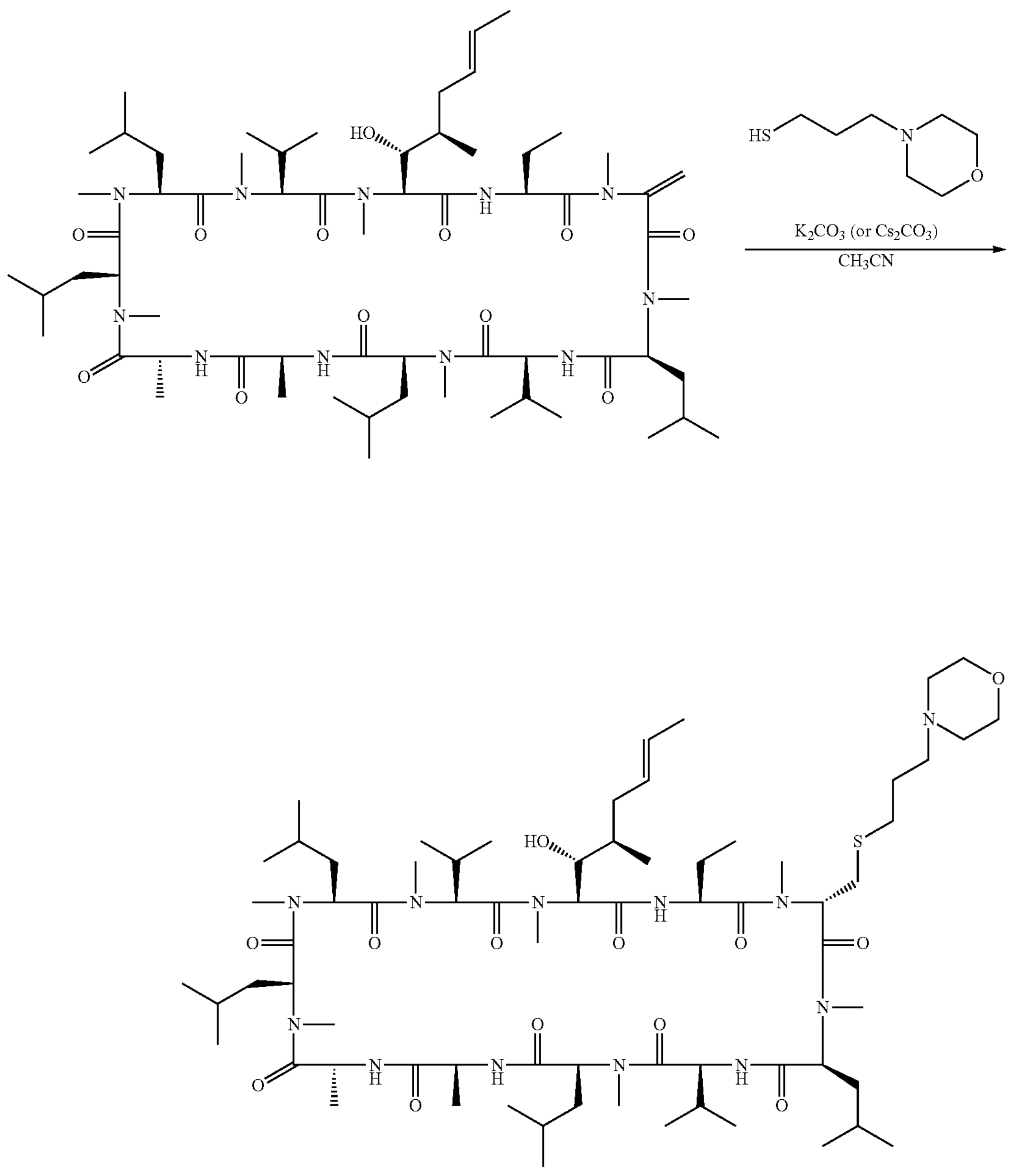
ESMS $MH^+$1375.7
$^1$H NMR ($CDCl_3$, ppm) 67.18 (1H, d, amide NH), 7.33 (1H, d, amide NH), 7.70 (1H, d, amide NH), 8.16 (1H, d, amide NH).

[(S)-Mercaptomethyl-Sar][3] cyclosporin A
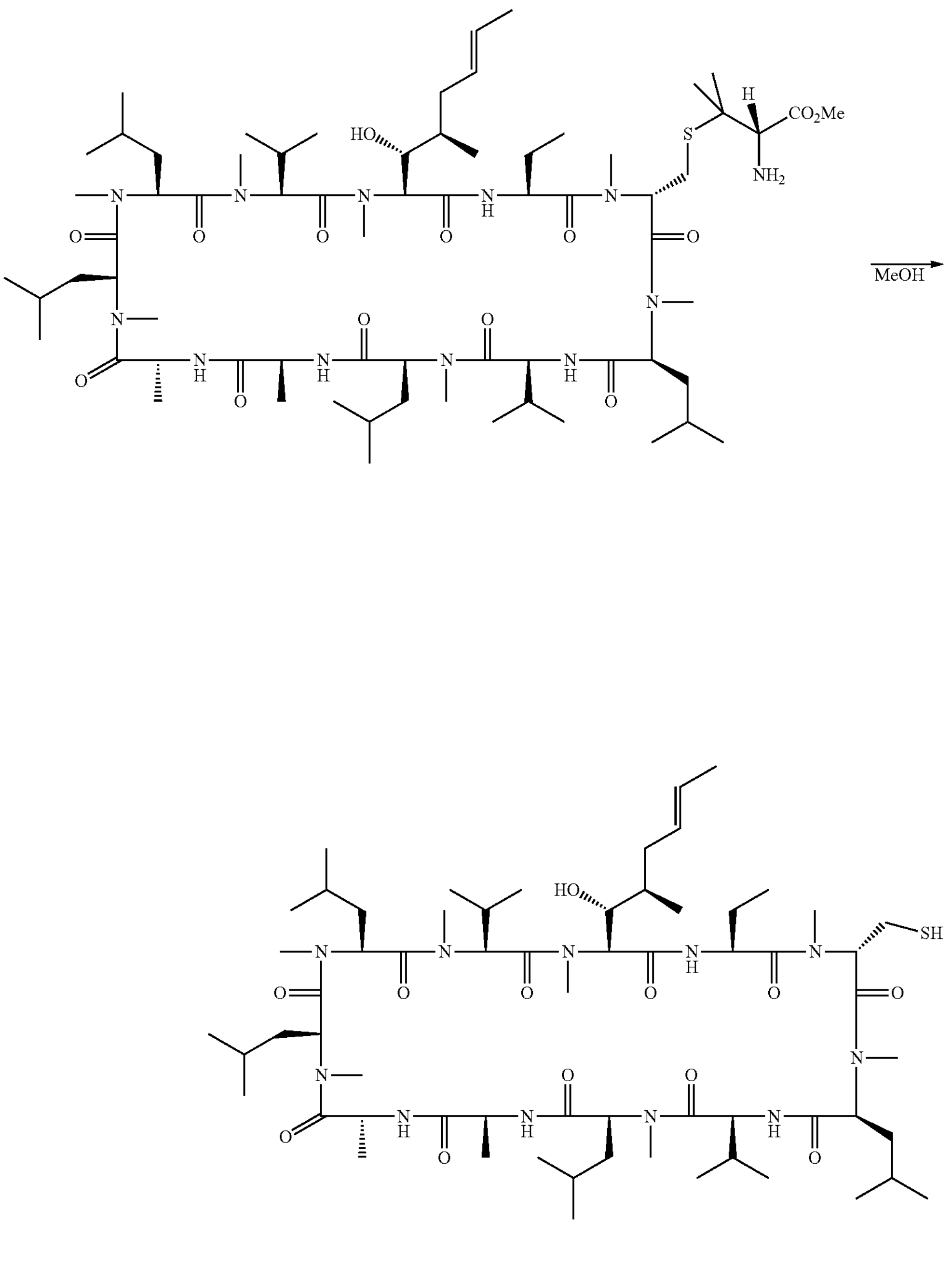
A solution of [(S)-{(S)-2-amino-2-carbomethoxy-1,1-dimethyl-ethyl}thiomethyl-Sar][3] cyclosporinA (0.028 g, 0.02 mmol) in methanol (3 ml) was heated to 50° C. for nineteen days. The reaction mixture was purified with SCX column/methanol to give [(S)-mercaptomethyl-Sar][3] cyclosporinA.
ESMS $MH^+$1247.9
$^1H$ NMR ($CDCl_3$, ppm) δ 7.20 (d, 1H, amide NH), 7.26 (d, 1H, amide NH), 7.70 (d, 1H, amide NH), 8.24 (d, 1H, amide NH).

[(S)-Allylthiomethyl-Sar][3] cyclosporin A

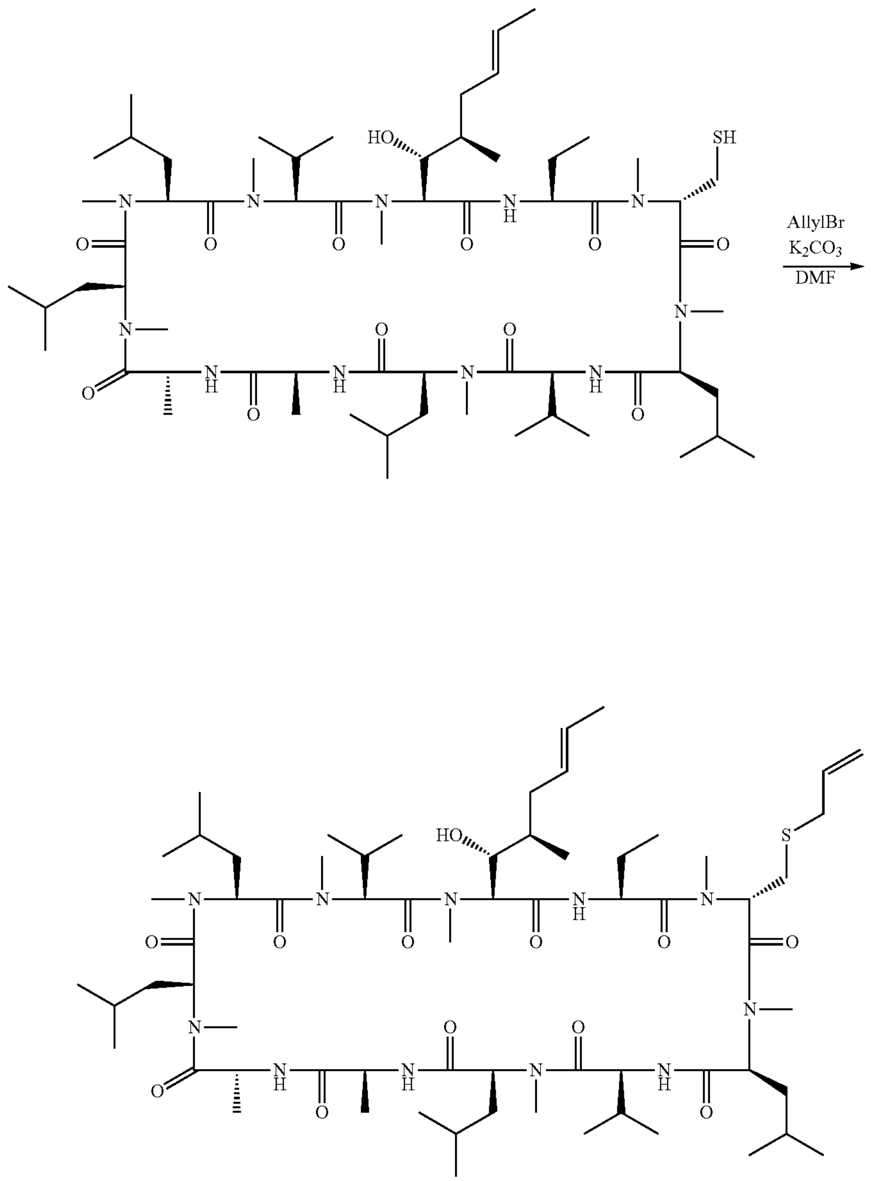

To a solution of [(S)-mercaptomethyl-Sar][3] cyclosporinA (0.074 g, 0.06 mmol) in dimethylformamide (1.5 ml) was added potassium carbonate (0.021 g, 0.15 mmol) and allyl bromide (0.036 g, 0.3 mmol). The suspension was stirred at room temperature overnight then an additional amount of potassium carbonate (0.021 g, 0.15 mmol) and allyl bromide (0.036 g, 0.3 mmol) were added and the reaction mixture stirred over 2 days. The reaction mixture was concentrated, the residue ultrasonicated in the presence of dichloromethane then filtrated. The dichloromethane was evaporated and the residue purified by MPLC chromatography using a solvent gradient of 100% dichloromethane 95% dichloromethane/5% methanol to give [(S)-Allylthiomethyl-Sar][3] cyclosporinA.

ESMS $MH^+$1288.6

$^1H$ NMR ($CDCl_3$, ppm) δ 7.18 (d, 1H, amide NH), 7.35 (d, 1H, amide NH), 7.70 (d, 1H, amide NH), 8.13 (d, 1H, amide NH).

Example 14

[(S)-{(R)-2-Amino-2-carbohydroxy-ethyl}thiomethyl-Sar]$^3$ cyclosporin A

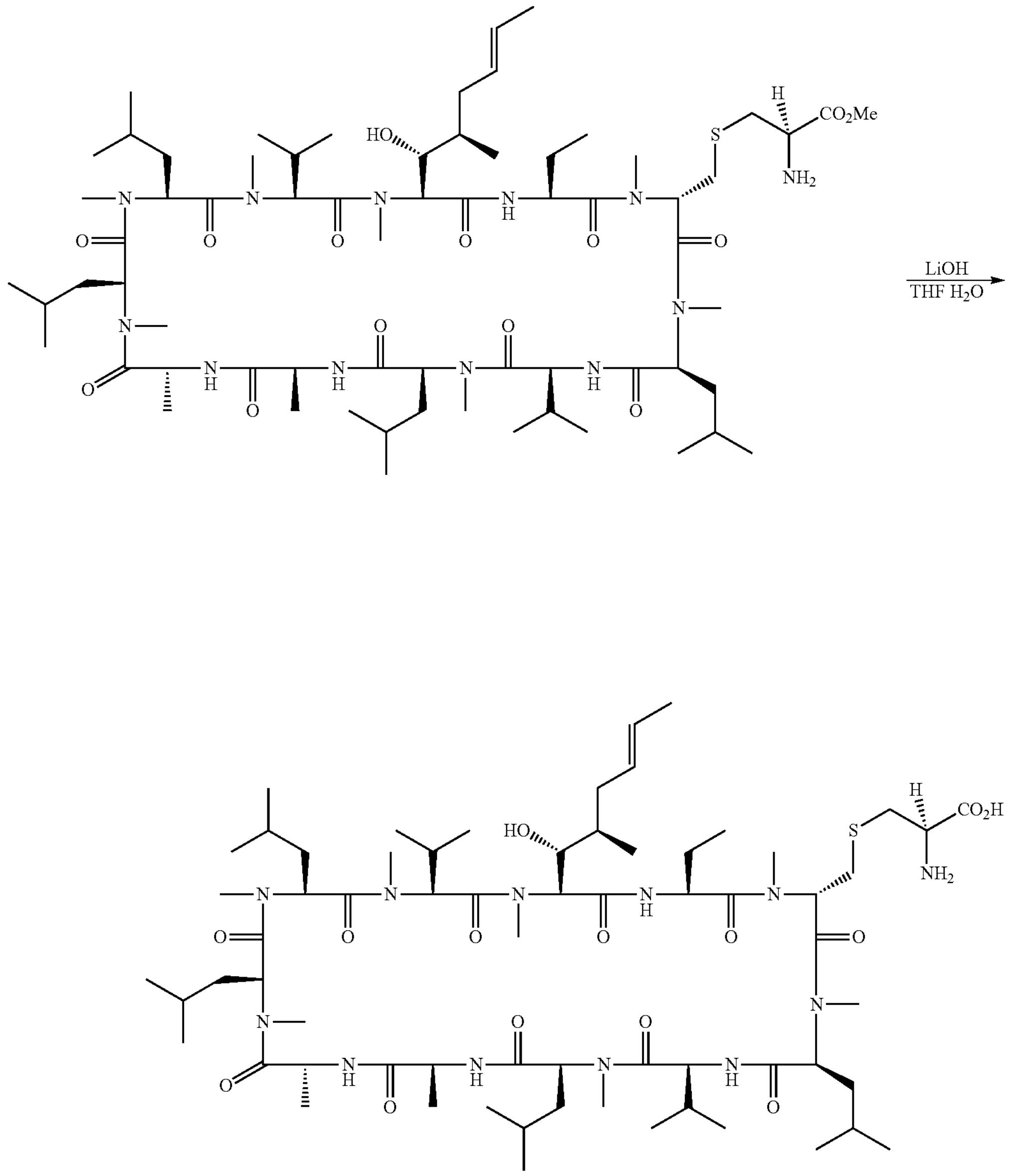

To a solution of [(S)-{(R)-2-amino-2-carbomethoxy-ethyl}thiomethyl-Sar]$^3$ cyclosporinA (0.033 g, 0.024 mmol) in tetrahydrofuran (2 ml) was added a solution of lithium hydroxide monohydrate (0.0043 g, 0.098 mmol) in water (0.3 ml). The solution was stirred at room temperature for 3 hours. Hydrochloric acid (2N, 0.05 ml) was added then the reaction mixture was concentrated. Purification by SCX column using a gradient 0.035M ammonia in methanol to 0.175M ammonia in methanol provided 20 mg of [(S)-{(R)-2-Amino-2-carbohydroxy-ethyl}thiomethyl-Sar]$^3$ cyclosporinA.

ESMS $MH^+$1335.7

$^1H$ NMR ($CDCl_3$, ppm) δ 7.19 (d, 1H, amide NH), 7.32 (d, 1H, amide NH), 7.69 (d, 1H, amide NH), 8.2 (d, 1H, amide NH).

In a similar way the following compounds were prepared:
Example 15
[(S)-Carbohydroxymethylthiomethyl-Sar][3] cyclosporin A
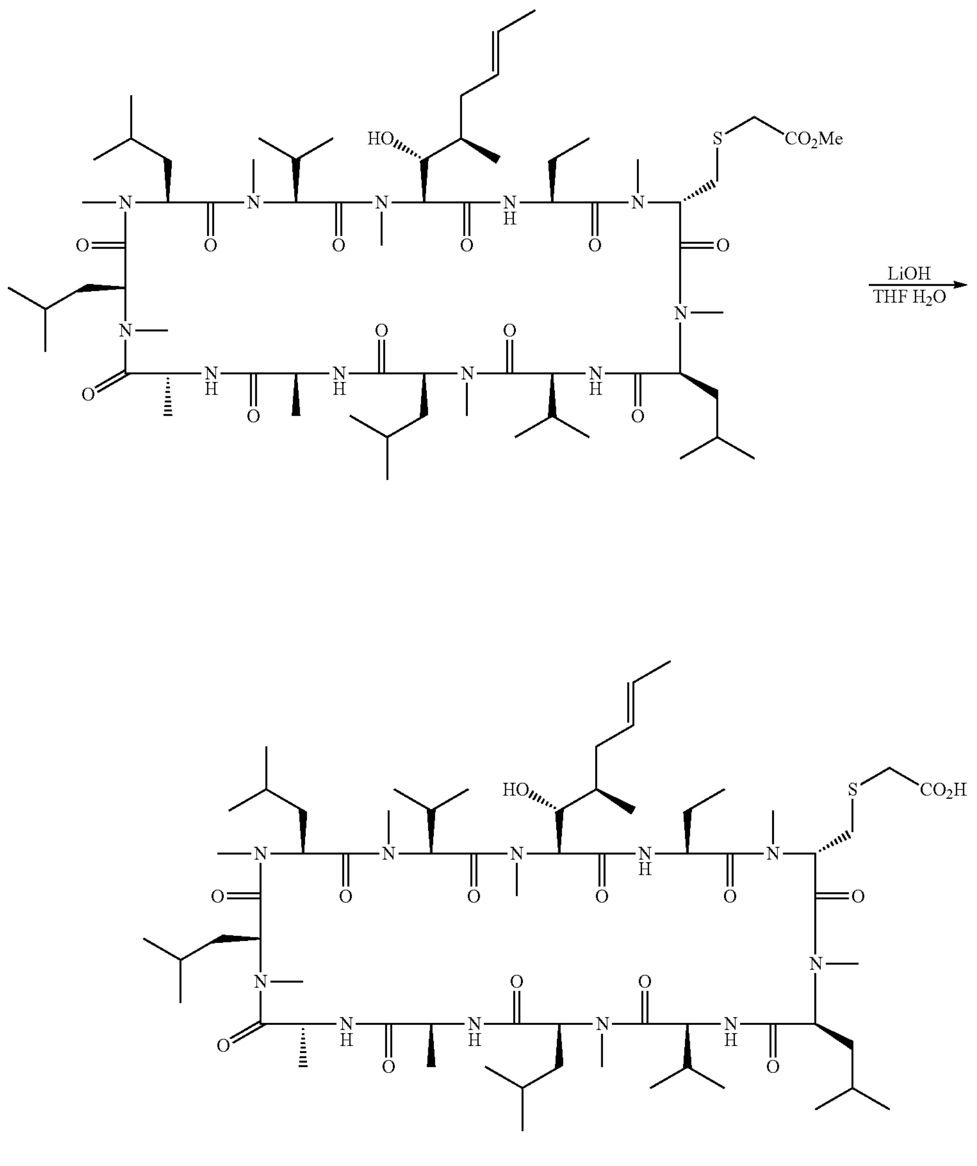
ESMS $MH^+$1306.6
$^1H$ NMR ($CDCl_3$, ppm) δ 7.18 (d, 1H, amide NH), 7.35 (d, 1H, amide NH), 7.70 (d, 1H, amide NH), 8.17 (d, 1H, amide NH).

Example 16
[(S)-{(S)-2-Amino-2-carbohydroxy-1,1-dimethyl-ethyl}thiomethyl-Sar]$^3$ cyclosporin A
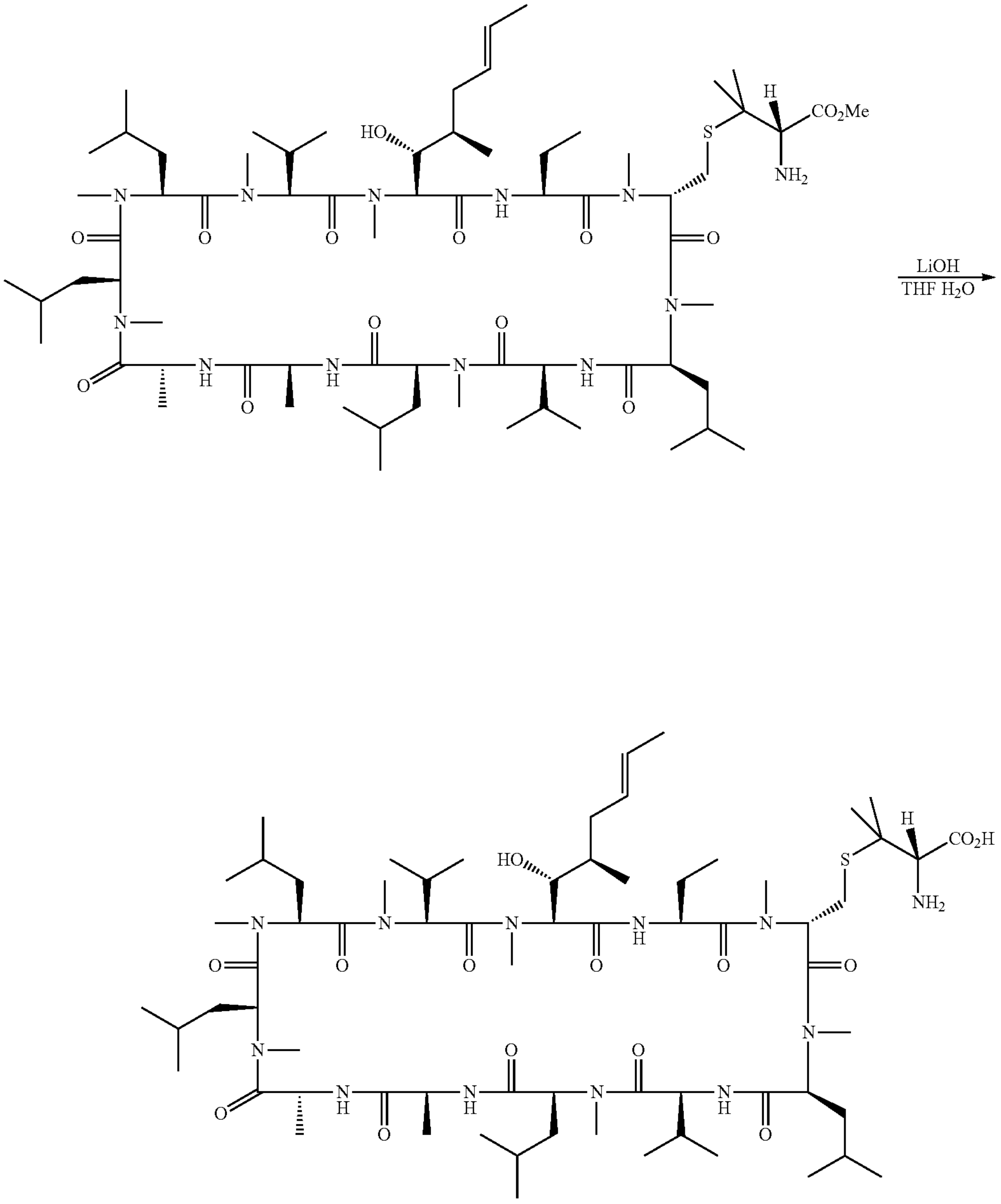
ESMS $MH^+$1363.5
$^1$H NMR ($CDCl_3$, ppm) δ 7.17 (d, 1H, amide NH), 7.30 (d, 1H, amide NH), 7.68 (d, 1H, amide NH), 8.18 (d, 1H, amide NH).

Example 17
[(S)-Carbohydroxyethylthiomethyl-Sar]$^3$ cyclosporin A
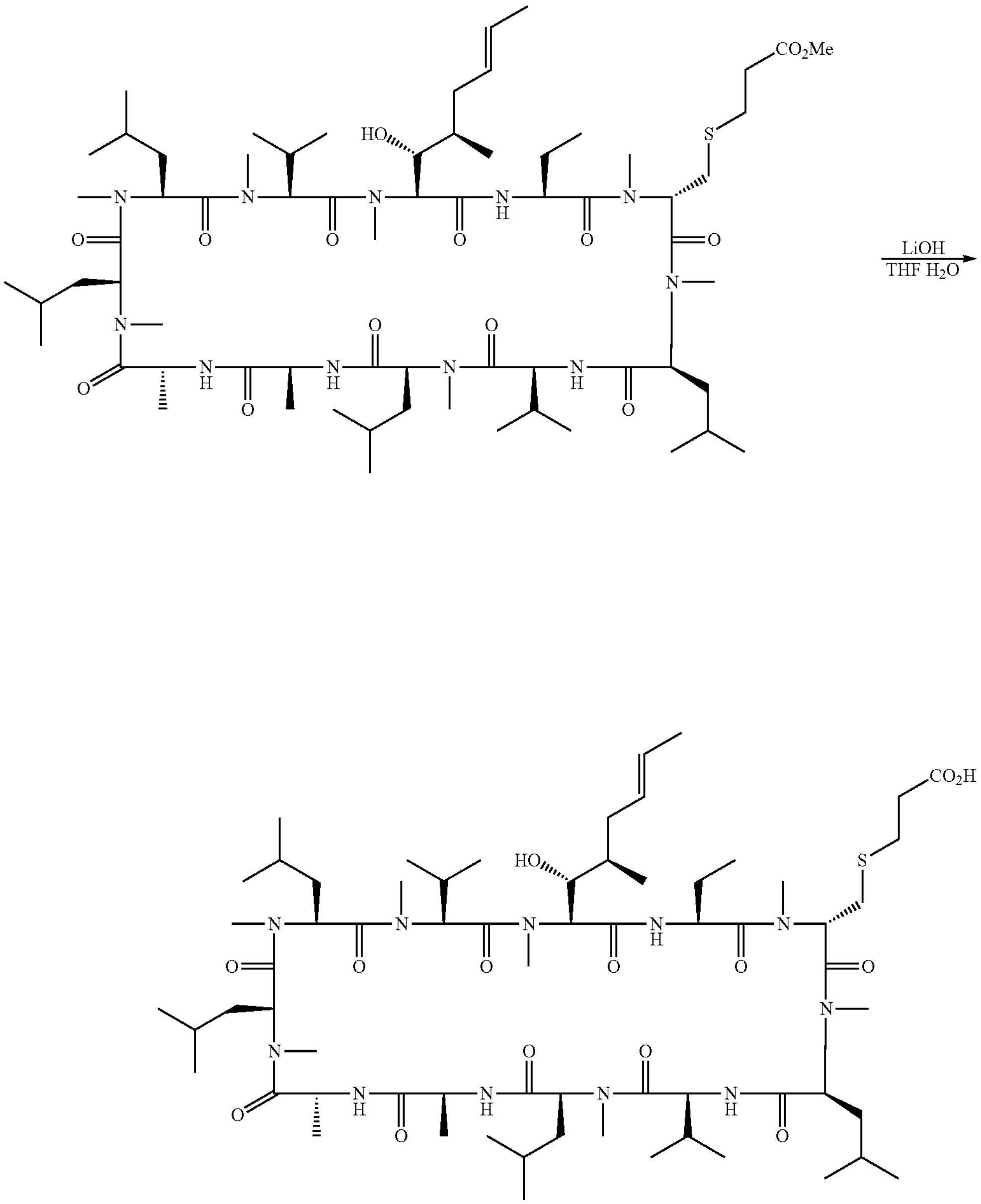
ESMS $MH^+$1320.6
$^1H$ NMR ($CDCl_3$, ppm) δ 7.20 (d, 1H, amide NH), 7.36 (d, 1H, amide NH), 7.70 (d, 1H, amide NH), 8.18 (d, 1H, amide NH).

Example 18

[(S)-2-Isopropylaminoethylthiomethyl-Sar]$^3$ cyclosporin A

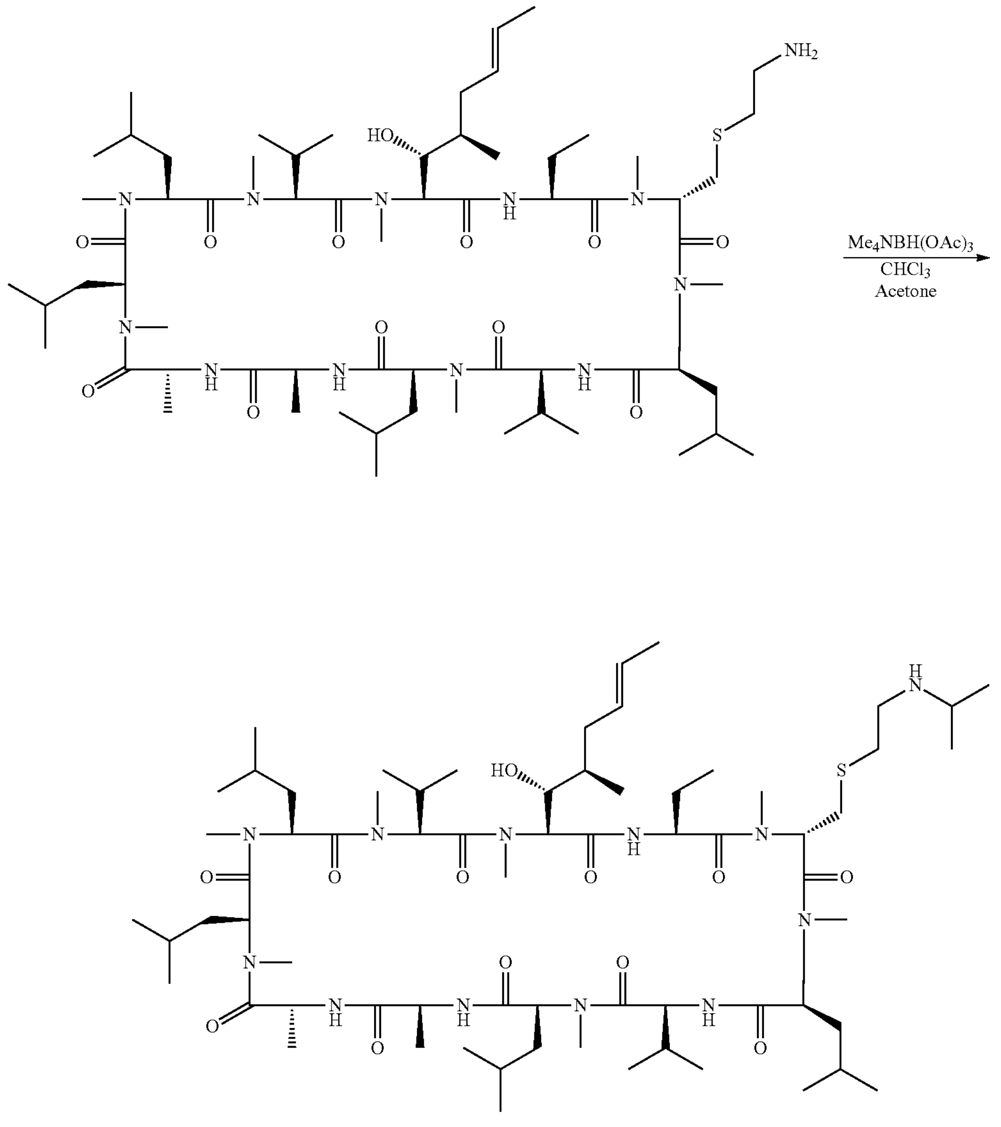

To a solution of [(S)-2-aminoethylthiomethyl-Sar]$^3$ cyclosporinA (0.129 g, 0.1 mmol) in chloroform (2 ml) and acetone (0.1 ml) was added tetramethylammonium triacetoxy borohydride (0.066 mg, 0.25 mmol) and the reaction mixture was stirred at room temperature for 17 hours. The reaction mixture was partitioned between dichloromethane and water. The organic phase was washed with brine, dried ($Na_2SO_4$) and concentrated to give a white solid. Purification by MPLC chromatography using a solvent gradient of 100% diethyl ether 95% diethyl ether/5% methanol then 100% diethyl ether followed by a second solvent gradient 100% diethyl ether 96% diethyl ether/4% methanol containing 10% aqueous ammonia (0.88) gave [(S)-2-isopropylaminoethylthiomethyl-Sar]$^3$ cyclosporinA.

ESMS $MH^+$1333.0

$^1H$ NMR ($CDCl_3$, ppm) δ 1.05 (d, 6H, 2×$CH_3$), 2.84 (m, 1H, CH), 7.18 (d, 1H, amide NH), 7.38 (d, 1H, amide NH), 7.72 (d, 1H, amide NH), 8.19 (d, 1H, amide NH).

Example 19

[(S)-2-Guanidinoethyl-1-sulfanylmethyl-Sar][3] cyclosporin A hydrochloride

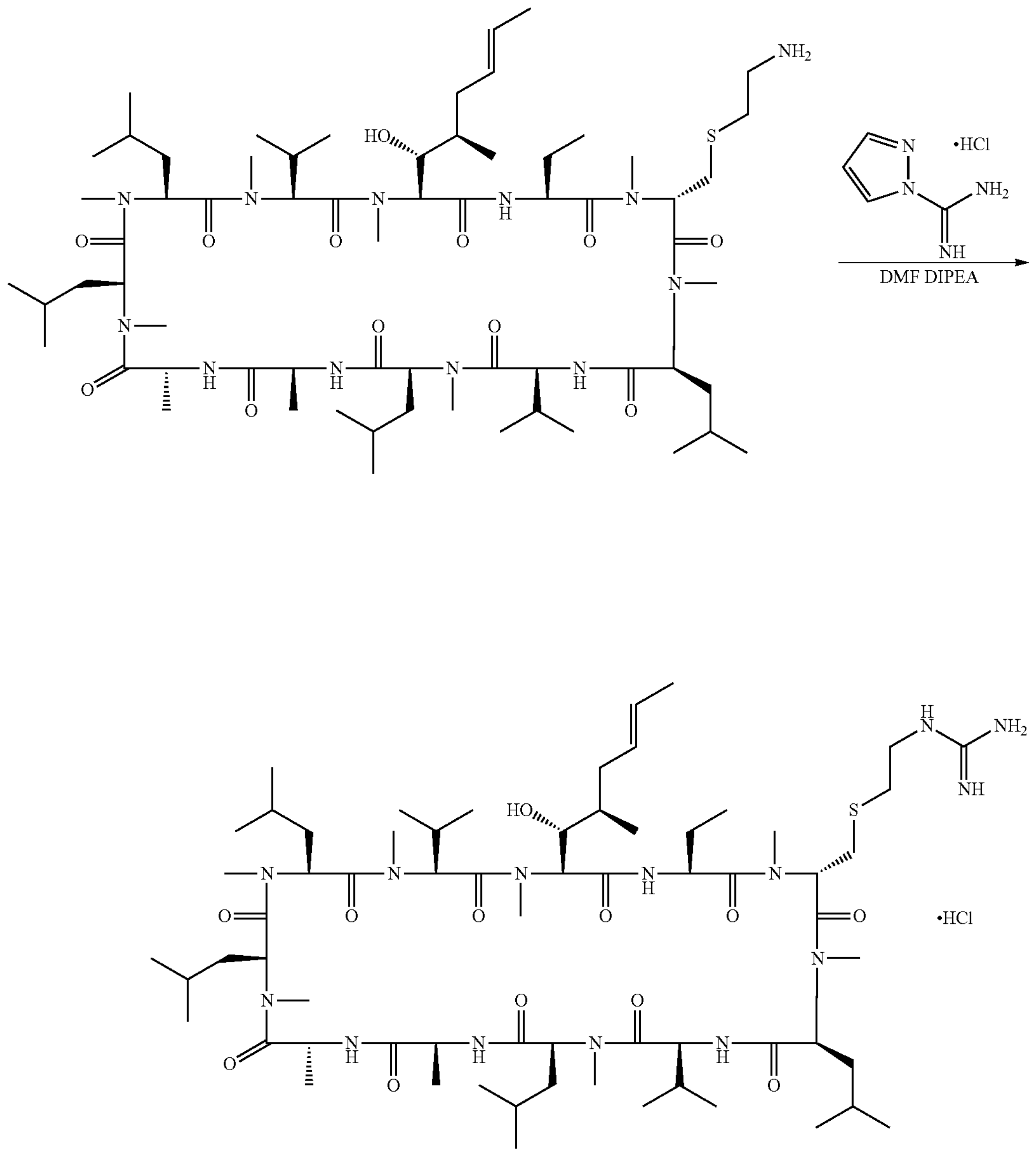

To a solution of [(S)-2-aminoethylthiomethyl-Sar][3] cyclosporinA (0.055 g, 0.042 mmol) in dimethylformamide (0.6 ml) containing diisopropylethylamine (0.0072 ml) was added 1H-pyrazole-1-carboxamidine hydrochloride (0.0055 mg, 0.042 mmol) and the reaction mixture was stirred at room temperature for 22 hours. The reaction mixture was concentrated, the residue was triturated with diethyl ether to give after decantation of the supernatant, a white solid. Partition between dichloromethane and water followed by separation of the organic phase and concentration provided [(S)-2-guanidinoethyl-1-sulfanylmethyl-Sar][3] cyclosporinA hydrochloride.

ESMS $MH^+$1334.5

$^1H$ NMR ($CDCl_3$, ppm) δ 7.12 (d, 1H, amide NH), 7.43 (d, 1H, amide NH), 7.67 (d, 1H, amide NH), 8.31 (d, 1H, amide NH).

[(S)-2-Diethylaminoethyl-1-sulfinylmethyl-Sar][3] cyclosporin A

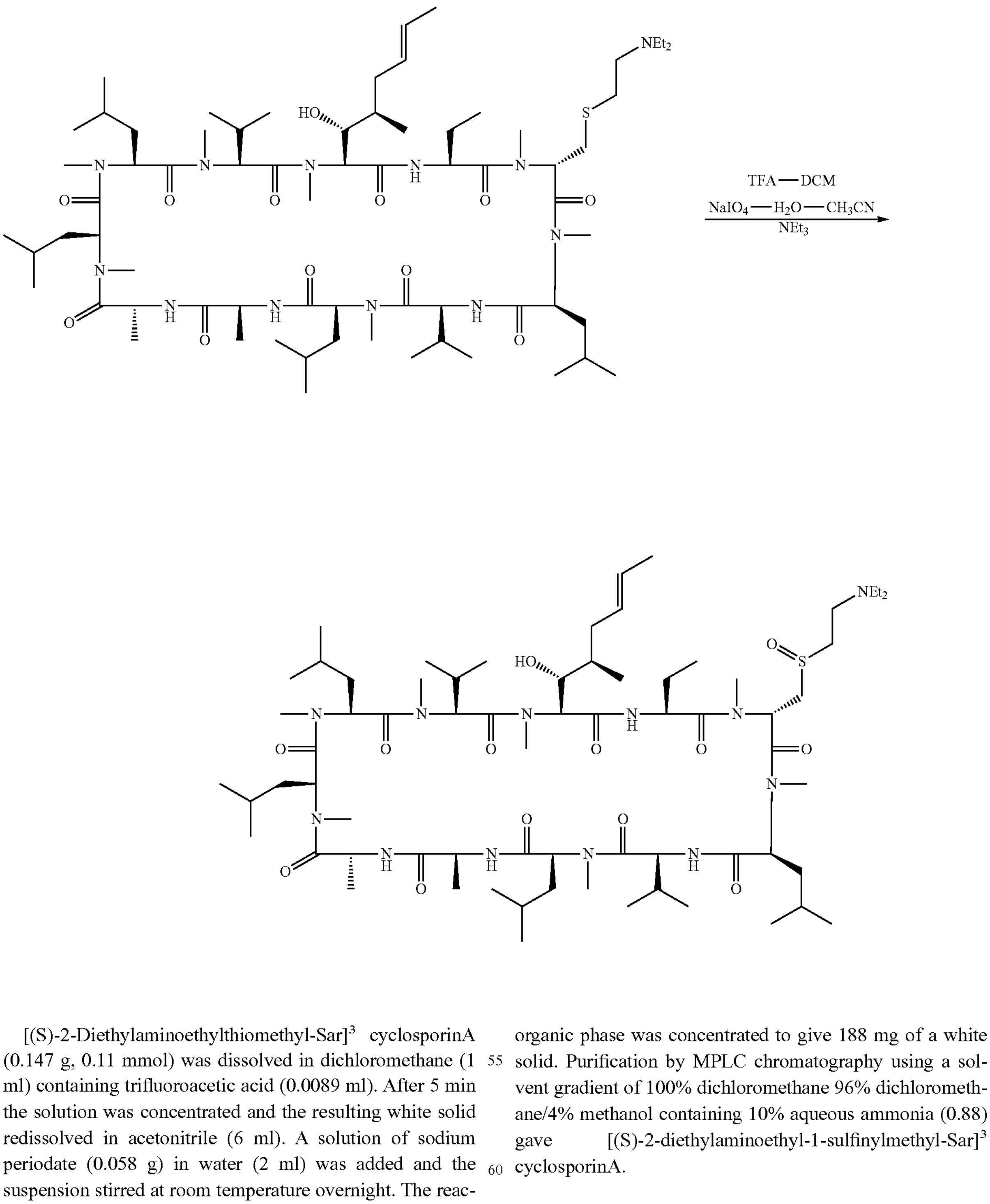

[(S)-2-Diethylaminoethylthiomethyl-Sar][3] cyclosporinA (0.147 g, 0.11 mmol) was dissolved in dichloromethane (1 ml) containing trifluoroacetic acid (0.0089 ml). After 5 min the solution was concentrated and the resulting white solid redissolved in acetonitrile (6 ml). A solution of sodium periodate (0.058 g) in water (2 ml) was added and the suspension stirred at room temperature overnight. The reaction mixture was filtrated, the solid washed with methanol and the filtrate concentrated. The resulting residue was dissolved in dichloromethane (10 ml) containing triethylamine (0.255 ml) then ultrasonicated for 1 hour. The mixture was filtrated through a phase separation cartridge. The organic phase was concentrated to give 188 mg of a white solid. Purification by MPLC chromatography using a solvent gradient of 100% dichloromethane 96% dichloromethane/4% methanol containing 10% aqueous ammonia (0.88) gave [(S)-2-diethylaminoethyl-1-sulfinylmethyl-Sar][3] cyclosporinA.

ESMS $MH^+$1363.8

$^1H$ NMR ($CDCl_3$, ppm) δ 7.19 (1H, d, amide NH), 7.38 (1H, d, amide NH), 7.69 (1H, d, amide NH), 8.28 (1H, d, amide NH).

In a similar way the following compound was prepared:
[Dihydro-MeBmt][1] [(S)-2-diethylaminoethyl-1-sulfinylmethyl-Sar][3] cyclosporin A
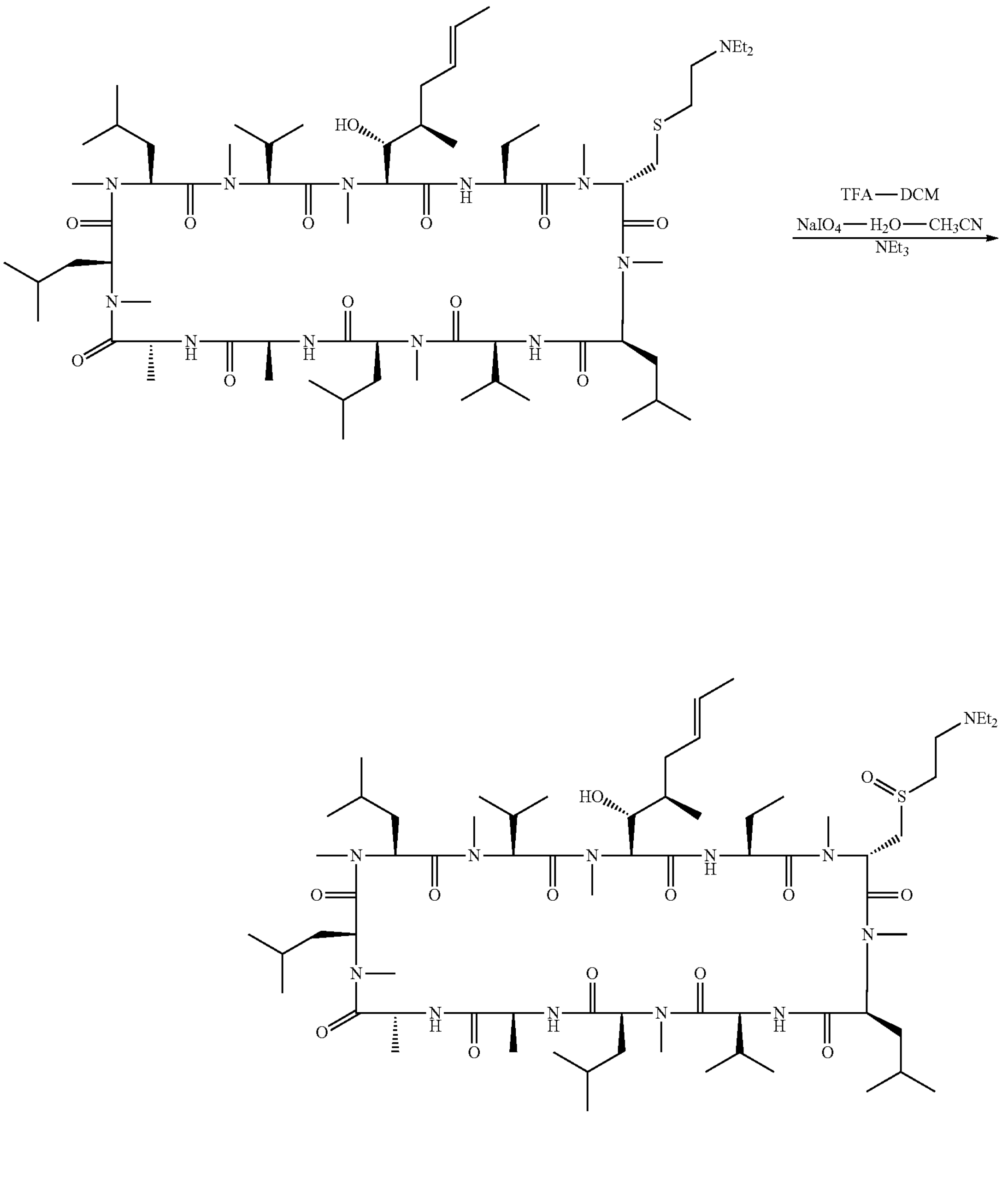
ESMS $MH^+$1366.8
$^1H$ NMR ($CDCl_3$, ppm) 67.20 (1H, d, amide NH), 7.40 (1H, d, amide NH), 7.71 (1H, d, amide NH), 8.30 (1H, d, amide NH).

[(S)-3-Diethylaminopropyl-1-sulfonylmethyl-Sar][3] cyclosporin A

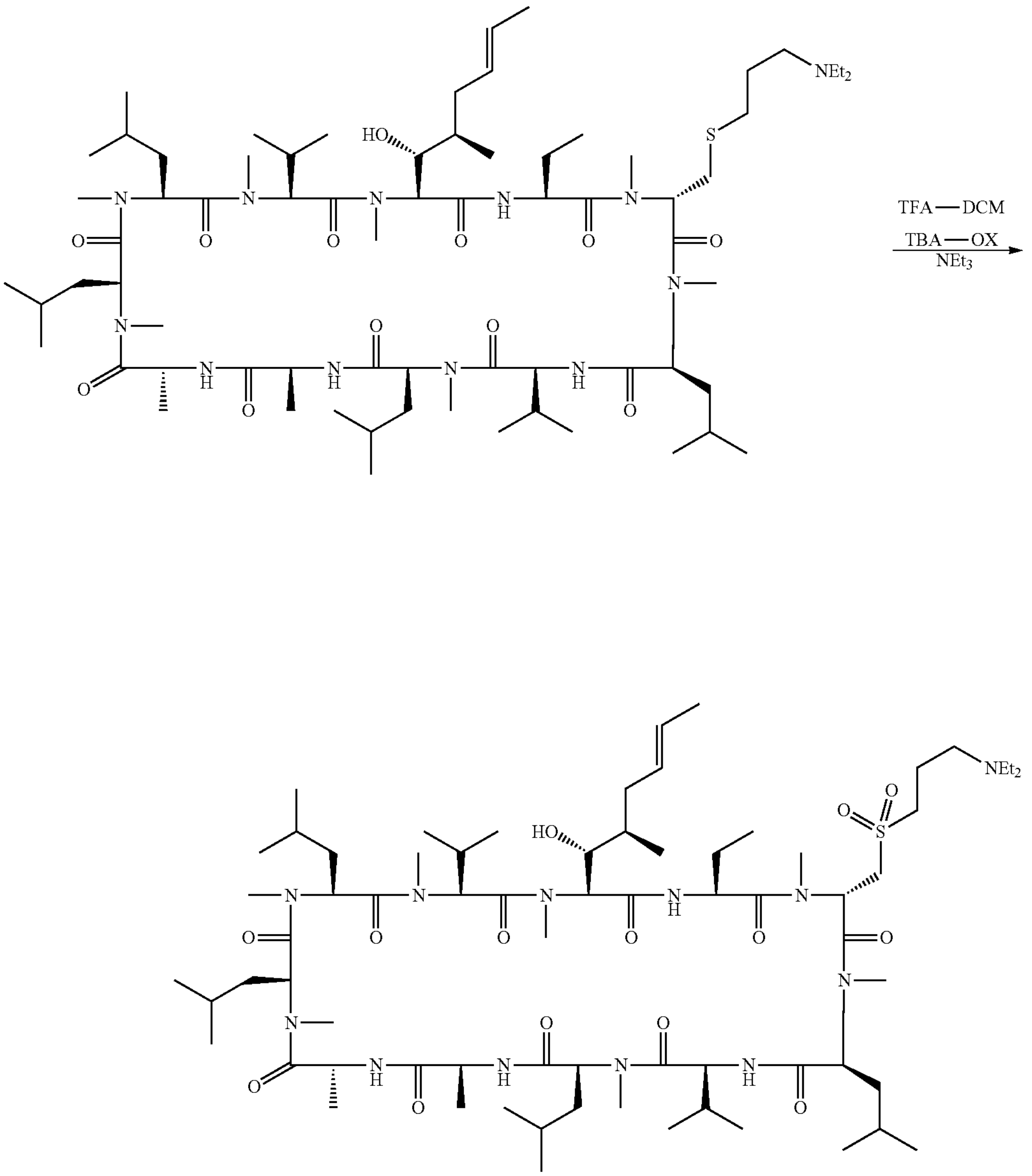

[(S)-3-Diethylaminopropylthiomethyl-Sar][3] cyclosporinA (0.035 g, 0.026 mmol) was dissolved in dichloromethane (2 ml) containing trifluoroacetic acid (0.0021 ml). After 5 min the solution was concentrated and the resulting white solid redissolved in dichloromethane (2 ml). Tetrabutylammonium oxone (0.109 g) was added and the solution stirred at room temperature overnight. The reaction mixture was treated with triethylamine (0.017 ml) then stirred for 90 min before concentrating. The residue was purified by MPLC chromatography using a solvent gradient of 100% dichloromethane 95% dichloromethane/5% methanol containing 10% aqueous ammonia (0.88) to give [(S)-3-diethylaminopropyl-1-sulfonylmethyl-Sar][3] cyclosporinA.

ESMS $MH^+$1393.9

$^1H$ NMR ($CDCl_3$, ppm) δ 7.15 (1H, d, amide NH), 7.20 (1H, d, amide NH), 7.65 (1H, d, amide NH), 8.29 (1H, d, amide NH).

In a similar way the following compound was prepared:
[(S)-3-(Morpholino)propyl-1-sulfonylmethyl-Sar]$^3$ cyclosporin A
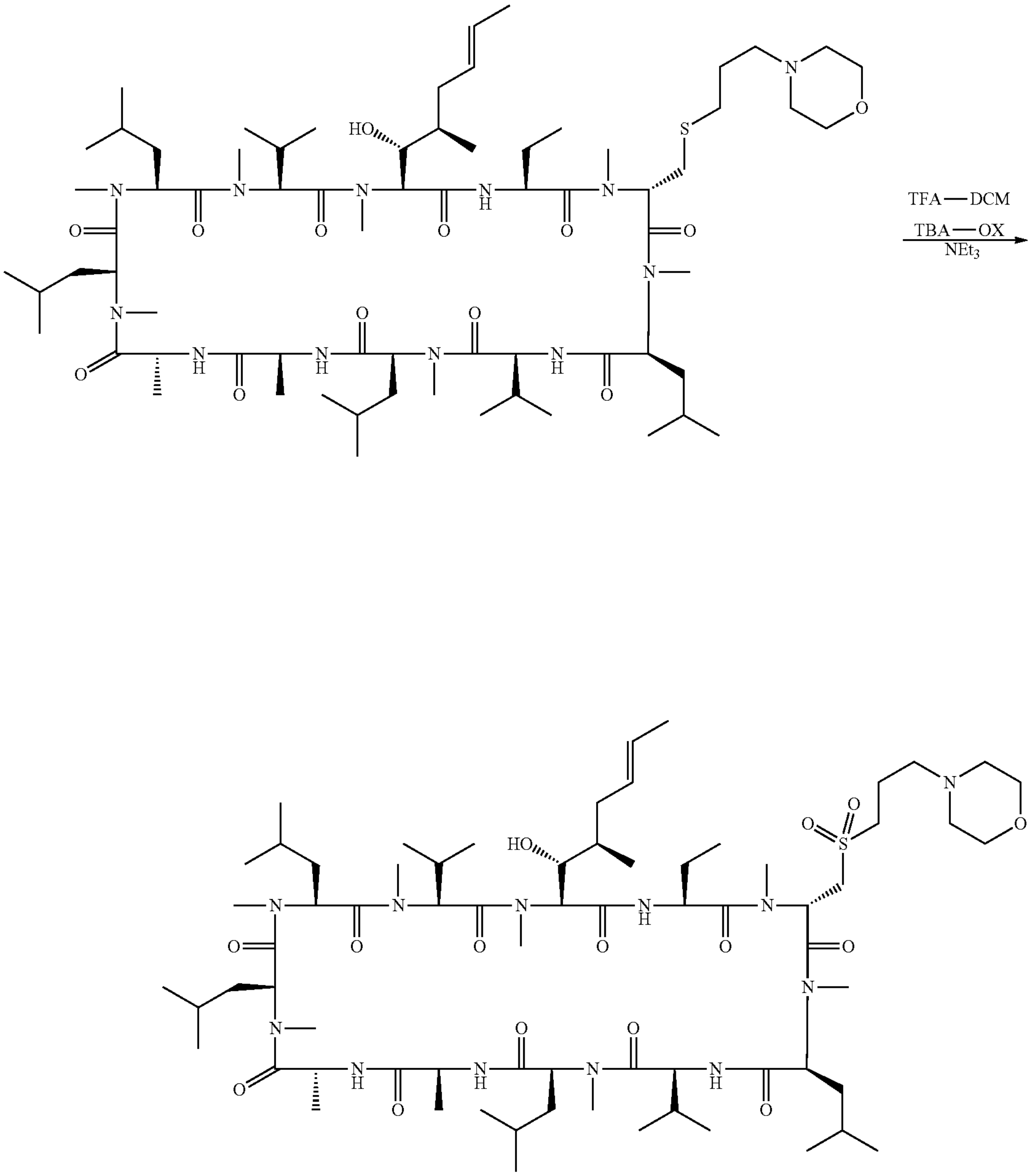
ESMS $MH^+$1407.5
$^1H$ NMR ($CDCl_3$, ppm) δ 7.22 (1H, d, amide NH), 7.27 (1H, d, amide NH), 7.75 (1H, d, amide NH), 8.41 (1H, d, amide NH).

[(S)-(4-Methylpiperidinyn-sulfonylmethyl-Sar]$^3$ cyclosporin A
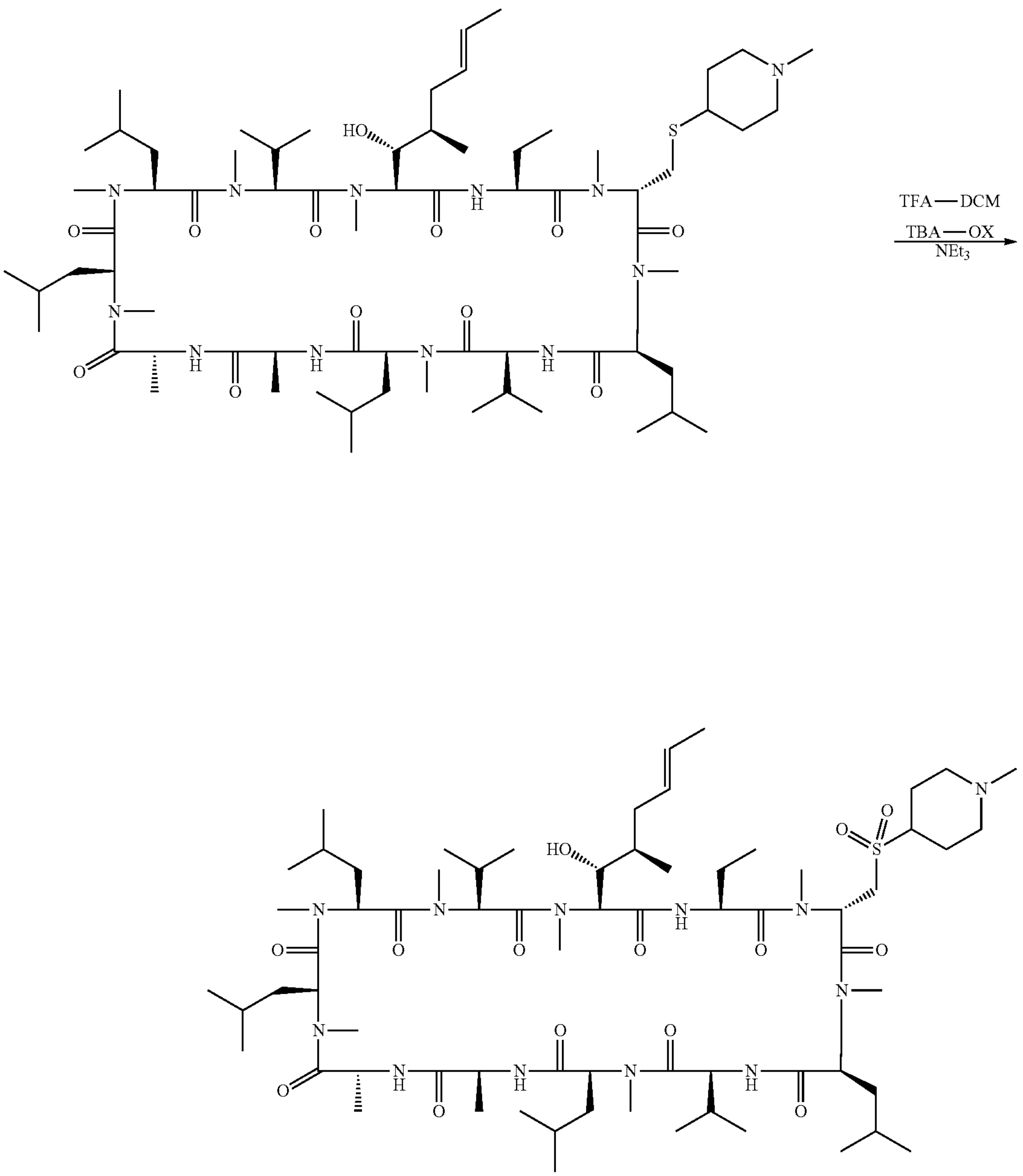
ESMS $MH^+$1377.43
$^1H$ NMR ($CDCl_3$, ppm) δ 7.22 (1H, d, amide NH), 7.29 (1H, d, amide NH), 7.74 (1H, d, amide NH), 8.40 (1H, d, amide NH).

[(S)-(2-Diethylamino-1,1-dimethyl)-ethyl-1-sulfonylmethyl-Sar]$^{3}$ cyclosporin A
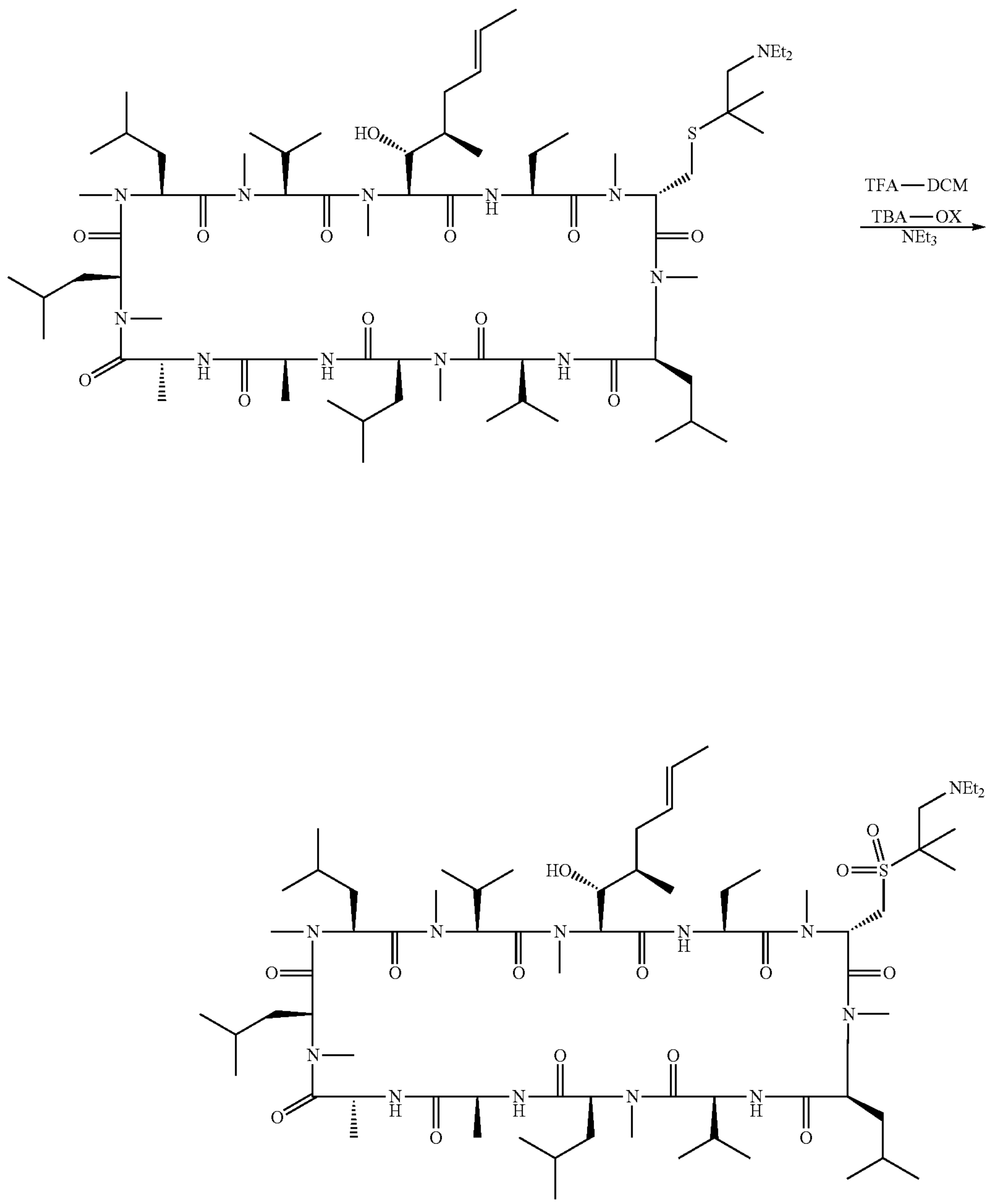
ESMS $MH^{+}$1407.8
$^{1}H$ NMR ($CDCl_3$, ppm) δ7.19 (1H, d, amide NH), 7.37 (1H, d, amide NH), 7.72 (1H, d, amide NH), 8.30 (1H, d, amide NH).

[(S)-(2-Morpholino-1,1-dimethyl)-ethyl-1-sulfonyl-methyl-Sar]³ cyclosporin A
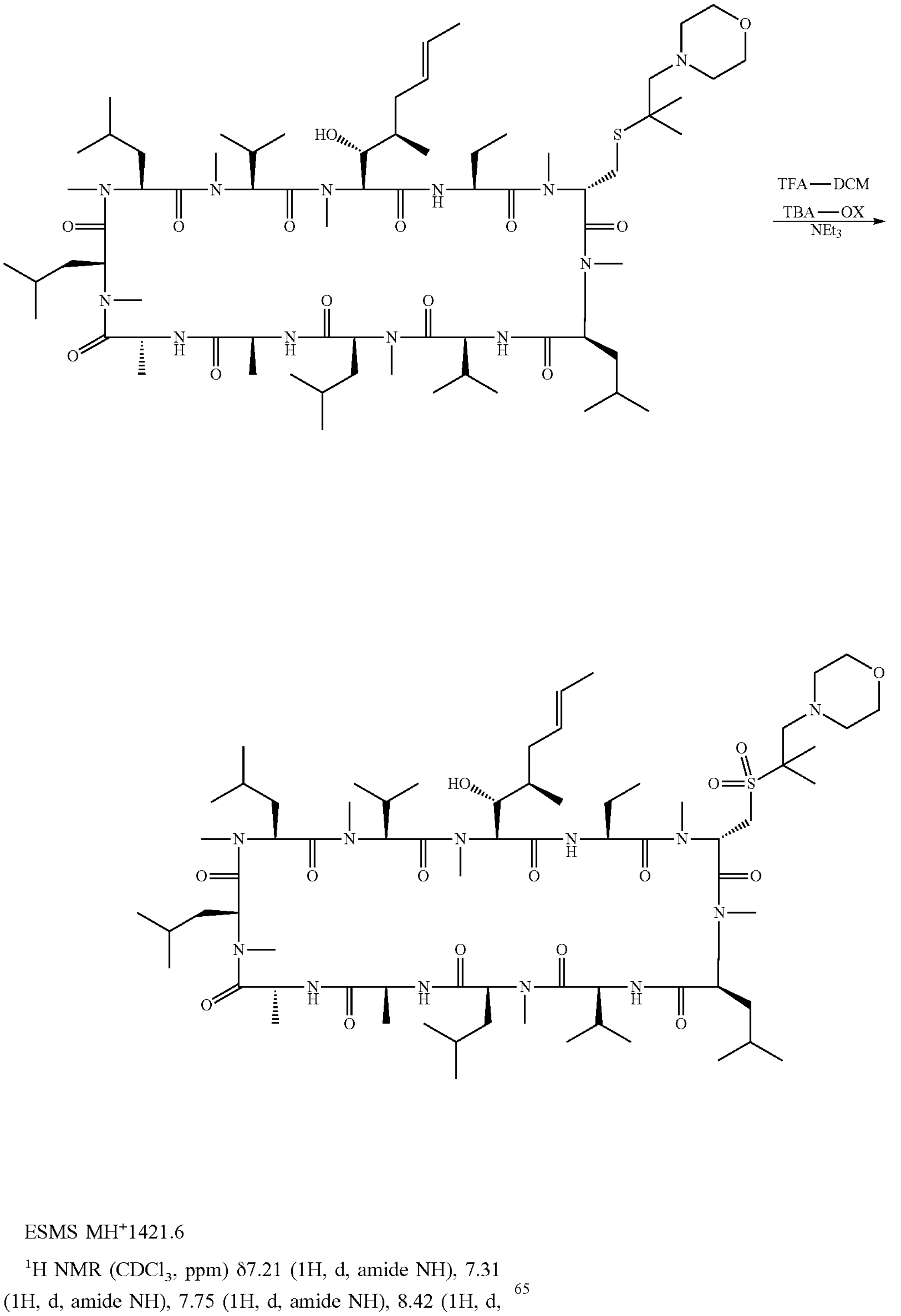
ESMS $MH^+$1421.6
$^1H$ NMR ($CDCl_3$, ppm) δ7.21 (1H, d, amide NH), 7.31 (1H, d, amide NH), 7.75 (1H, d, amide NH), 8.42 (1H, d, amide NH).

[(S)-3-(4-oxy-morpholin-4-yl)-propyl-1-sulfonylmethyl-Sar]$^3$ cyclosporin A
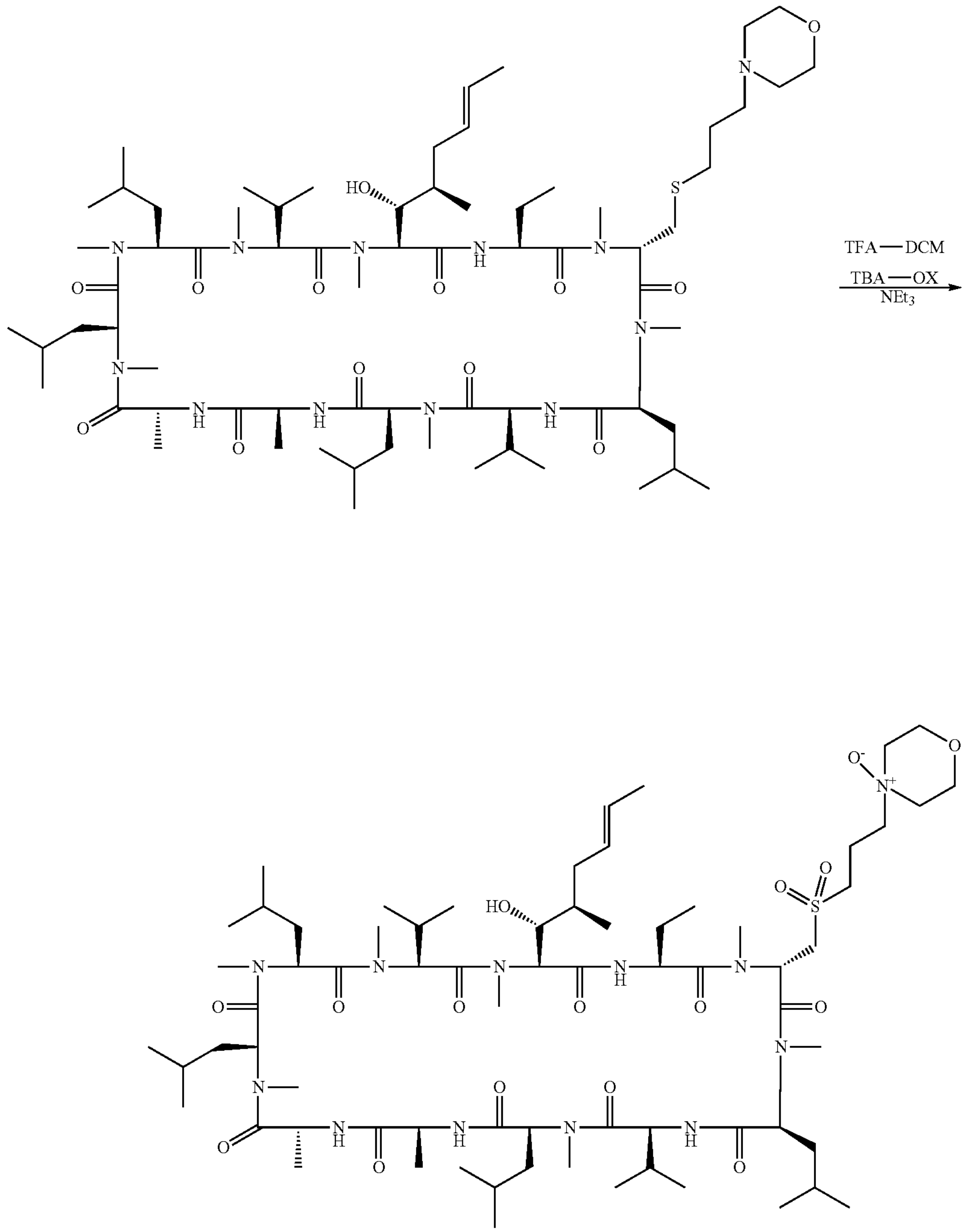
ESMS $MH^+$1423.7
$^1$H NMR ($CDCl_3$, ppm) δ7.21 (1H, d, amide NH), 7.25 (1H, d, amide NH), 7.73 (1H, d, amide NH), 8.35 (1H, d, amide NH).

[(S)-2-(3-Carboxypropionylamino)ethyl-1-sulfanylmethyl-Sar]$^3$ cyclosporin A

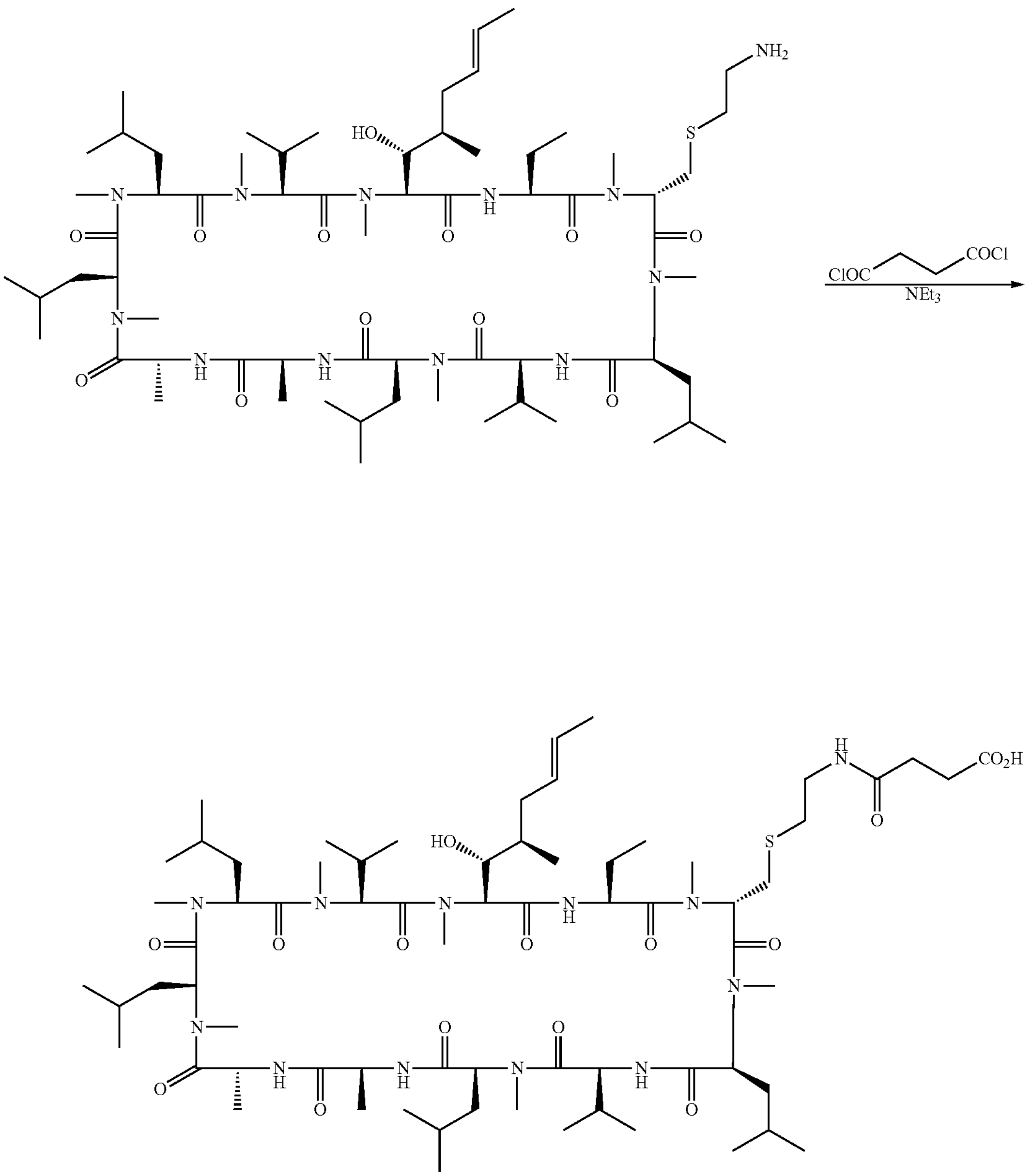

To a stirred solution of [(S)-2-aminoethylthiomethyl-Sar]$^3$ cyclosporinA (0.30 g, 0.23 mmol) in dichloromethane (25 ml) was added triethylamine (0.05 ml, 0.23 mmol) followed by succinyl chloride (0.05 ml, 0.23 mmol) and the reaction mixture was stirred at room temperature for 16 hours. The reaction mixture was diluted with water (20 ml) and the organic layer was separated, dried ($MgSO_4$), filtered and concentrated under vacuum. The resulting yellow solid was purified by passing through a 5 g SCX cartridge using methanol as the eluant, followed by MPLC chromatography using a polar gradient of 100% dichloromethane→95% dichloromethane/5% methanol containing 10% aqueous ammonia (0.88) to give [(S)-2-(3-carboxypropionylamino)ethyl-1-sulfanylmethyl-Sar]$^3$ cyclosporinA.

ESMS $MH^+$1391.8

$^1H$ NMR ($CDCl_3$, ppm) 67.19 (1H, d, amide NH), 7.35 (1H, d, amide NH), 7.71 (1H, d, amide NH), 8.21 (1H, d, amide NH).

In a similar way the following compound was prepared:
[(S)-2-(4-Carboxybutyrylamino)ethyl-1-sulfanylm-ethyl-Sar][3] cyclosporin A
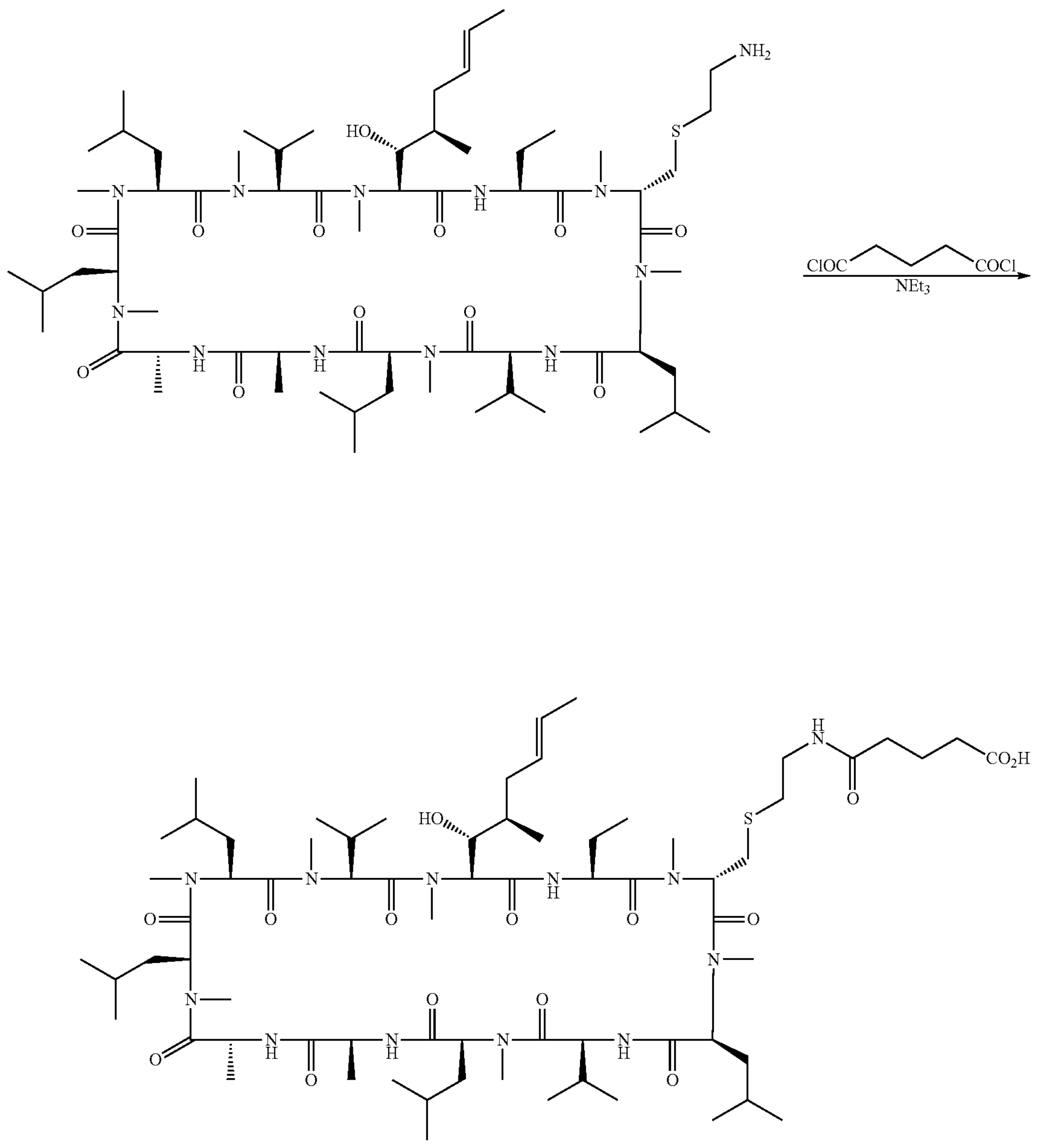
ESMS $MH^+$1405.8
$^1$H NMR ($CDCl_3$, ppm) 67.18 (1H, d, amide NH), 7.35 (1H, d, amide NH), 7.69 (1H, d, amide NH), 8.21 (1H, d, amide NH).

[(S)-2-(Acetylamino-acetylamino)ethyl-1-sulfanylmethyl-Sar]$^3$ cyclosporin A

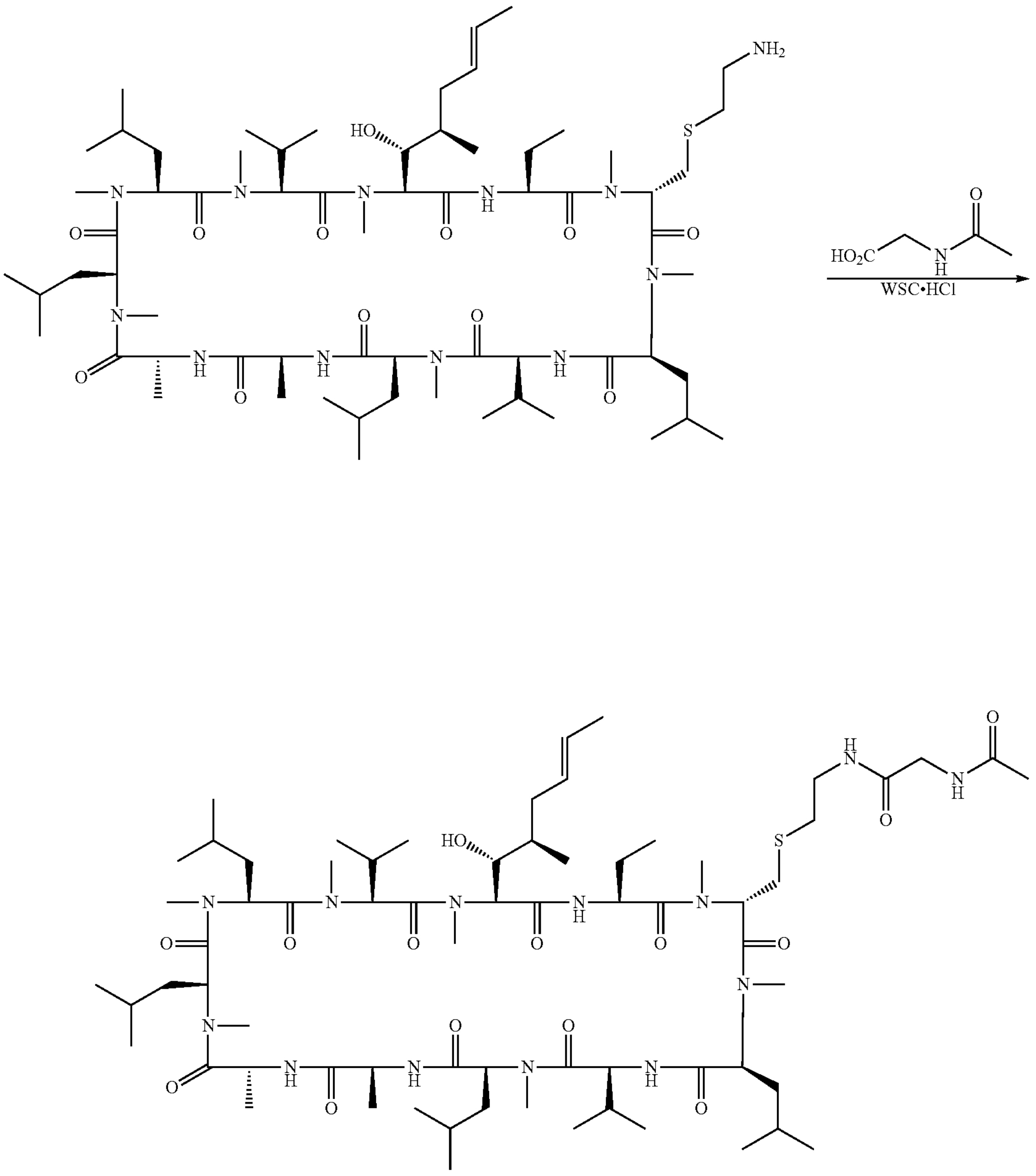

To a stirred solution of [(S)-2-aminoethylthiomethyl-Sar]$^3$ cyclosporinA (0.10 g, 0.078 mmol) in dichloromethane (25 ml) was added N-acetylglycine (0.01 g, 0.084 mmol) and triethylamine (0.01 ml, 0.084 mmol) followed by WSC.HCl (0.022 g, 0.084 mmol) and the reaction mixture was stirred at room temperature for 16 hours. The reaction mixture was diluted with water (20 ml) and the organic layer was separated, dried ($MgSO_4$), filtered and concentrated under vacuum. The resulting yellow solid was purified by passing through a 2 g SCX cartridge using methanol as the eluant, followed by MPLC chromatography using a gradient of 100% dichloromethane→95% dichloromethane/5% methanol containing 10% aqueous ammonia (0.88) to give [(S)-2-(acetylamino-acetylamino)ethyl-1-sulfanylmethyl-Sar]$^3$ cyclosporinA.

ESMS $MH^+$1390.82

$^1H$ NMR ($CDCl_3$, ppm) δ 7.20 (1H, d, amide NH), 7.35 (1H, d, amide NH), 7.71 (1H, d, amide NH), 8.21 (1H, d, amide NH).

In a similar way the following compound was prepared:

[(S)-2-(Dimethylamino-acetylamino)ethyl-1-sulfanylmethyl-Sar]³ cyclosporin A

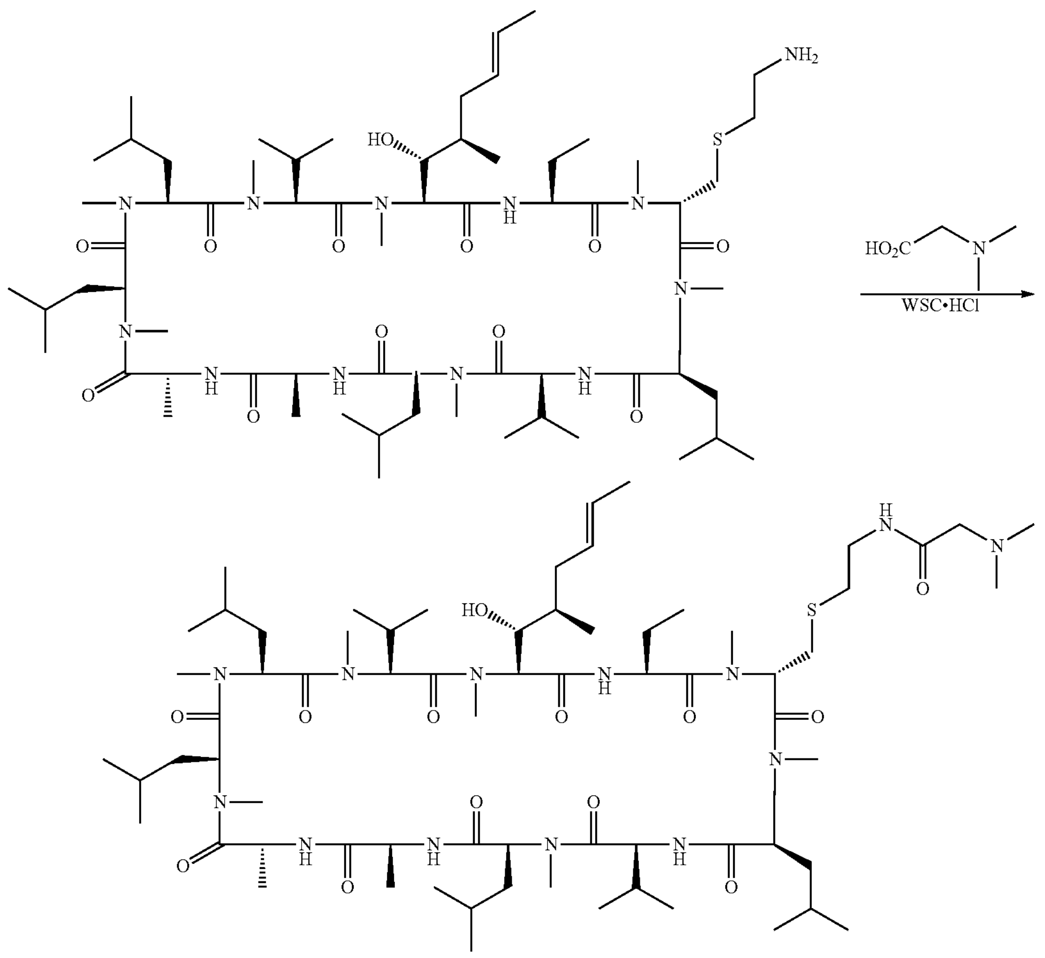

ESMS $MH^+$1376.89

$^1H$ NMR ($CDCl_3$, ppm) δ 7.19 (d, 1H, amide NH), 7.36 (d, 1H, amide NH), 7.71 (d, 1H, amide NH), 8.18 (d, 1H, amide NH).

Data Showing Cyp A Inhibitory Activity & Immunosuppressive Potential of Compounds of Formula (I)

| Compound Tested | *Cyp A nM (n = 1) Protease-free PPlase Assay | **CaN − Cyp A nM | **CaN + Cyp A nM | ***MLR nM |
|---|---|---|---|---|
| Cs A | 1.5 | >10,000 (n = 2) | 210 (n = 3) | 56 |
| Example 1 [methylene-Sar]³ Cs A | 12 | >10,000 (n = 1) | 1,000 (n = 1) | 540 |
| Example 2 [(S)-2 diethylaminothylthio-methyl-Sar]³ Cs A | 2.4 | 3,600 (n = 2) | 2,500 (n = 2) | 3,500 |

-continued

| Compound Tested | *Cyp A nM (n = 1) Protease-free PPlase Assay | **CaN − Cyp A nM | **CaN + Cyp A nM | ***MLR nM |
|---|---|---|---|---|
| Example 3 [(S)-2-(4-pyridyl)ethyl-thiomethyl-Sar]$^3$ Cs A | 4.3 | 11,800 (n = 2) | 6,000 (n = 2) | 2,000 |
| Example 4 [(S)-methylthiomethyl-Sar]$^3$ Cs A | 6.9 | 2,200 (n = 2) | 175 (n = 2) | |
| Example 5 [(S)-pentylthiomethyl-Sar]$^3$ Cs A | 2.3 | >10,000 (n = 2) | 705 (n = 2) | 2,700 |
| Example 6 [(S)-2-aminoethylthio-methyl-Sar]$^3$ Cs A | 4.7 | 3,100 (n = 2) | 1,400 (n = 2) | 10,400 |
| Example 7 [(S)-{(R)-2-amino-2-carbomethoxy-ethyl} thiomethyl-Sar]$^3$ Cs A | 2.9 | 9,800 (n = 2) | 1,600 (n = 2) | |
| Example 8 [(S)-2-dimethylaminoethyl-thiomethyl-Sar]$^3$ Cs A | 4.2 | 2,900 (n = 2) | 4,800 (n = 2) | 4,600 |
| Example 9 [(S)-(4-methylpiperidinyl) thiomethyl-Sar]$^3$ Cs A | 4.8 | 3,300 (n = 2) | 11,000 (n = 2) | 3,800 |
| Example 10 [(S)-2-(morpholino)ethyl-thiomethyl-Sar]$^3$ Cs A | 3.9 | 4,200 (n = 2) | 4,800 (n = 2) | |
| Example 11 [(S)-carbomethoxymethyl-thiomethyl-Sar]$^3$ Cs A | 2.1 | 3,900 (n = 2) | 600 (n = 2) | 19,500 |
| Example 12 [(S)-carbomethoxyethyl-thiomethyl-Sar]$^3$ Cs A | 2.7 | 9,100 (n = 2) | 1,200 (n = 2) | |
| Example 13 [(S)-{(S)-2-amino-2-carbomethoxy-1,1-dimethylethyl}thio-methyl-Sar]$^3$ Cs A | 9.3 | 4,100 (n = 2) | 4,900 (n = 2) | |
| Example 14 [(S)-{(R)-2-amino-2-carbohydroxy-ethyl}thiomethyl-Sar]$^3$ Cs A | 2.9 | 7,400 (n = 2) | 1,200 (n = 2) | |
| Example 15 [(S)-carbohydroxymethyl-thiomethyl-Sar]$^3$ Cs A | 1.9 | 6,800 (n = 2) | 5,300 (n = 2) | 18,300 |
| Example 16 [(S)-{(S)-2-amino-2-carbohydroxy-1,1-dimethylethyl}thio-methyl-Sar]$^3$ Cs A | 5.8 | 2,700 (n = 2) | 2,200 (n = 2) | |
| Example 17 [(S)-carbohydroxyethyl-thiomethyl-Sar]$^3$ Cs A | 2.8 | 17,000 (n = 2) | 3,100 (n = 2) | |

-continued

| Compound Tested | *Cyp A nM (n = 1) Protease-free PPlase Assay | **CaN − Cyp A nM | **CaN + Cyp A nM | ***MLR nM |
|---|---|---|---|---|
| Example 18 [(S)-2-isopropylaminoethyl-thiomethyl-Sar]$^3$ Cs A | 5.2 | 4,600 (n = 2) | 6,100 (n = 2) | 3,300 |
| Example 19 [(S)-2-guanidinoethyl-thiomethyl-Sar]$^3$ Cs A | 6.8 | 3,200 (n = 2) | 1,900 (n = 2) | |

General Procedures Followed to Obtain Data

Protease-Free PPlase Assay

The protease-free PPlase assay measures the rate of cis to trans conversion of a peptide substrate catalyzed by the enzyme cyclophilin A. Addition of an inhibitor slows the catalyzed rate and a $K_i$ value is obtained.

Materials

Assay Buffer: 35 mM HEPES pH 7.8, filtered through a 0.2 μm filter. 50 M DTT was added prior to use each day and then the buffer was stored on ice.

Enzyme: human recombinant Cyp A (Sigma C3805) enzyme was diluted to 1 M with enzyme dilution buffer (20 mM HEPES pH 7.8, 40% glycerol, 50 M DTT and 1 μM BSA) and stored at −20° C.

Substrate: SUC-AAPF-pNA (from Bachem AG, L-1400), 20 mg/ml prepared 0.5 M LiCl in trifluoroethanol.

Method

All readings were taken with an Agilent 8453 Spectrophotometer which consists of a cuvette holder, stirrer and chiller to maintain a stirred cuvette temperature of 10.0±0.1° C. The temperature is monitored by the use of temperature probe. To prevent UV degradation of test compounds, the light below 290 nm was blocked using a glass slide in the light path. 1.5 ml of assay buffer was put into a 3 ml quartz cuvette and cooled to 10.0±0.1° C. while stirring (vigorous but not so fast as to produce cavitation). The inhibitor was diluted in 100% DMSO, and then added to the assay to a maximum final concentration of 0.5% DMSO in the assay. A blank spectrum was obtained, then 3 μL of enzyme was added (2 nM final concentration) and then 3 μL substrate (60 μM final concentration) added. The absorbance was measured at 330 nm for 300 s or 500 s for blank runs (NOTE: the substrate must be added in one quick injection and the measurements started immediately to minimize mixing errors).

A first order rate equation was fitted to the absorbance data, for each concentration of inhibitor, to obtain the rate constant (the first 10 to 15 seconds were excluded as mixing causes errors in this portion of curve). The catalytic rate was calculated from the enzymatic rate constant minus the background rate constant. An exponential curve was generated using the catalytic rate constants versus the inhibitor concentration to obtain the $K_i$ value for the inhibitor.

Calcineurin Phosphatase (CaN) Assay

Calcineurin is a serine-threonine protein phosphatase that on activation dephosphorylates members of the nuclear factor of activated T cells (NFAT), which are important in T lymphocyte activation. Cs A bound to cyclophilin A ("Cyp A") inhibits calcineurin activity, thus resulting in immunosuppressive effects. Although Cs A only inhibits calcineurin when bound to Cyp A, some Cs A analogues will also bind calcineurin in the absence of Cyp A. To investigate the immunosuppressive potential of exemplary compounds of Formula (I), which are cyclosporin analogues, their ability to inhibit calcineurin activity was measured in the presence and absence of Cyp A.

The CaN assay kit used is based on a colorimetric assay for measuring calcineurin phosphatase activity, and it is commercially available (Enzo Life Sciences and Calbiochem). Calmodulin is also required for calcineurin activity and RII phosphopeptide is used as an efficient peptide substrate for calcineurin. We have modified the method to enable measurement of Cyp A-dependent and Cyp A-independent inhibition of calcineurin through the addition of Cyp A in a 1:1 complex with the inhibitor. The detection of free phosphate released is based on the classic Malachite green assay.

Materials Used

Enzo Life Sciences CaN Assay Kit: BML-AK804

2× assay buffer: 100 mM Tris, pH 7.5, 200 mM NaCl, 12 mM $MgCl_2$, 1 mM DTT, 0.05% NP-40, 1 mM $CaCl_2$).

Malachite Green: BIOMOL Green™ reagent.

Calmodulin (Human, recombinant): was thawed on ice, diluted 1:50 with 2× assay buffer, and then stored on ice.

Calcineurin: was thawed quickly, stored on ice immediately, diluted 1:12.5 with 1× assay buffer, and then stored on ice.

R-II Substrate: 915 μL ultrapure water (UPW) was added to the 1.5 mg vial substrate to give a final concentration of 0.75 mM.

Inhibitors: 2.5 mM inhibitor in 100% DMSO.

Cyp A: recombinant human Cyp A, (Sigma C3805), 1 mg/ml.

Method

Inhibitor dilutions: inhibitor compounds were diluted in UPW in polypropylene low-binding 96 well plates at 5× the final assay concentration. For samples 'without Cyp A', a 4-point dilution series of the inhibitor was prepared in duplicate to obtain a final assay concentration of 10, 1, 0.1 and 0.01 μM. For samples 'with Cyp A', a 7-point dilution series was prepared to obtain a 1:1 complex of the inhibitor with Cyp A; the inhibitor and Cyp A final assay concentrations of 10, 3.33, 1.11, 0.37, 0.12, 0.04, 0.014 μM were prepared. Cs A inhibitor controls were also prepared to obtain a final concentration of 10 μM Cs A with and without 10 μM Cyp A.

Assay Setup: using the half area 96 well plates supplied with the kit, 10 μl UPW was added to duplicate wells to provide the non-inhibited control. 10 μl of the inhibitor or the inhibitor/Cyp A complex was added to the appropriate sample wells. 25 μl of the 2× assay buffer with CaM was added to all wells, then 5 μl of CaN was added to all wells (40 Upper well final concentration) except duplicate 'no calcineurin blank' wells to which 5 μL 1× assay buffer was added. The assay plate was placed in an oven at 30° C. for 15 minutes to equilibrate to the reaction temperature. The reaction was started by the addition of 10 μl RH-peptide (0.15 mM final concentration). The reaction was allowed to proceed at 30° C. for a time period in which the reaction is linear for about 60 minutes. The reaction was then terminated by adding 100 μl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no Calcineurin blank' from all the absorbance readings and plotting the background corrected absorbances against $Log_{10}$, inhibitor concentration. A sigmoidal-dose response curve was fitted to the data using GraphPad Prism Software.

Mixed Lymphocyte Reaction ("MLR") Assay

The MLR assay is another means of estimating the immunosuppressive potential of test compounds. Female C57BL/6 and BALB/c mice, 6-8 weeks of age, were obtained from the Frederick Cancer Research and Development Center of the National Cancer Institute (Frederick, Md.). Spleens were harvested aseptically from all mice and single cell suspensions were prepared by disaggregating the cells with frosted glass slides, allowing the debris to settle, and washing the cells twice with complete medium. Complete medium consisted of RPMI 1640 medium containing 25 mM HEPES buffer (HyClone, Logan, Utah) supplemented with 10% heat-inactivated fetal bovine serum (FBS; Atlanta Biologicals, Lawrenceville, Ga.), 100 μg/mL streptomycin, 100 U/mL penicillin G, 0.25 μg/mL amphotericin B (HyClone), 2 mM L-glutamine dipeptide (HyClone), and $2\times10^{-5}$ M 2-mercaptoethanol (Sigma). Cells were washed twice and resuspended in complete medium. Cell counts were performed using a Beckman Coulter Z-1 particle counter (Fullerton, Calif.). Cell viability was determined by propidium iodide (PI) staining using an Accuri C6 flow cytometer (Ann Arbor, Mich.).

Spleen cells from C57BL/6 (H-$2^b$) and BALB/c (H-$2^d$) were used as responder (R) and stimulator (S) cells, respectively. Cells were plated in triplicate in 96-well flat microtiter plates (Costar, Cambridge, Mass.) such that each well contained $2\times10^5$ R and $8\times10^5$ S cells. Cultures were incubated in the absence or presence of various concentrations of Cs A, test compounds, or medium at 37° C. in humidified 5% $CO_2$ for five days, pulsed with $^3$H-thymidine ($^3$H-TdR) for the final 16 hours of incubation, and harvested using a Brandel 96-well cell harvester (Gaithersburg, Md.). Proliferation was measured by counting the radioactivity on filter mats in a Wallac 1450 Microbeta TriLux scintillation counter (Turku, Finland). Controls to demonstrate effective inactivation by the x-irradiation were performed by incubating the S cells with 5 μg/mL of PHA at $2\times10^5$ cells/well. These control cultures were incubated for 3 days under the same conditions as those described for the MLR; lymphoproliferation was determined in the same manner as described above.

Methods of Treatment

Compositions of the invention may be used to treat patients suffering from dry eye, to treat blepharitis and meibomian gland disease, to restore corneal sensitivity that has been impaired due to surgery on the cornea or other surface of the eye, to treat allergic conjunctivitis and atopic and vernal keratoconjunctivitis, and to treat pterygium, ocular symptoms of graft versus host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, ocular rosacea, and pinguecula, and to prevent corneal transplant rejection.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients may actually be a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperplasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, fornix foreshortening, trichiasis, entropion, and madarosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA-$DR^+$, HLA-CD1 $^+$) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

Uveitis, the inflammation of the uvea, is responsible for about 10% of the visual impairment in the United States. Phacoanaphylactic endophthalmitis is a human autoimmune disease. Panuveitis refers to inflammation of the entire uveal (vascular) layer of the eye. Posterior uveitis generally refers to chorioretinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, such as rheumatoid arthritis, Behcet's disease, ankylosing spondylitis, and sarcoidosis; as an isolated immune mediated ocular disorder, such as pars planitis, iridocyclitis etc., unassociated with known etiologies; and following certain systemic diseases which cause antibody-antigen complexes to be deposited in the uveal tissues. Together these disorders represent the non-infectious uveitis.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Uveitis is a prominent feature of Behcet's disease, a multi-system inflammatory disorder also characterized by oral and genital ulcers, cutaneous, vascular, joint, and neurological manifestations.

Rosacea is a chronic and common skin disorder with no identified cause or cure. The pathogenesis of rosacea is thought to have multiple factors. Possible factors include exposure to the demodex folliculorum mite, gastrointestinal disease or a vasodilation disorder, and other triggers such as diet or sunlight. Patients may present with a variety of symptoms, including inflammatory papules, edema, telangiectasia, rhinophyma and ocular symptoms. The ocular signs of rosacea include blepharitis, including anterior blepharitis, conjunctivitis, iritis, iridocyclitis, keratitis, meibomian gland dysfunction, telangiectasia, erythema, chalazion, hordeolum, interpalpebral hyperemia, conjunctival hyperemia, ciliary base injection, bulbar injection, crusts, sleeves, and superficial punctuate keratopathy. The ocular symptoms are nonspecific and may include burning, tearing, decreased tear secretion, redness, and foreign body or gritty or dry sensation, irritation, Itchiness, Blurred vision, Photosensitivity, Watery eyes, bloodshot eyes, Burning, telangiectasia, irregularity of the lid margins, and meibomian gland dysfunction.

Pinguecula is a benign, yellowish brown proliferative growth that forms on the conjunctiva. Pinguecula may cause irritation and scratchiness of the eye, dry eye, inflammation of the conjunctiva and effect appearance of the eye. Inflamed pinguecula, which cause ocular irritation or become unsightly, may require surgical removal. However, the post-operation scar may be as cosmetically objectionable as the pinguecula and pinguecula regrowth may occur following surgical removal.

Allogeneic bone marrow transplantation (BMT) is a well-established treatment for malignant and non-malignant hematological diseases, and is performed in tens of thousands of patients each year. Mature donor T cells within the stem cell graft are the main mediators of the beneficial immune effects, but they are also responsible for the induction of graft-versus-host disease (GVHD), the major cause of morbidity and mortality in BMT patients. GVHD occurs when transplanted donor-derived T cells recognize proteins expressed by recipient antigen-presenting cells. Consequently, this recognition induces donor T-cell activation, proliferation, and differentiation, leading to a cellular and inflammatory attack on recipient target tissues. Acute or chronic GVHD occurs within a 100-day period post-BMT that leads to dermatitis, enteritis, and hepatitis. Ocular symptoms include blurry vision, foreign body sensation, burning sensation, severe light sensitivity, chronic conjunctivitis, dry eye, and eye pain.

Pharmaceutical Compositions

The present invention also relates to pharmaceutical compositions comprising at least one compound of general formula (I), the compound being present alone or in combination with one or more pharmaceutically acceptable excipients. A "pharmaceutically acceptable excipient" is one that is compatible with the active ingredient of the composition and not harmful to the person being administered the pharmaceutical composition. Mixtures of two or more of such suitable excipients may be used.

For topical ocular applications, pharmaceutical compositions may be prepared by combining a therapeutically effective amount of a compound of the invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations. The actual dose of the active compounds of the present invention depends on the specific compound, and on the condition to be treated; the selection of the appropriate dose is well within the knowledge of one of ordinary skill in the art.

U.S. Pat. No. 5,474,979, the entire contents of which are incorporated herein by reference, provides examples of ophthalmically acceptable pharmaceutical excipients. The patent discloses the vehicle used in Restasis®, cyclosporin A 0.05%, manufactured by Allergan, Inc.

A therapeutically effective amount in the claimed pharmaceutical composition is a concentration useful to observe a therapeutic effect as compared to a placebo composition that, except for the absence of a compound of formula (I), is otherwise identical to the pharmaceutical composition.

We claim:

1. A compound selected from the group consisting of:

[(S)-2-diethylaminoethylthiomethyl-Sar]$^3$ cyclosporin A;

[(S)-2-(4-pyridyl)ethylthiomethyl-Sar]$^3$ cyclosporin A;

[(S)-2-aminoethylthiomethyl-Sar]$^3$ cyclosporin A;

[(S)-2-dimethylaminoethylthiomethyl-Sar]$^3$ cyclosporin A;

[(S)-(4-methylpiperidinyl)thiomethyl-Sar]$^3$ cyclosporin A;

[(S)-2-(morpholino)ethylthiomethyl-Sar]$^3$ cyclosporin A; and

[(S)-2-isopropylaminoethylthiomethyl-Sar]$^3$ cyclosporin A;

and pharmaceutically acceptable salts of the foregoing compounds.

2. The compound of claim 1, which is [(S)-2-diethylaminoethylthiomethyl-Sar]$^3$ cyclosporin A, or a pharmaceutically acceptable salt thereof.

3. A pharmaceutical composition comprising a compound of claim 1 or 2, the compound being present alone or in combination with one or more pharmaceutically acceptable excipients.

4. The pharmaceutical composition of claim 3, wherein the concentration of the compound in the composition is about 0.01 to about 0.05 weight percent.

* * * * *